United States Patent
Jackson et al.

(10) Patent No.: US 10,561,359 B2
(45) Date of Patent: Feb. 18, 2020

(54) ELASTIC DEVICES, METHODS, SYSTEMS AND KITS FOR SELECTING SKIN TREATMENT DEVICES

(71) Applicant: Neodyne Biosciences, Inc., Menlo Park, CA (US)

(72) Inventors: Jasper Jackson, Newark, CA (US); John A. Zepeda, Los Altos, CA (US); Michael T. Longaker, Atherton, CA (US); Reinhold H. Dauskardt, Menlo Park, CA (US); Kemal Levi, Mountain View, CA (US); William R. Beasley, Los Altos, CA (US)

(73) Assignee: Neodyne Biosciences, Inc., Menlo Park, CA (US)

( * ) Notice: Subject to any disclaimer, the term of this patent is extended or adjusted under 35 U.S.C. 154(b) by 0 days.

(21) Appl. No.: 13/791,728

(22) Filed: Mar. 8, 2013

(65) Prior Publication Data
US 2013/0190655 A1     Jul. 25, 2013

Related U.S. Application Data

(63) Continuation-in-part of application No. 13/691,656, filed on Nov. 30, 2012, now Pat. No. 9,827,447.
(Continued)

(51) Int. Cl.
*A61B 5/00*     (2006.01)
*A61L 15/44*     (2006.01)
(Continued)

(52) U.S. Cl.
CPC .......... *A61B 5/442* (2013.01); *A61B 5/0031* (2013.01); *A61B 5/103* (2013.01); *A61B 5/1036* (2013.01);
(Continued)

(58) Field of Classification Search
CPC .......... A61L 15/26; A61L 15/42; A61L 15/44; A61L 15/58; A61B 5/0031; A61B 5/1036; A61B 5/103; A61B 5/686
(Continued)

(56) References Cited

U.S. PATENT DOCUMENTS

| | | |
|---|---|---|
| 114,750 A | 5/1871 | Battersby |
| 363,538 A | 5/1887 | Penny |

(Continued)

FOREIGN PATENT DOCUMENTS

| | | |
|---|---|---|
| CA | 2321491 A1 | 9/1999 |
| CA | 2621387 A1 | 3/2007 |

(Continued)

OTHER PUBLICATIONS

U.S. Appl. No. 61/443,647, filed Feb. 16, 2011 Jackson et al., titled "Wound or Skin Treatment Devices and Methods".
(Continued)

*Primary Examiner* — Patrick Fernandes
(74) *Attorney, Agent, or Firm* — Dorsey & Whitney LLP

(57) ABSTRACT

Devices, kits, systems and methods are described herein for treatment to skin, including but not limited to wound healing, the treatment, amelioration, and/or prevention of scars or keloids. Certain devices kits, systems and methods are used to select treatment parameters, devices or methods for treating skin in a location, zone, or region of skin having particular mechanical or other properties.

18 Claims, 24 Drawing Sheets

Related U.S. Application Data

(60) Provisional application No. 61/566,590, filed on Dec. 2, 2011.

(51) Int. Cl.
*A61L 15/42* (2006.01)
*A61B 5/103* (2006.01)
*A61L 15/26* (2006.01)

(52) U.S. Cl.
CPC .............. *A61B 5/686* (2013.01); *A61L 15/26* (2013.01); *A61L 15/42* (2013.01); *A61L 15/44* (2013.01)

(58) Field of Classification Search
USPC ....................................................... 600/587
See application file for complete search history.

(56) References Cited

U.S. PATENT DOCUMENTS

| | | |
|---|---|---|
| 633,050 A | 9/1899 | Spenard |
| 1,074,413 A | 9/1913 | Baun et al. |
| 1,774,489 A | 8/1930 | Sarason |
| 1,969,188 A | 8/1934 | Spicer |
| 2,018,517 A | 10/1935 | Fetter |
| 2,303,131 A | 11/1942 | Morgan |
| 2,371,978 A | 3/1945 | Perham |
| 2,421,193 A | 5/1947 | Gardner |
| 2,472,009 A | 5/1949 | Gardner |
| 2,714,382 A | 8/1955 | Alcala |
| 2,722,220 A | 11/1955 | Mestrand |
| 2,762,371 A | 9/1956 | Guio |
| 3,103,218 A | 9/1963 | Ajemian |
| 3,402,716 A | 9/1968 | Baxter |
| 3,487,836 A | 1/1970 | Niebel et al. |
| 3,528,426 A | 9/1970 | Vukojevic |
| 3,575,782 A | 4/1971 | Hansen |
| 3,613,679 A * | 10/1971 | Bijou ............................. 602/75 |
| 3,645,835 A | 2/1972 | Hodgson |
| 3,698,395 A | 10/1972 | Harrith |
| 3,863,640 A | 2/1975 | Haverstock |
| 3,926,193 A | 12/1975 | Hasson |
| 3,933,158 A | 1/1976 | Haverstock |
| 3,983,878 A | 10/1976 | Kawchitch |
| 4,038,989 A | 8/1977 | Romero-Sierra et al. |
| 4,073,298 A | 2/1978 | Le Roy |
| 4,114,624 A | 9/1978 | Haverstock |
| 4,141,363 A | 2/1979 | James et al. |
| 4,173,131 A | 11/1979 | Pendergrass et al. |
| 4,222,383 A | 9/1980 | Schossow |
| 4,282,005 A | 8/1981 | Sato |
| 4,346,700 A | 8/1982 | Dunshee |
| 4,370,981 A | 2/1983 | Sanderson |
| 4,413,621 A | 11/1983 | McCracken |
| 4,423,731 A | 1/1984 | Roomi |
| 4,425,176 A | 1/1984 | Shibano et al. |
| 4,447,482 A | 5/1984 | Heinbelman et al. |
| 4,496,535 A | 1/1985 | Gould et al. |
| 4,531,521 A | 7/1985 | Haverstock |
| 4,535,772 A | 8/1985 | Sheehan |
| 4,539,990 A | 9/1985 | Stivala |
| 4,549,653 A | 10/1985 | Lauritzen |
| 4,598,004 A | 7/1986 | Heinecke |
| 4,605,005 A | 8/1986 | Sheehan |
| 4,646,731 A | 3/1987 | Brower |
| 4,653,492 A | 3/1987 | Parsons |
| 4,696,301 A | 9/1987 | Barabe |
| 4,699,133 A | 10/1987 | Schafer et al. |
| 4,702,251 A | 10/1987 | Sheehan |
| 4,706,661 A | 11/1987 | Barrett |
| 4,732,146 A | 3/1988 | Fasline et al. |
| 4,742,826 A | 5/1988 | McLorg |
| 4,753,232 A | 6/1988 | Ward |
| 4,780,168 A | 10/1988 | Beisang et al. |
| 4,787,381 A | 11/1988 | Hubbard et al. |
| 4,807,613 A | 2/1989 | Koehnke et al. |
| 4,815,457 A | 3/1989 | Mazars et al. |
| 4,815,468 A | 3/1989 | Annand |
| 4,825,866 A | 5/1989 | Pierce |
| 4,881,546 A | 11/1989 | Kaessmann |
| 4,915,102 A | 4/1990 | Kwiatek et al. |
| 4,917,929 A | 4/1990 | Heinecke |
| 4,924,866 A | 5/1990 | Yoon |
| 4,950,282 A | 8/1990 | Beisang et al. |
| RE33,353 E | 9/1990 | Heinecke et al. |
| 4,984,584 A | 1/1991 | Hansen et al. |
| 5,011,492 A | 4/1991 | Heimerl et al. |
| 5,026,389 A | 6/1991 | Thieler |
| 5,047,047 A | 9/1991 | Yoon |
| 5,058,579 A | 10/1991 | Terry et al. |
| 5,066,299 A | 11/1991 | Bellingham |
| 5,106,629 A | 4/1992 | Cartmell et al. |
| 5,127,412 A | 7/1992 | Cosmetto et al. |
| 5,176,703 A | 1/1993 | Peterson |
| 5,234,462 A | 8/1993 | Pavletic |
| 5,259,835 A | 11/1993 | Clark et al. |
| 5,263,965 A | 11/1993 | Roth |
| 5,263,970 A | 11/1993 | Preller |
| 5,333,753 A | 8/1994 | Etheredge |
| 5,383,900 A | 1/1995 | Krantz |
| 5,507,775 A | 4/1996 | Ger et al. |
| 5,520,762 A | 5/1996 | Rasmussen et al. |
| 5,522,879 A | 6/1996 | Scopelianos |
| 5,545,713 A | 8/1996 | Krejci et al. |
| 5,549,713 A | 8/1996 | Kim |
| 5,552,162 A | 9/1996 | Lee |
| 5,562,705 A | 10/1996 | Whiteford |
| 5,628,724 A | 5/1997 | Debusk et al. |
| 5,649,960 A | 7/1997 | Pavletic |
| 5,662,624 A | 9/1997 | Sundstroem et al. |
| 5,662,714 A | 9/1997 | Charvin et al. |
| 5,662,717 A | 9/1997 | Burns |
| 5,713,842 A | 2/1998 | Kay |
| 5,723,009 A | 3/1998 | Frechet et al. |
| 5,758,662 A | 6/1998 | Hall |
| 5,759,560 A | 6/1998 | Dillon |
| 5,779,659 A | 7/1998 | Allen |
| 5,820,877 A | 10/1998 | Yamaguchi et al. |
| 5,885,254 A | 3/1999 | Matyas |
| 5,891,076 A | 4/1999 | Fabo |
| 5,919,476 A | 7/1999 | Fischer et al. |
| 5,931,800 A | 8/1999 | Rasmussen et al. |
| 5,947,998 A | 9/1999 | Cartmell et al. |
| 5,998,694 A | 12/1999 | Jensen et al. |
| 6,007,564 A | 12/1999 | Haverstock |
| 6,043,406 A | 3/2000 | Sessions et al. |
| 6,093,465 A | 7/2000 | Gilchrist et al. |
| 6,120,525 A | 9/2000 | Westcott |
| 6,255,552 B1 | 7/2001 | Cummings et al. |
| 6,264,976 B1 | 7/2001 | Heinecke et al. |
| 6,284,941 B1 | 9/2001 | Cox et al. |
| 6,297,420 B1 | 10/2001 | Heincke |
| 6,297,423 B1 | 10/2001 | Schoenfeldt et al. |
| 6,343,224 B1 | 1/2002 | Parker |
| 6,346,653 B1 | 2/2002 | Sessions et al. |
| 6,410,818 B1 | 6/2002 | Oyaski |
| 6,469,066 B1 | 10/2002 | Dosch et al. |
| 6,485,503 B2 | 11/2002 | Jacobs et al. |
| 6,495,230 B1 | 12/2002 | do Canto |
| 6,570,051 B1 | 5/2003 | Beaudry |
| 6,572,878 B1 | 6/2003 | Blaine |
| 6,573,419 B2 | 6/2003 | Naimer |
| 6,634,653 B2 | 10/2003 | Chatterjea |
| 6,726,696 B1 | 4/2004 | Houser et al. |
| 6,759,481 B2 | 7/2004 | Tong |
| 6,822,133 B2 | 11/2004 | Lebner |
| 6,831,205 B2 | 12/2004 | Lebner |
| 6,870,074 B2 | 3/2005 | Gilman |
| 6,986,855 B1 | 1/2006 | Hood et al. |
| 7,066,182 B1 | 6/2006 | Dunshee |
| 7,066,934 B2 | 6/2006 | Kirsch |
| 7,122,712 B2 | 10/2006 | Lutri et al. |
| 7,135,606 B1 | 11/2006 | Dozier et al. |
| 7,227,050 B2 | 6/2007 | Sigurjonsson et al. |

(56) References Cited

U.S. PATENT DOCUMENTS

| | | |
|---|---|---|
| 7,332,641 B2 | 2/2008 | Lebner et al. |
| 7,354,446 B2 | 4/2008 | Lebner |
| 7,414,168 B2 | 8/2008 | Lebner |
| 7,456,332 B2 | 11/2008 | Beaudry |
| 7,511,185 B2 | 3/2009 | Lebner |
| 7,563,941 B2 | 7/2009 | Lebner et al. |
| 7,683,234 B2 | 3/2010 | Gurtner et al. |
| 7,834,232 B2 | 11/2010 | Rastegar et al. |
| 8,063,263 B2 | 11/2011 | Gurtner et al. |
| 8,168,850 B2 | 5/2012 | Gurtner et al. |
| 8,183,428 B2 | 5/2012 | Gurtner et al. |
| 8,389,791 B2 | 3/2013 | Gurtner et al. |
| 8,395,011 B2 | 3/2013 | Zepeda et al. |
| 8,592,640 B2 | 11/2013 | Zepeda et al. |
| 8,674,164 B2 | 3/2014 | Zepeda et al. |
| 9,827,447 B1 | 11/2017 | Levi et al. |
| 2002/0013300 A1 | 1/2002 | Capelli-Schellpfeffer |
| 2002/0193723 A1 | 12/2002 | Batdorf, Sr. |
| 2003/0014053 A1 | 1/2003 | Nguyen et al. |
| 2003/0040687 A1 | 2/2003 | Boynton et al. |
| 2003/0092969 A1 | 5/2003 | O'Malley et al. |
| 2003/0220700 A1 | 11/2003 | Hammer et al. |
| 2005/0033215 A1 | 2/2005 | Lebner |
| 2005/0034731 A1 | 2/2005 | Rousseau et al. |
| 2005/0070956 A1 | 3/2005 | Rousseau |
| 2005/0080453 A1 | 4/2005 | Lebner et al. |
| 2005/0095275 A1* | 5/2005 | Zhu ............... A61F 13/00063 424/445 |
| 2005/0095276 A1 | 5/2005 | Kartheus et al. |
| 2005/0125051 A1 | 6/2005 | Eidenschink et al. |
| 2005/0245966 A1 | 11/2005 | Hammerslag et al. |
| 2005/0274453 A1 | 12/2005 | Anvar |
| 2006/0009099 A1 | 1/2006 | Jonn et al. |
| 2006/0020235 A1 | 1/2006 | Siniaguine |
| 2006/0037091 A1 | 2/2006 | Gurtner et al. |
| 2006/0064024 A1 | 3/2006 | Schnall |
| 2006/0246802 A1 | 11/2006 | Hughes et al. |
| 2006/0282135 A1 | 12/2006 | Tankovich |
| 2007/0093161 A1 | 4/2007 | Eede et al. |
| 2007/0142761 A1 | 6/2007 | Aali |
| 2007/0178121 A1 | 8/2007 | First et al. |
| 2007/0191752 A1 | 8/2007 | Lebner |
| 2007/0282235 A1 | 12/2007 | Beaudry |
| 2007/0282374 A1 | 12/2007 | Sogard et al. |
| 2008/0033334 A1* | 2/2008 | Gurtner et al. ............ 602/50 |
| 2008/0051687 A1 | 2/2008 | Rogers |
| 2008/0208098 A1 | 8/2008 | Rennix |
| 2008/0228220 A1 | 9/2008 | Weiser |
| 2009/0131845 A1 | 5/2009 | Gurtner et al. |
| 2009/0131846 A1 | 5/2009 | Gurtner et al. |
| 2009/0163844 A1 | 6/2009 | Gurtner et al. |
| 2009/0177136 A1* | 7/2009 | Liedtke ............... A61F 13/02 602/58 |
| 2010/0191253 A1 | 7/2010 | Oostman, Jr. et al. |
| 2010/0280428 A1 | 11/2010 | Widgerow et al. |
| 2011/0054283 A1* | 3/2011 | Shuler ............ A61B 5/14539 600/364 |
| 2011/0152738 A1 | 6/2011 | Zepeda et al. |
| 2011/0319798 A1 | 12/2011 | DiGrazia |
| 2012/0035521 A1 | 2/2012 | Zepeda et al. |
| 2012/0046586 A1 | 2/2012 | Gurtner et al. |
| 2012/0046590 A1 | 2/2012 | Yock et al. |
| 2012/0046591 A1 | 2/2012 | Gurtner et al. |
| 2012/0083724 A1 | 4/2012 | Zepeda et al. |
| 2012/0203273 A1 | 8/2012 | Riskin et al. |
| 2012/0221044 A1 | 8/2012 | Archibald et al. |
| 2012/0226214 A1 | 9/2012 | Gurtner et al. |
| 2012/0226306 A1 | 9/2012 | Jackson et al. |
| 2013/0012858 A1 | 1/2013 | Jackson et al. |
| 2013/0110026 A1 | 5/2013 | Jackson et al. |
| 2013/0184629 A1 | 7/2013 | Gurtner et al. |
| 2013/0190655 A1 | 7/2013 | Jackson et al. |
| 2013/0190673 A1 | 7/2013 | Gurtner et al. |
| 2014/0228731 A1 | 8/2014 | Jackson et al. |

FOREIGN PATENT DOCUMENTS

| | | |
|---|---|---|
| CN | 1414842 A | 4/2003 |
| CN | 1608604 A | 4/2005 |
| CN | 101836918 A | 9/2010 |
| CN | 102665623 B | 12/2014 |
| EP | 2161011 A1 | 3/2010 |
| EP | 2464322 A2 | 6/2012 |
| JP | 2004-515256 A | 5/2004 |
| JP | 2004-223087 A | 8/2004 |
| JP | 2004-536898 A | 12/2004 |
| JP | 2006-513748 A | 4/2006 |
| JP | 2007-537781 A | 12/2007 |
| JP | 2009-545382 A | 12/2009 |
| JP | 2013-501591 A | 1/2013 |
| RU | 2019138 C1 | 9/1994 |
| WO | WO-1997/17919 A1 | 5/1997 |
| WO | WO-1997/30700 A2 | 8/1997 |
| WO | WO-1997/30700 A3 | 8/1997 |
| WO | WO-2000/53139 A1 | 9/2000 |
| WO | WO-2001/039693 A2 | 6/2001 |
| WO | WO-2002/15816 A2 | 2/2002 |
| WO | WO-2002/15816 A3 | 2/2002 |
| WO | WO-2002-45698 A2 | 6/2002 |
| WO | WO-2002-45698 A3 | 6/2002 |
| WO | WO-2002/087645 A1 | 11/2002 |
| WO | WO-2002/092783 A2 | 11/2002 |
| WO | WO-2002/092783 A3 | 11/2002 |
| WO | WO-2004/060413 A1 | 7/2004 |
| WO | WO-2004/073567 A1 | 9/2004 |
| WO | WO-2008/019051 A2 | 9/2004 |
| WO | WO-2008/019051 A3 | 9/2004 |
| WO | WO-2005/079674 A1 | 9/2005 |
| WO | WO-2005/096981 A2 | 10/2005 |
| WO | WO-2005/096981 A3 | 10/2005 |
| WO | WO-2006/124671 A2 | 11/2006 |
| WO | WO-2006/124671 A3 | 11/2006 |
| WO | WO-2011/019859 A2 | 2/2011 |
| WO | WO-2011/019859 A3 | 2/2011 |
| WO | WO-2011/159623 A1 | 12/2011 |
| WO | WO-2012/094648 A1 | 7/2012 |
| WO | WO-2012/119131 A1 | 9/2012 |
| WO | WO-2014/021934 A2 | 2/2014 |
| WO | WO-2014/021934 A3 | 2/2014 |

OTHER PUBLICATIONS

U.S. Appl. No. 61/512,340, filed Jul. 27, 2011, Zepeda et al., titled "Skin Straining Device Method".

Artz et al., "Burns: A Team Approach", (Saunders), Philadelphia, 1979, pp. 24-44.

Barker, D. E., "Skin Thickness in the Human", Plast. Reconstr. Surg., vol. 7, 1951, pp. 115-116.

Gurtner et al., "Improving Cutaneous Scar by Controlling the Mechanical Environment: Large Animal and Phase I Studies", Annals of Surgery, vol. 00, No. 00, 2011, pp. 1-9.

Lee, Y., "Skin Thickness of Korean Adults", Surg. Radiol. Anat., vol. 24, 2002, pp. 183-189.

Marcellier et al., "Optical Analysis of Displacement and Strain Fields on Human Skin", Skin Res. Technol., vol. 7, 2001, pp. 246-253.

Staloff et al., "Measurement of Skin Stretch Using Digital Image Speckle Correlation", Skin Res. Technol., vol. 14, 2008, pp. 298-303.

Non-Final Office Action received for U.S. Appl. No. 13/691,656, dated Jul. 2, 2015, 8 pages.

Final Office Action dated Jun. 15, 2017, by The United States Patent and Trademark Office for U.S. Appl. No. 13/691,656, filed Nov. 30, 2012, 7 pages.

Final Office Action received for U.S. Appl. No. 13/691,656, dated Mar. 11, 2016.

Non-Final Office Action issued by The United States Patent and Trademark Office for U.S. Appl. No. 13/691,656, dated Sep. 8, 2016, 8 pages.

Final Office Action issued by the United States Patent and Trademark Office for U.S. Appl. No. 13/789,512, dated Nov. 1, 2017, 16 pages.

(56) References Cited

OTHER PUBLICATIONS

Notice of Allowance received for U.S. Appl. No. 13/691,656, dated Jul. 24, 2017, 8 pages.
International Search Report and Written Opinion dated Apr. 23, 2013 for PCT Application No. PCT/US2013/25449, filed on Feb. 8, 2013, 8 pages.
Non-Final Office Action issued by the United States Patent and Trademark Office for U.S. Appl. No. 13/789,512, dated Feb. 16, 2017, 16 pages.
Non-Final Action received for U.S. Appl. No. 14/158,688, date May 18, 2016, 6 pages.
Advisory Action received for U.S. Appl. No. 13/029,023, dated Feb. 4, 2014, 4 pages.
Notice of Allowance received for U.S. Appl. No. 13/029,023, dated Feb. 12, 2016, 9 pages.
Notice of Allowance received for U.S. Appl. No. 13/189,105, dated Nov. 20, 2015, 5 pages.
Final Office action received for U.S. Appl. No. 13/411,394, dated Feb. 1, 2016, 14 pages.
Non-Final Office received for U.S. Appl. No. 13/411,443, dated Jan. 13, 2016, 14 pages.
Notice of Allowance received for U.S. Appl. No. 13/789,237, dated Nov. 24, 2015, 5 pages.
Extended European Search Report (includes Supplementary European Search Report and Search Opinion) received for European Patent Application No. 13825488.3, dated Feb. 23, 2016, 6 pages.
Non-Final Office Action received for U.S. Appl. No. 14/158,741, dated Dec. 16, 2015, 9 pages.
Extended European Search Report dated Jun. 29, 2015, for European Patent Application No. 12732236.0, 6 pages.
Extended European Search Report dated Oct. 1, 2014, for European Patent Application No. 12752239.9, 7 pages.
Final Office Action dated Nov. 25, 2013 for U.S. Appl. No. 13/029,023, 12 pages.
Non Final Office Action received for U.S. Appl. No. 13/029,023, dated Jun. 10, 2015, 12 pages.
Non-Final Office Action received for U.S. Appl. No. 13/029,023, dated Aug. 14, 2014, 12 pages.
Non Final Office Action received for U.S. Appl. No. 13/089,105, dated Dec. 5, 2013, 14 pages.
Non-Final Office Action received for U.S. Appl. No. 13/089,105 dated Jul. 10, 2014, 8 pages.
Non-Final Office Action received for U.S. Appl. No. 13/089,105, dated Apr. 10, 2015, 15 pages.
Non-Final Office Action received for U.S. Appl. No. 13/345,524, dated Apr. 10, 2015, 12 pages.
Non-Final Office Action received for U.S. Appl. No. 13/345,524, dated Mar. 28, 2014, 12 pages.
Notice of Allowance received for U.S. Appl. No. 13/345,524, dated Oct. 5, 2015, 9 pages.
Final Office Action received for U.S. Appl. No. 13/411,394, dated Mar. 18, 2014, 12 pages.
Non-Final Office Action received for U.S. Appl. No. 13/411,394, dated Apr. 10, 2015, 15 pages.
Final Office Action received for U.S. Appl. No. 13/411,443 dated Jun. 3, 2015, 13 pages.
Non-Final Office Action received for U.S. Appl. No. 13/411,443, dated Jan. 16, 2015, 12 pages.
Non Final Office Action received for U.S. Appl. No. 13/789,204, dated Oct. 8, 2014, 8 pages.
Final Office Action received for U.S. Appl. No. 13/789,229, dated Jan. 15, 2015, 21 pages.
Non-Final Office Action received for U.S. Appl. No. 13/789,229, dated Jun. 4, 2014, 6 pages.
Final Office Action received for U.S. Appl. No. 13/789,237, dated Aug. 27, 2015, 9 pages.
Non Final Office Action received for U.S. Appl. No. 13/789,237, dated Mar. 31, 2014, 5 pages.
Final Office Action received for U.S. Appl. No. 13/789,264, dated Jul. 16, 2015, 11 pages.

Non-Final Office Action received for U.S. Appl. No. 13/789,264, dated Mar. 26, 2014, 10 pages.
Brace, "Definition of Brace," Merriam Webster, Available at <www.merriam-webster.com>, 2015, 4 pages.
Mask, "Definition of Mask," Merriam Webster, Available online at <www.merriam-webster.com>, 2015, 4 pages.
Advisory Action received for U.S. Appl. No. 13/789,264, dated Oct. 19, 2015, 3 pages.
Advisory Action received for U.S. Appl. No. 13/789,237, dated Oct. 8, 2015, 5 pages.
"NHSSB Wound Management Manual," Northern Health and Social Services Board pp. 1-97 (2005).
Shanghai Dongyue Medical Health Product Co., Ltd., "Silicon-Gel Membrane-Scar Bandage," available online at <http://www.shdongyue.com/cp/shaos/shaos02b.asp>, last visited on Nov. 6, 2008, 2 pages.
Extended European Search Report and European Search Opinion dated Aug. 19, 2013, for European Patent Application No. 10808724.8, 8 pages.
Non Final Office Action received for U.S. Appl. No. 11/888,978, dated Apr. 13, 2009, 21 pages.
Notice of Allowance received for U.S. Appl. No. 11/888,978, dated Jan. 19, 2010, 8 pages.
Non Final Office Action received for U.S. Appl. No. 12/358,159, dated Mar. 7, 2011, 15 pages.
Notice of Allowance received for U.S. Appl. No. 12/358,159, dated Oct. 11, 2011, 5 pages.
Non Final Office Action received for U.S. Appl. No. 12/358,162, dated Aug. 5, 2011, 14 pages.
Notice of Allowance received for U.S. Appl. No. 12/358,162, dated Dec. 29, 2011, 8 pages.
Notice of Allowance received for U.S. Appl. No. 12/358,162, dated Mar. 2, 2012, 8 pages.
Non Final Office Action received for U.S. Appl. No. 12/358,164, dated Aug. 5, 2011, 16 pages.
Notice of Allowance received for U.S. Appl. No. 12/358,164, dated Dec. 29, 2011, 7 pages.
Notice of Allowance received for U.S. Appl. No. 12/358,164, dated Feb. 17, 2012, 8 pages.
Non Final Office Action received for U.S. Appl. No. 12/854,859, dated Mar. 29, 2013, 11 pages.
Notice of Allowance received for U.S. Appl. No. 12/854,859, dated Oct. 9, 2013, 7 pages.
Non Final Office Action received for U.S. Appl. No. 13/029,023, dated Mar. 15, 2013, 9 pages.
Non Final Office Action received for U.S. Appl. No. 13/089,104, dated Aug. 8, 2012, 14 pages.
Notice of Allowance received for U.S. Appl. No. 13/089,104, dated Jan. 8, 2013, 9 pages.
Final Office Action received for U.S. Appl. No. 13/089,105, dated May 23, 2013, 14 pages.
Non Final Office Action received for U.S. Appl. No. 13/089,105, dated Jul. 20, 2012, 18 pages.
Non Final Office Action received for U.S. Appl. No. 13/089,129, dated Jun. 28, 2013, 11 pages.
Notice of Allowance received for U.S. Appl. No. 13/089,129, dated Oct. 28, 2013, 7 pages.
Corrected Notice of Allowance received for U.S. Appl. No. 13/315,214, dated Jan. 23, 2013, 2 pages.
Non Final Office Action received for U.S. Appl. No. 13/315,214, dated Aug. 21, 2012, 6 pages.
Non Final Office Action received for U.S. Appl. No. 13/315,214, dated May 9, 2012, 7 pages.
Notice of Allowance received for U.S. Appl. No. 13/315,214, dated Dec. 10, 2012, 9 pages.
Non Final Office Action received for U.S. Appl. No. 13/411,394, dated Aug. 29, 2013, 16 pages.
3M Healthcare., "3MTM Steri-StripTM S Surgical Skin Closure," 3M HealthCare, St. Paul, MN, 1 page (undated).
3M Healthcare, "3MTM Steri-Strip TM Adhesive Skin Closures (Reinforced): Commonly Asked Questions," 3M HealthCare: St. Paul, MN, Jun. 27, 2002, pp. 1-4.

(56) References Cited

OTHER PUBLICATIONS

3M Healthcare, "3MTM Steri-Strip TM S Surgical Skin Closure, Poster of Available Sizes," 3M HealthCare, St. Paul, MN, 3 pages (undated).
3M Healthcare, "3M TM Steri-Strip TM S Surgical Skin Closure Application Instructions," 3M HealthCare, St. Paul, MN, 2007, 2 pages.
3M Healthcare, "3M TM Steri-StripTM S Surgical Skin Closure The Simple, Non-Invase Alternative to Staples and Sutures from the Steri-Strip Family," 3M HealthCare, St. Paul, MN, 2006, 2 pages.
3M Healthcare, "3MTM Steri-StripTM S Surgical Skin Closure: Commonly Asked Questions," 3M HealthCare, St. Paul, MN, Oct. 19, 2006, pp. 1-8.
3M Healthcare, "Reducing the Risk of Superficial Skin Damage Related to Adhesive Use," 3M HealthCare, St. Paul, MN, 2001, 2 pages.
3M Healthcare, "Tips for Trouble-Free Taping," 3M HealthCare, St. Paul, MN, May 2004, 4 pages.
3M Healthcare, "Steri-Strip: Skin Closures," Product Insert, 3M HealthCare, St. Paul, MN, 2003, 1 page.
3M Healthcare, "They Say Every Scar Tells a Story," 3M HealthCare, St. Paul, MN, 2006, 1 page.
3M Healthcare, "3MTM Steri-StripTM S Surgical Skin Closure Application Examples, Comparisons and Results," 3M HealthCare, St. Paul, MN, 2007, 4 pages.
3M Healthcare, "3MTM Steri-StripTM S Surgical Skin Closure, Patient Care Informaton ," 3M HealthCare, St. Paul, MN, 2006, 2 pages.
Aarabi et al., "Mechanical Load Initiates Hypertrophic Scar Formation Through Decreased Cellular Apoptosis," The FASEB Journal, vol. 21, Oct. 2007, pp. 3250-3261.
Al-Attar et al., "Keloid Pathogenesis and Treatment," Plastic and Reconstructive Surgery, vol. 117, No. 1, Jan. 2006, pp. 286-300.
Angelini et al., "Comparative Study of Leg Wound Skin Closure in Coronary Artery Bypass Graft Operations," Thorax, vol. 39, 1984, pp. 942-945.
Anonymous, "3MTM Steri-StripTM Adhesive Skin Closures," 3M Brochure, 2003, 12 pages.
Anonymous, "3MTM Tegaderm TM Family of Transparent Dressings," 3M Brochure, 2005, 6 pages.
Anonymous, "Avocet Polymet Technologies Inc.," available at<http://www.avocetcorp.com/index.html>, last visited Nov. 5, 2007, 1 page.
Anonymous, "Avogel Scar Hydrogel," available at <http://www.avocetcorp.com/avogel_scar_hydrogel.html>, last visited Nov. 5, 2007, 2 pages.
Anonymous, "Avosil Ointment," available at <http://www.avocetcorp.com/avosil.html>, last visited Nov. 5, 2007, 3 pages.
Anonymous, "Mepiform Instructions of Use," Tendra Corporation Brochure, 2 pages (undated).
Anonymous, "Silicone Scar Bandage: Standard Wound Healing Application," available at <http://www.thejamushop.com/silicon_sheet_for_keloids.htm>, last visited on Mar. 18, 2009, 4 pages.
Atkinson et al., "A Randomized, Controlled Trial to Determine the Efficacy of Paper Tape in Preventing Hypertrophic Scar Formation in Surgical Incisions that Traverse Langer's Skin Tension Lines," Plastic and Reconstructive Surgery, vol. 116, No. 6, Nov. 2005, pp. 1648-1656.
Bachert et al., "Probing Elastic Modulus and Depth of a Two Layer Human Skin Model with Piezoelectric Cantilevers," Biomedical Engineering Senior Design Team, Drexel University, 2003, pp. 1-27.
Berman et al., "Keloid and Hypertrophic Scar," available at <http://www.emedicine.com/DERM/topic205.htm> last visited on Nov. 19, 2007, 23 pages.
Bunker, Timothy D., "Problems with the Use of Op-Site Sutureless Skin Closures in Orthopaedic Procedures," Annals of the Royal College of Surgeons of England, vol. 65, 1983, pp. 260-262.
Burd et al., "Hypertrophic Response and Keloid Diathesis: Two Very Different Forms of Scar," Plastic and Reconstructive Surgery, vol. 116, No. 7, Dec. 2005, pp. 150e-157e.
Canica Design Inc, "ABRA® Abdominal Wall Closure Set: Aa Dynamic Wound Closure System," Instructions for Use, available online at<http://www.canica.com/instructions/1D1544%20ABRA%20CWK08.pdf>, last visited on Sep. 10, 2009, pp. 1-11.
Canica Design Inc., "ABRA® Surgical Skin Closure Set: A Dynamic Wound Closure System," available online at <http://www.canica.com/instructions/1D0830.pdf>, last visited on Sep. 10, 2009, pp. 1-4.
Chen et al., "Prospective Study Comparing Wounds Closed With Tape With Sutured Wounds in Colorectal Surgery," Arch.Surg., vol. 136, Jul. 2001, pp. 801-803.
Davison et al., "Ineffective Treatment of Keloids with Interferon Alpha-2b," Plastic and Reconstructive Surgery, vol. 117, No. 1, Jan. 2006, pp. 247-252.
Escoffier et al., "Age-Related Mechanical Properties of Human Skin: An in Vivo Study," The Journal of Investigate Dermatology, vol. 93, No. 3, Sep. 1989, pp. 353-357.
Evans et al., "Measuring the Mechanical Properties of Human Skin in vivo Using Digital Image Correlation and Finite Element Modelling," J. Strain Analysis, vol. 44, 2009, pp. 337-345.
Fairclough et al., "The Use of Sterile Adhesive Tape in the Closure of Arthroscopic Puncture Wounds: A Comparison with a Single Layer Nylon Closu," Annals of the Royal College of Surgeons of England, vol. 69, 1987, pp. 140-141.
Gorney, Mark , "Scar: The Trigger to the Claim," Plastic and Reconstructive Surgery. vol. 117, No. 3, Mar. 2006, pp. 1036-1037.
Hof et al., "Comparing Silicone Pressure-Sensitive Adhesives to Silicone Gels for Transdermal Drug Delivery," Presented at 33 Annual Meeting and Exposition to the Controlled Release Society, Vienna, Austria, Jul. 22-26, 2006, 7 pages.
Koval et al., "Tape Blisters Following Hip Surgery. A Prospective Randomized Study of Two Types of Tape," The Journal of Bone and Joint Surgery, vol. 85-A, No. 10, Oct. 2003, pp. 1884-1887.
Kuo et al., "Prospective, Randomized, Blinded Study of a New Wound Closure Film Versus Cutaneous Suture for Surgical Wound Closure," Dermatologic Surgery, vol. 32, No. 5, May 2006, pp. 676-681.
Mustoe et al., "A Randomized, Controlled Trial to Determine the Efficacy of Paper Tape in Preventing Hypertrophic Scar Formation in Surgical Incisions that Traverse Langer's Skin Tension Lines," Plastic and Reconstructive Surgery (Discussion) vol. 116, No. 6, Nov. 2005, pp. 1657-1658.
Nahabedian, Maurice Y., "Scar Wars: Optimizing Outcomes with Reduction Mammaplasty," Plastic and Reconstructive Surgery, vol. 116, No. 7, Dec. 2005, pp. 2026-2029.
O'Brien et al., "Silicon Gel Sheeting for Preventing and Treating Hypertrophic and Keloid Scars (Review)," The Cochrane Collaboration, 2009, pp. 1-47.
International Search Report and Written Opinion received for PCT Patent Application No. PCT/US2007/017320, dated Feb. 7, 2008, 10 pages.
International Search Report and Written Opinion received for PCT Patent Application No. PCT/US2010/045239, dated Feb. 8, 2011, 12 pages.
International Search Report and Written Opinion received for PCT Patent Application No. PCT/US2012/020561, dated May 1, 2012, 9 pages.
International Search Report and Written Opinion received for PCT Patent Application No. PCT/US2012/025510, dated May 29, 2012, 11 pages.
International Search Report and Written Opinion received for PCT Patent Application No. PCT/US2012/027618, dated Jun. 28, 2012, 12 pages.
Pitcher, David, "Sutureless Skin Closure for Pacemaker Implantation: Comparison with Subcuticular Suture," Postgraduate Medical Journal, vol. 59, Feb. 1983, pp. 83-85.
Shirado et al., "Realization of Human Skin-Like Texture by Emulating Surface Shape Pattern and Elastic Structure," presented at

(56) References Cited

OTHER PUBLICATIONS

Symposium on Haptic Interfaces for Virtual Environment and Teleoperator Systems 2006, Mar. 25-26, 2006, Alexandria, VA, pp. 295-296.

Smith & Nephew, "CICA-CARE. Silicone Gel Sheeting," available online at <http://wound.smith-nephew.com/za/Product.asp?NodeId=569&Tab=5&Hide=True>, last visited on Jun. 9, 2009, 1 page.

Sullivan et al., "Acute Wound Care" Chapter 7 in ACS Surgery: Principles and Practice, 2007, pp. 1-24.

Teot, Luc, "Scar Evaluation and Management: Recommandations," European Tissue Repair Society, Scar Control I, ETRS-Bulletin 12.1 & 2, available online at <http://www.etrs.org/bullefin12_1/secfion11.php>, last visited on Nov. 30, 2007, 13 pages.

Vaughan et al., "Optimal Closure of Surgical Wounds in Forefoot Surgery: Are Adhesive Strips Beneficial?," Acta Orthop. Belg. vol. 72, No. 6, 2006, pp. 731-733.

Vowden, Kathryn, "Wound Management. Policy and Resource Pack," Bradford Teaching Hospitals NHS Foundation Trust, Mar. 2003, pp. 1-72.

Watson et al., "Op-Site Skin Closure: A Comparison with Subcuticular and Interrupted Sutures," Annals of the Royal College of Surgeons of England, vol. 65, 1983, pp. 83-84.

Webster et al., "Closure of Abdominal Wounds by Adhesive Strips: A Clinical Trial," British Medical Journal, vol. 20, Sep. 20, 1975, pp. 696-697.

Westaby, S., "Evaluation of a New Product for Sutureless Skin Closure," Annals of the Royal College of Surgeons of England, vol. 62, 1980, pp. 129-132.

Wound Care Technologies, "DERMACloseTM RC: Continuous External Tissue Expander," available at< http://www.woundcaretech.com/sell-sheet.pdf>, last visited on Sep. 10, 2009, 2008, 2 pages.

Wound Care Technologies, "Instructions for Use. DERMACloseTM RC," available at <http://www.dermaclose.com/instructions.pdf>, last visited on Sep. 10, 2009, 2008, 2 pages.

\* cited by examiner

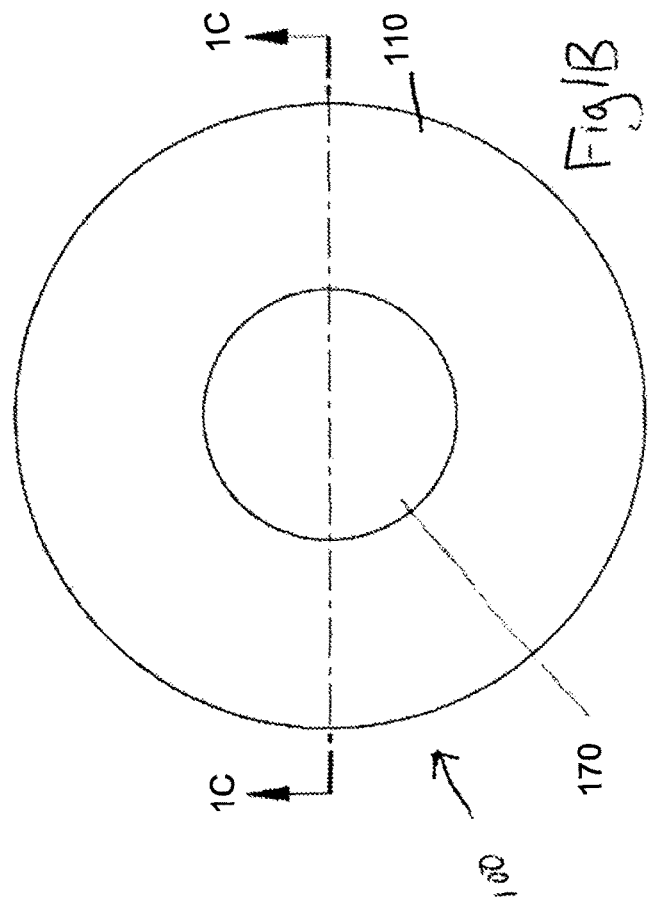
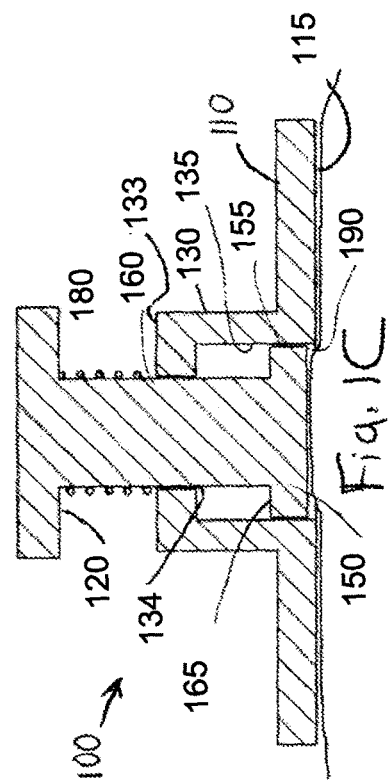
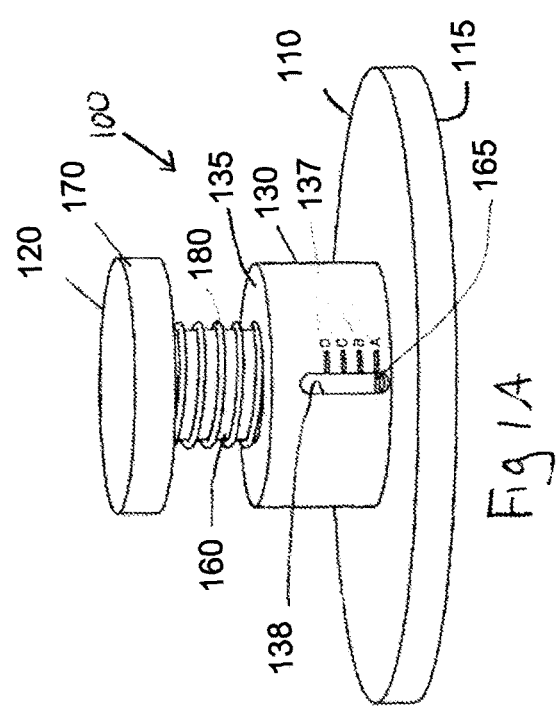

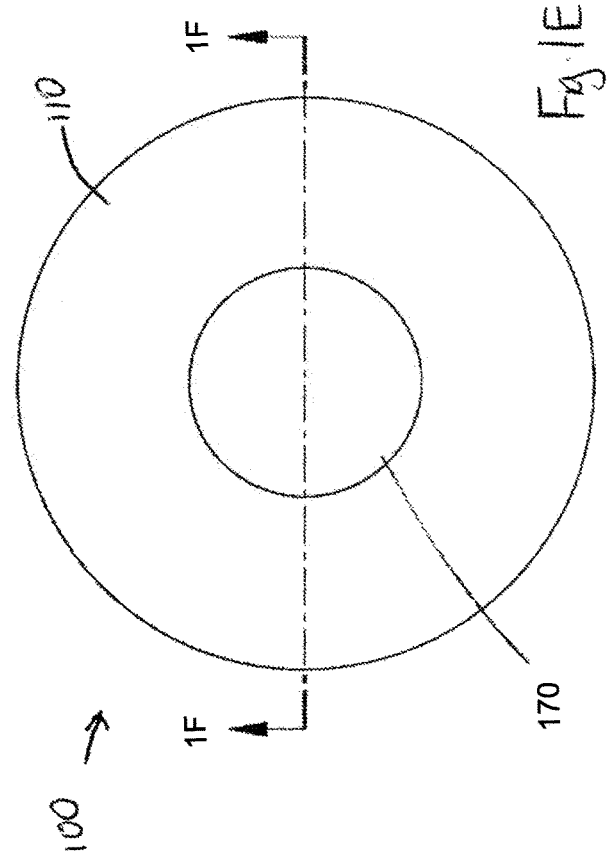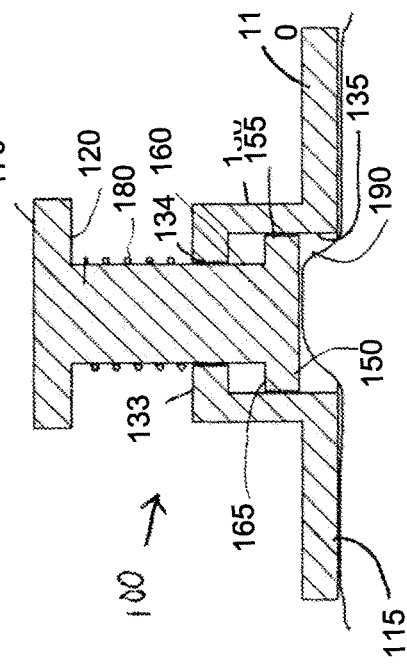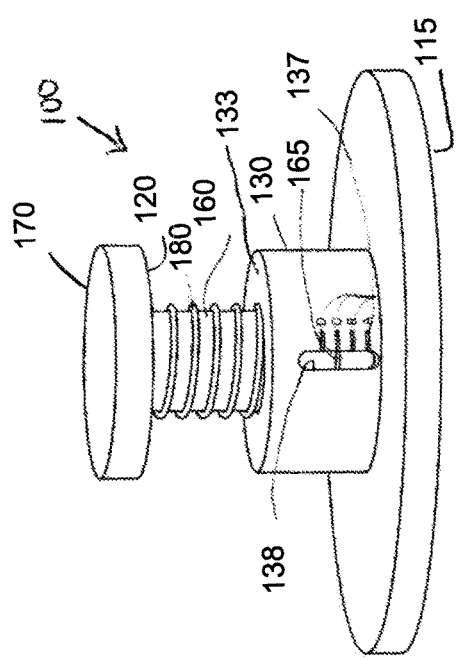

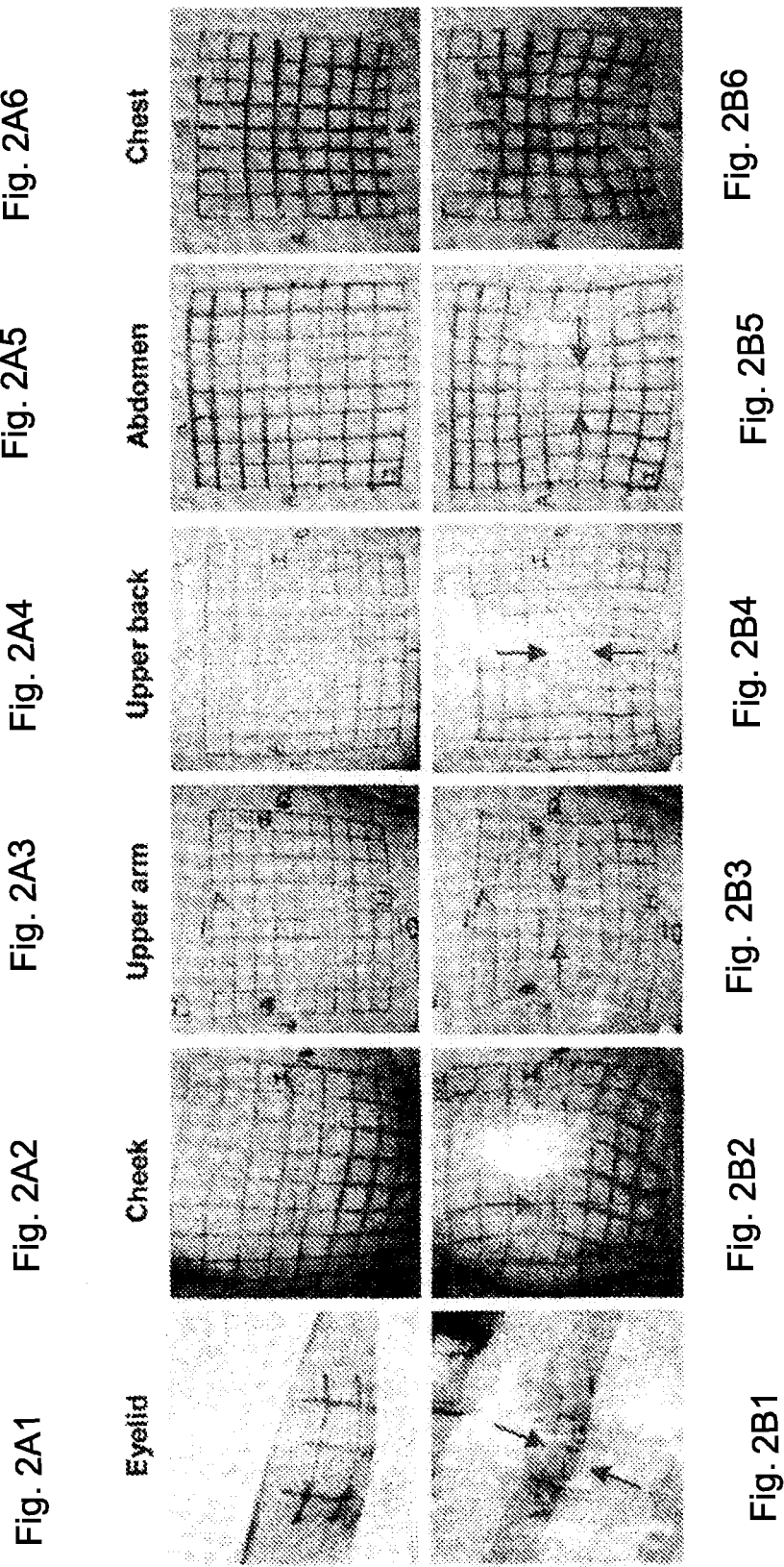

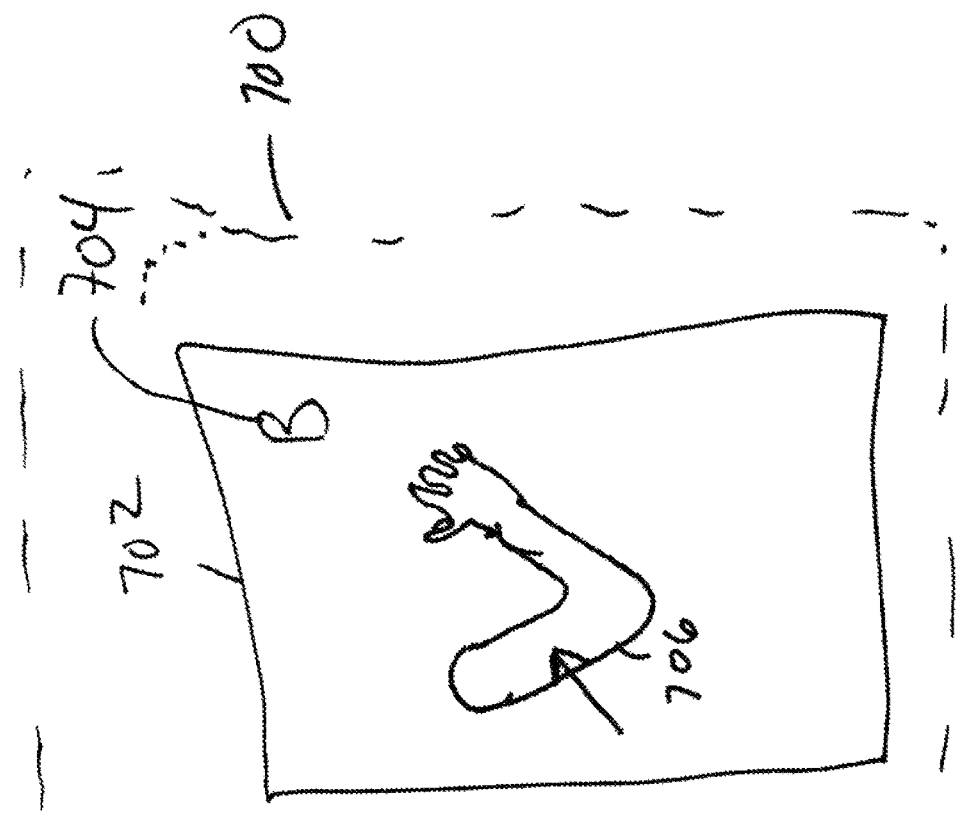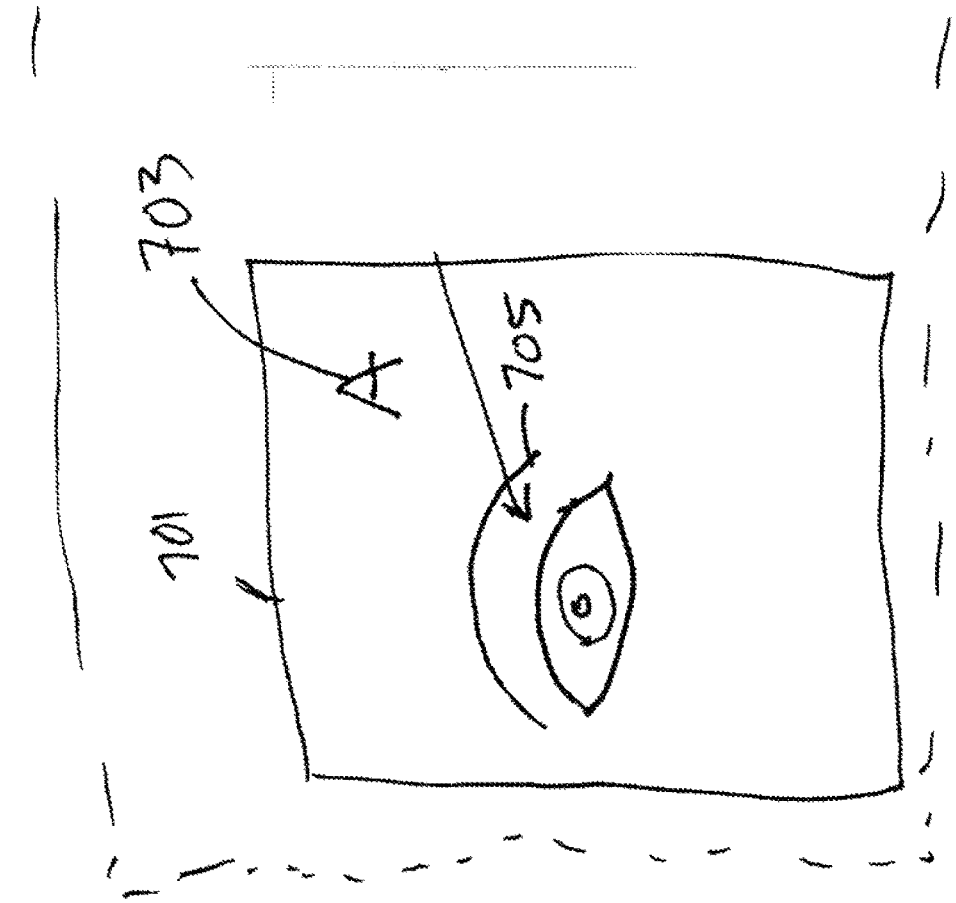
Fig 7

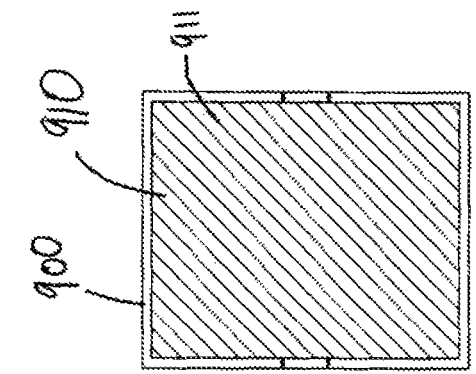
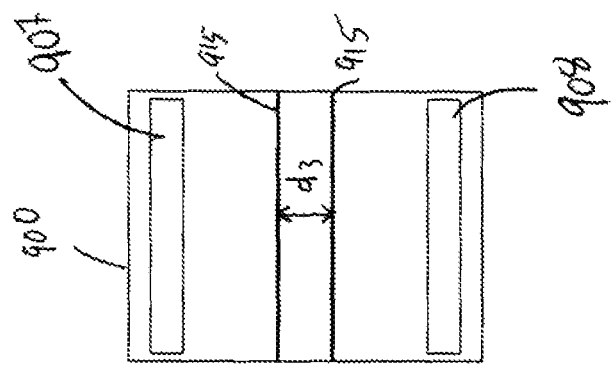
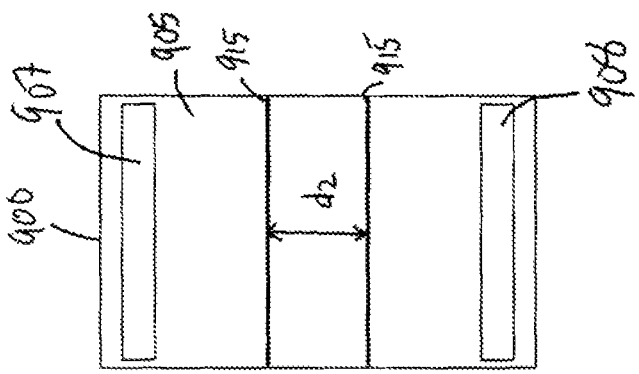
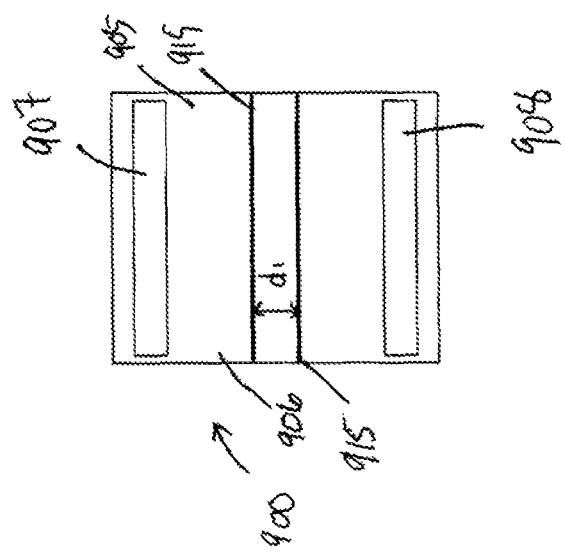

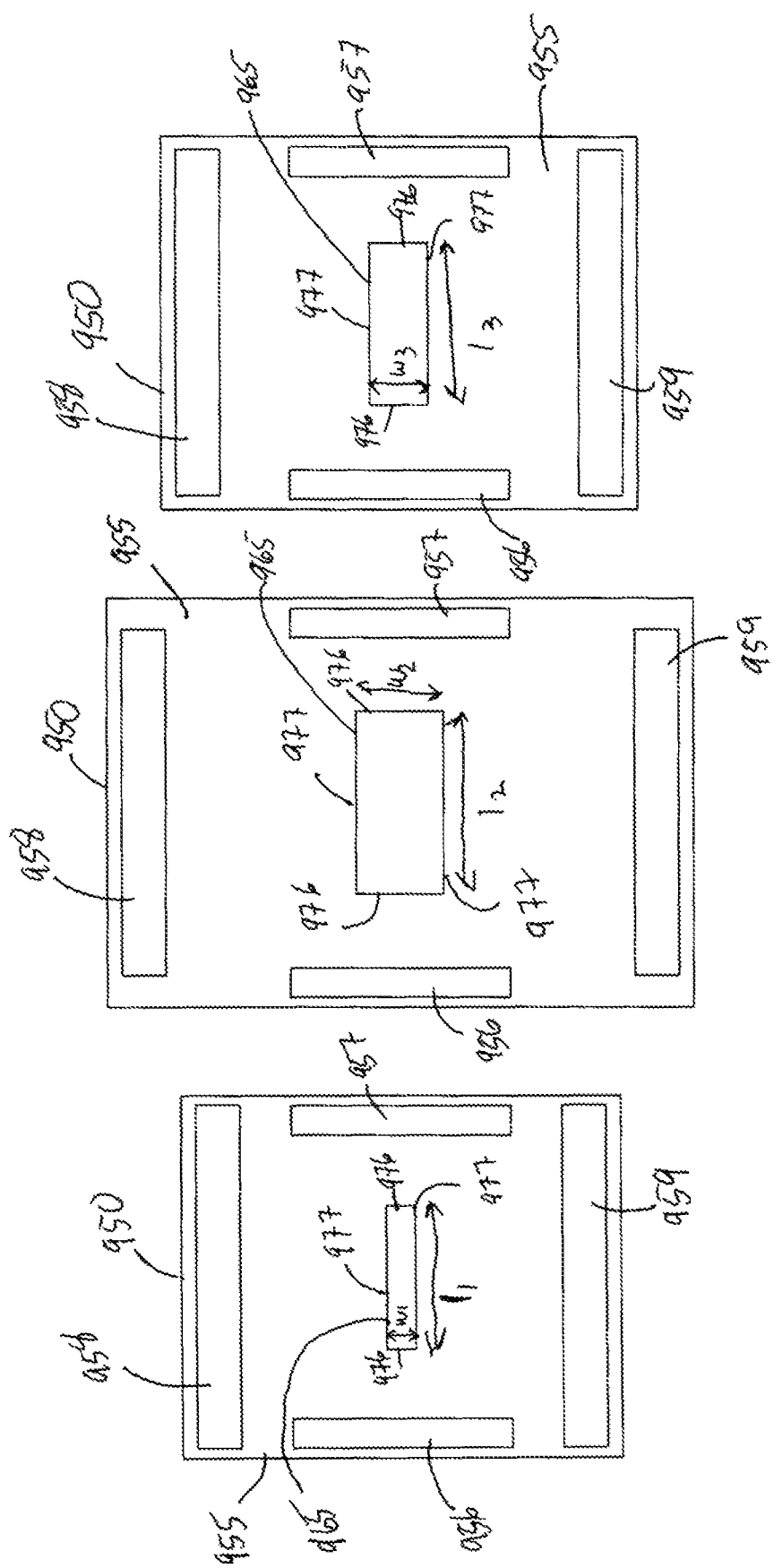

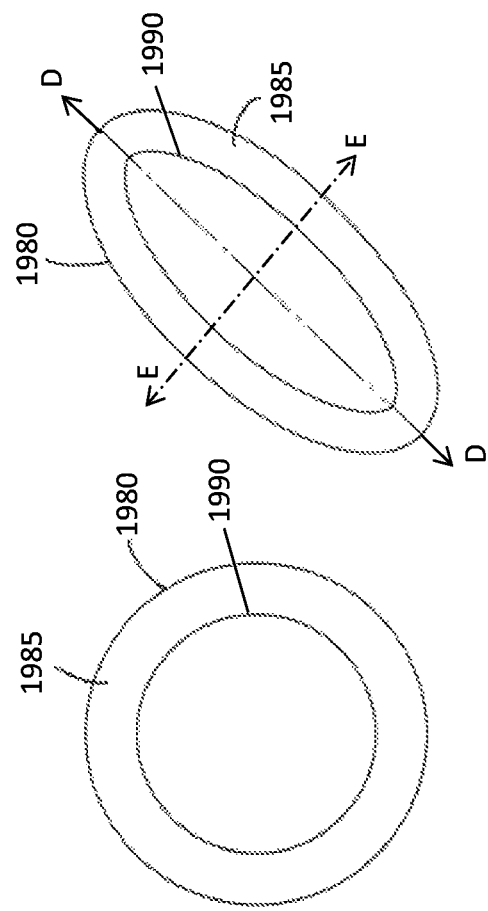
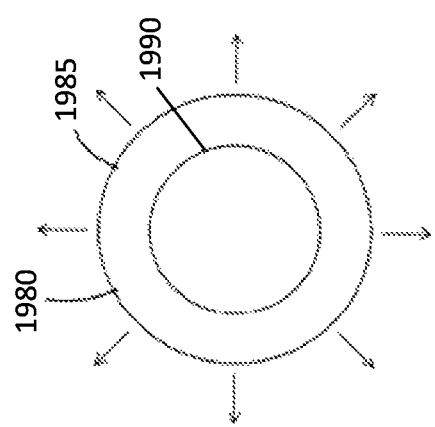
FIG. 13C
FIG. 13B
FIG. 13A

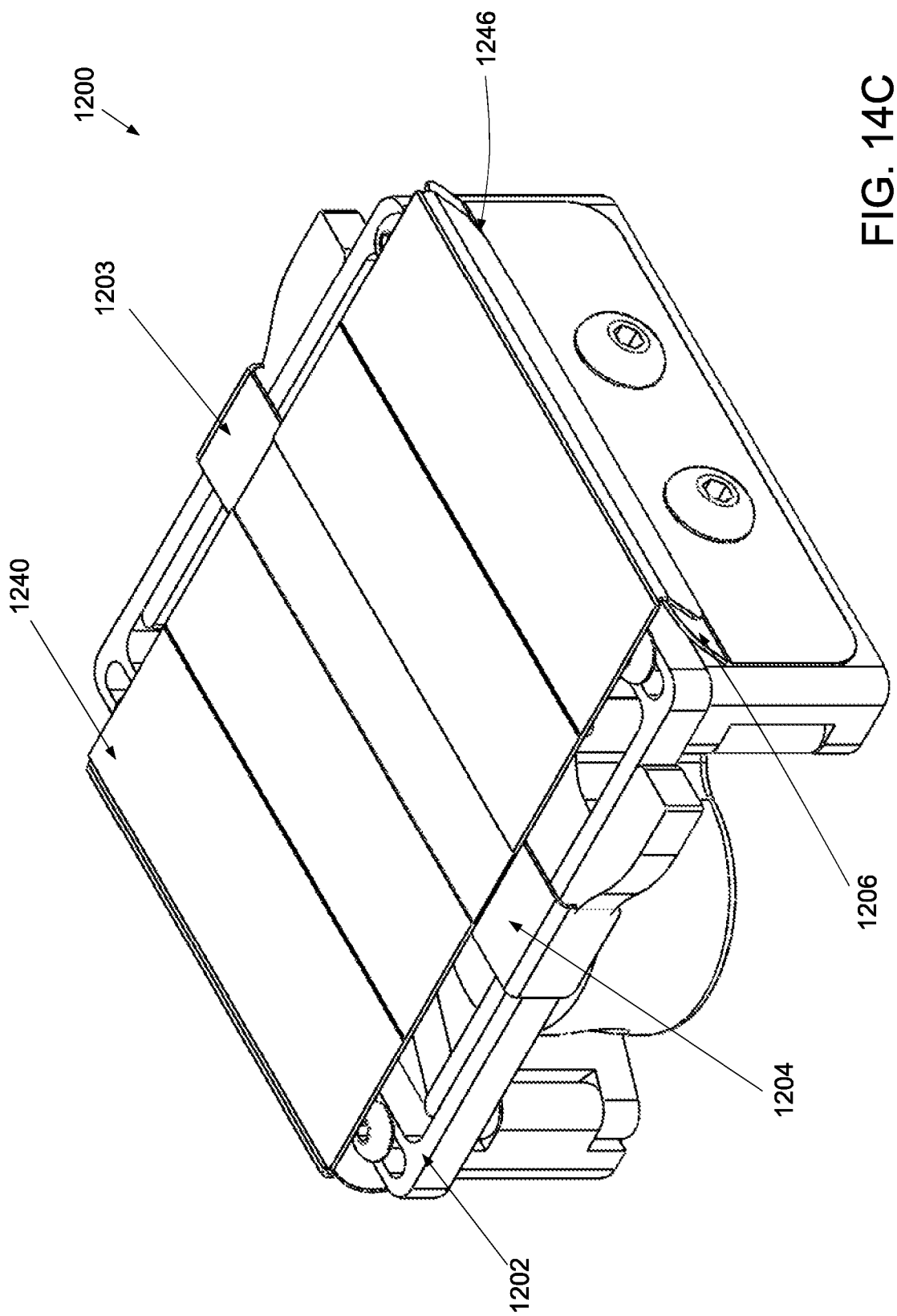

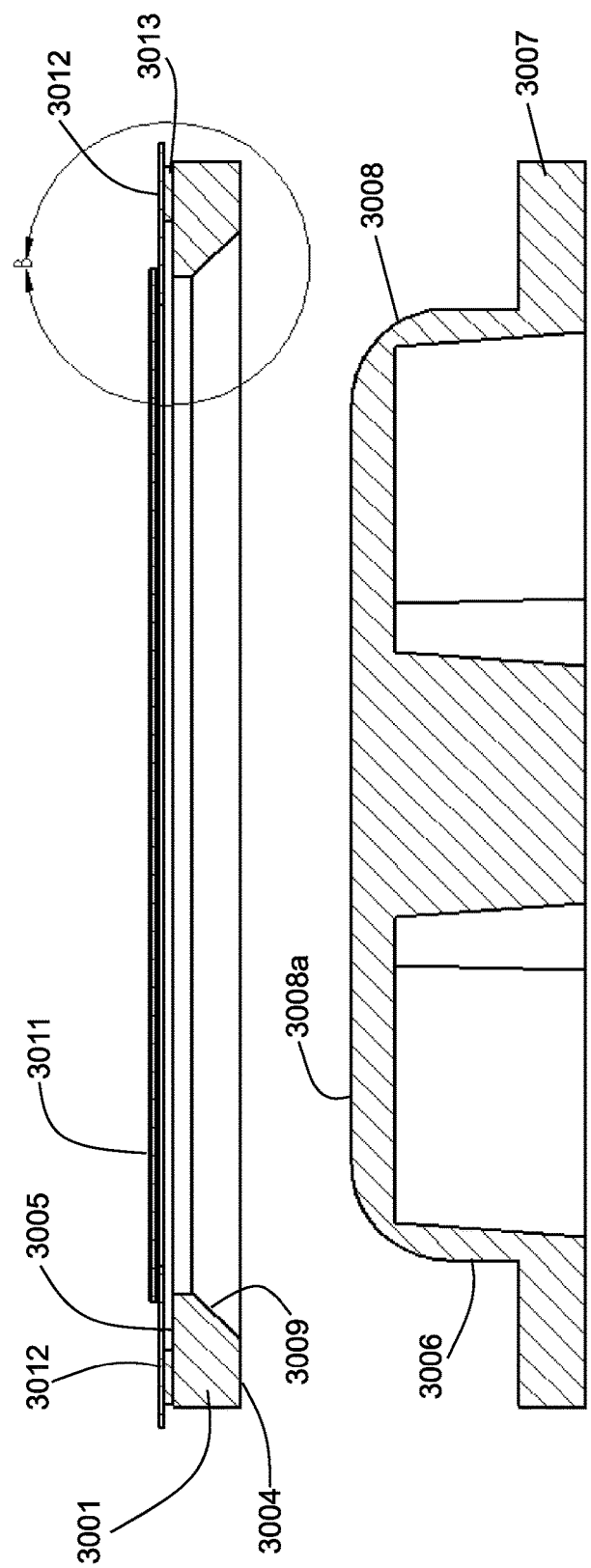
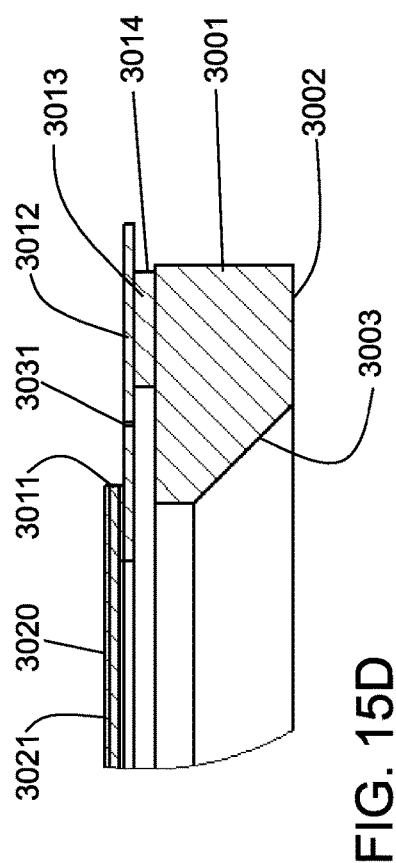
FIG. 15C
FIG. 15D

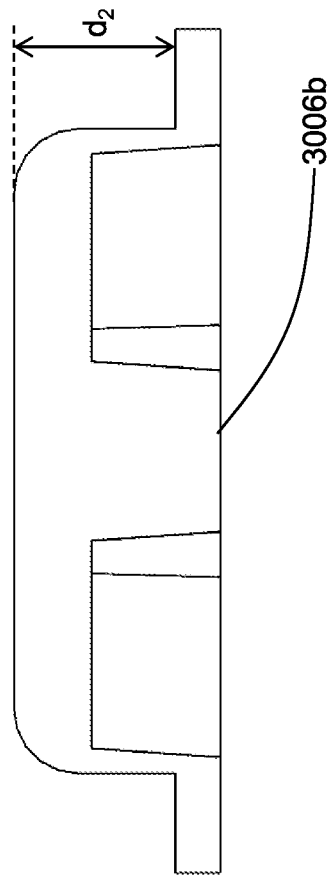
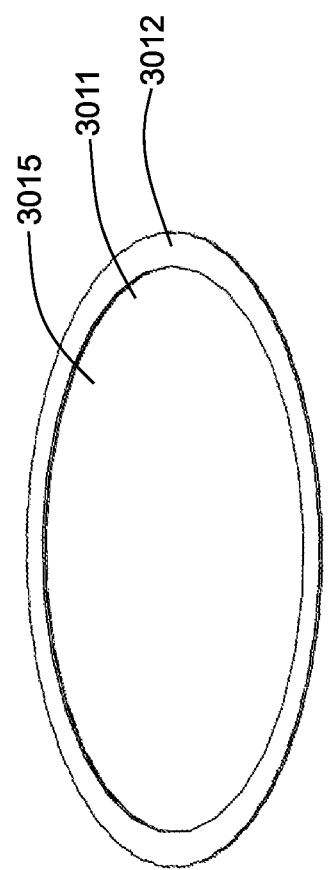

ELASTIC DEVICES, METHODS, SYSTEMS AND KITS FOR SELECTING SKIN TREATMENT DEVICES

CROSS-REFERENCE TO RELATED APPLICATIONS

This application is a Continuation-in-Part of U.S. application Ser. No. 13/691,656, filed on Nov. 30, 2012, which claims the benefit of 35 U.S.C. § 119(e) to U.S. Provisional Application Ser. No. 61/566,590, filed on Dec. 2, 2011, which is hereby incorporated by reference in its entirety. This application is also related to U.S. application Ser. No. 11/888,978, now U.S. Pat. No. 7,683,234, filed on Aug. 3, 2007; U.S. application Ser. No. 12/358,159, now U.S. Pat. No. 8,063,263, filed on Jan. 22, 2009; U.S. application Ser. No. 12/358,162, now U.S. Pat. No. 8,168,850, filed Jan. 22, 2009; U.S. application Ser. No. 12/358,164, now U.S. Pat. No. 8,183,428, filed Jan. 22, 2009; U.S. application Ser. No. 13/089,104, filed Apr. 18, 2011; U.S. application Ser. No. 13/089,105, filed Apr. 18, 2011; U.S. application Ser. No. 12/854,859, filed Aug. 11, 2010; U.S. application Ser. No. 13/089,129, filed Apr. 18, 2011; U.S. application Ser. No. 13/315,214, filed Dec. 8, 2011; and U.S. application Ser. No. 13/029,023, filed Feb. 16, 2011.

FIELD

The claimed invention relates to devices, methods, systems and/or kits for selecting skin treatment methods, devices or device properties based on skin properties.

BACKGROUND

Scar formation in response to cutaneous injury is part of the natural wound healing process. Wound healing is a lengthy and continuous process, although it is typically recognized as occurring in stages. The process begins immediately after injury, with an inflammatory stage. During this stage, which typically lasts from two days to one week (depending on the wound), damaged tissues and foreign matter are removed from the wound. The proliferative stage occurs at a time after the inflammatory stage and is characterized by fibroblast proliferation and collagen and proteoglycan production. It is during the proliferative stage that the extracellular matrix is synthesized in order to provide structural integrity to the wound. The proliferative stage usually lasts about four days to several weeks, depending on the nature of the wound, and it is during this stage when hypertrophic scars usually form. The last stage is called the remodeling stage. During the remodeling stage the previously constructed and randomly organized matrix is remodeled into an organized structure that is highly cross-linked and aligned to increase mechanical strength.

While the histological features characterizing hypertrophic scars have been well documented, the underlying pathophysiology is not well known. Hypertrophic scars are a side effect of excessive wound healing, and generally result in the overproduction of cells, collagen, and proteoglycans. Typically, these scars are raised and are characterized by the random distribution of tissue bundles. The appearance (i.e., size, shape, and color) of these scars varies depending on the part of the body in which they form, and the underlying ethnicity of the person affected. Hypertrophic scars are very common, and may occur following any full thickness injury to the skin. Recently, it has been shown in U.S. Patent Application Publication 2006/0037091 (U.S. patent application Ser. No. 11/135,992 entitled "Method for Producing Hypertrophic Scarring Animal Model for Identification of Agents for Prevention and Treatment of Human Hypertrophic Scarring," filed May 24, 2005) which is hereby incorporated by reference in its entirety, that mechanical stress may increase hypertrophic scarring in a murine model.

Keloids are typically characterized as tumors consisting of highly hyperplastic masses that occur in the dermis and adjacent subcutaneous tissue in susceptible individuals, most commonly following trauma. Keloids are often more severe than hypertrophic scars, since they tend to invade normal adjacent tissue, while hypertrophic scars tend to remain confined within the original scar border.

BRIEF SUMMARY

According to variations, a system is provided for identifying a skin direction of greater inherent skin tension at a location in a subject comprising: an elastic sheet of material and a skin adhesive; wherein the elastic sheet is configured to be strained a desired amount; wherein the elastic sheet comprises at least a first and second configuration wherein in the first configuration, the elastic sheet is strained, wherein the elastic sheet is configured to be removably secured to a skin surface with the skin adhesive while in the first configuration and is configured to be released from the first configuration when adhered to a epidermal layer skin to adopt to the second configuration; and a skin tension indicator configured to indicate a direction of a relatively greater inherent skin tension when the elastic sheet adhered to an epidermal layer of skin in the second configuration.

The skin tension indicator may comprise a marking to the elastic sheet. The marking may be symmetric in the first configuration and asymmetric in the second configuration. The marking may comprise a portion that is elongated in the second configuration with respect to a length in the first configuration. The marking may be but is not limited to a printed image or an embedded marker. The marking may be but is not limited to a circle or a plurality of radially intersecting lines. The skin tension indicator may also comprise a cutout of the elastic sheet. The elastic sheet may be arcuate, circular, rectangular or any other shape. The elastic sheet further comprises an attachment structure configured to releasably couple a tensioning device configured to strain the elastic sheet. The attachment structure may be configured to be used to uniaxially, multiaxially or radially strain the elastic sheet.

According to variations system for determining a relative inherent skin tension at a location in a subject may comprise an elastic sheet of material and a skin adhesive; wherein the elastic sheet is configured to be strained a desired amount; wherein the elastic sheet comprises at least a first and second configuration wherein in the first configuration, the elastic sheet is strained, wherein the elastic sheet is configured to be removably secured to a skin surface with the skin adhesive while in the first configuration and is configured to be released from the first configuration when adhered to a epidermal layer skin to adopt to the second configuration; and a skin tension indicator configured to indicate a relative amount of inherent skin tension when the elastic sheet adhered to an epidermal layer of skin in the second configuration. The system may further comprise a plurality of skin treatment devices wherein each of the plurality of skin treatment devices has a different mechanical property from the other of the plurality of skin treatment devices; and wherein the skin tension indicator comprises a plurality of orientations configured to indicate one of the plurality of skin treatment devices. The skin tension indicator may comprise at least one marking to the elastic sheet. The marking may comprise a portion that is elongated in the second configuration with respect to a length in the first configuration. The skin tension indicator may comprise a cutout of the elastic sheet. The elastic sheet may further comprise an attachment structure configured to releasably couple to a tensioning device configured to strain the elastic sheet. The attachment structure may be configured to be used to uniaxially, multiaxially or radially strain the elastic sheet.

According to variations, a method may be provided for treating a subject comprising: identifying a location on a body of a subject for deployment of a skin treatment device; selecting a skin treatment device from a plurality of skin treatment devices wherein each of the plurality of skin treatment devices has a different mechanical property and is associated for use with a body region; and attaching the skin treatment device in the initial strained configuration to the treatment site. According to a variation, each of the plurality of skin treatment devices associated for use with a body region may be packaged with a label indicating the body region. According to a variation, the label may graphically indicate the body region.

According to variations, a method may be provided for selecting a skin treatment device for a subject based on one or more inherent skin properties, comprising: providing a skin interface element configured to apply a tension to skin of a subject; applying the tension to the skin of a subject; determining a skin mechanical property of a skin location of a subject; providing a plurality of skin treatment devices each of the plurality of devices comprising an elastic member and a securing member configured to couple the device to skin of a subject, wherein each of the plurality of skin treatment devices has a relaxed configuration and an initial strained configuration; wherein each of the plurality of skin devices has a different device mechanical property; and selecting one of the plurality of skin devices based at least in part on the determined skin mechanical property of the skin location; and attaching the skin device in the initial strained configuration to the skin of the subject. The step of applying tension may comprise applying a strained or tensioned elastic sheet having a relative tension indicator coupled to the sheet.

According to variations, a method of treating a subject is provided comprising: determining a skin mechanical property of a skin location of a subject; selecting an initial strain amount to be applied to a skin treatment device based on the location, wherein the skin treatment device comprises an elastic member configured to be stretched; and applying the initial strain amount to the skin treatment device; then applying the skin treatment device to the skin of a subject. According to variations, the skin mechanical property may comprise an inherent skin tension, a relative skin tension, skin stiffness, and/or a skin deformation property.

According to variations, a method is provided for treating a subject comprising: identifying a location on a body of a subject for deployment of a skin treatment device of a treatment site; selecting an initial strain amount to be applied to a skin treatment device based on the location, wherein the skin treatment device comprises an elastic member configured to be stretched; and applying the initial strain amount to the skin treatment device; then applying the skin treatment device to the skin of a subject. According to variations, the method may further comprise identifying one or more mechanical properties of a skin location for treatment.

According to variations, a system is provided for treating a subject comprising: a plurality of skin treatment devices wherein each of the plurality of skin treatment devices has a different mechanical property from the other of the plurality of skin treatment devices; and a skin property determining device configured to determine a skin mechanical property, wherein the skin property determining device comprises a plurality of indicators configured to indicate one of the plurality of skin treatment devices. According to variations, the skin property determining device may comprise an elastic sheet configured to determine a relative inherent skin tension.

According to variations a system is provided for treating a subject comprising: a skin treatment device comprising an elastic member wherein the elastic member has a relaxed configuration and a plurality of selectable strained configurations; and a skin tension device configured to determine a relative skin tension, wherein the skin tension device comprises an elastic sheet and a plurality of indicators configured to indicate one of the plurality selectable strained configurations.

According to variations, a system is provided for treating a subject comprising: a skin treatment device comprising an elastic member wherein the elastic member has a relaxed configuration and a plurality of selectable strained configurations; and a tensioning member configured to strain the skin treatment device to the plurality of selectable strained configurations, and an strain selector configured to indicate a selected one of the plurality of selectable strained configurations. The strain selector may be configured to indicate a strain for a particular region of the body.

According to variations a method may be provided for treating a subject with a skin treatment device comprising: stretching an elastic member from a relaxed configuration to an initial strained configuration, wherein the initial strained configuration is a predetermined amount of strain selected for a particular region of application to provide an approximate desired resulting load per width the skin location; and securing the elastic member to a skin location of a subject at the particular region to provide the approximate desired resulting load per width at the skin location. The approximate desired resulting load per width may be, for example, between about 2 and 5 N/m, between, between about 28 and 48 and/or between about 47 and 80 N/m.

BRIEF DESCRIPTION OF THE DRAWINGS

FIG. 1A is a perspective view of a skin strain measuring device in a first configuration in accordance with a variation of the invention.

FIG. 1B is a top view of the skin strain measuring device of FIG. 1A in the first configuration.

FIG. 1C is a side cross-sectional view of the skin strain measuring device of FIGS. 1A and 1B along the lines A-A.

FIG. 1D is a perspective view of a skin strain measuring device of FIG. 1A in a second skin tensioning configuration.

FIG. 1E is a top view of the skin strain measuring device of FIG. 1D in the second skin tensioning configuration.

FIG. 1F is a side cross-sectional view of the skin strain measuring device of FIGS. 1D and 1E along the lines B-B.

FIGS. 2A1 to 2A6 are photographs of grid lines applied to various regions of skin.

FIGS. 2B1 to 2B6 are photographs of the grid lines of the various regions of skin of FIGS. 2A1 to 2A6 after application of skin treatment device to a subject.

FIG. 6 is a graphical representation of estimated stress vs. strain values.

FIG. 7 is a schematic illustration of a plurality of labeled and packaged skin treatment devices.

FIG. 9A is a diagnostic elastic sheet in a first unstrained configuration; FIG. 9B is the diagnostic sheet of FIG. 9A in a strained configuration; FIG. 9C is the diagnostic sheet of FIG. 9B after it has been applied to a skin surface; FIG. 9D is a skin interfacing side of the diagnostic sheet of FIG. 9A.

FIG. 11A is a diagnostic elastic sheet in a first unstrained configuration; FIG. 11B is the diagnostic sheet of FIG. 11A in a strained configuration; FIG. 11C is the diagnostic sheet of FIG. 11B after it has been applied to a skin surface.

FIG. 13A is a diagnostic elastic sheet in a first unstrained configuration; FIG. 13B is the diagnostic sheet of FIG. 13A in a strained configuration; FIG. 13C is the diagnostic sheet of FIG. 13B after it has been applied to a skin surface.

FIG. 14C is an inferior perspective view of the applicator of FIG. 14A in an unstrained configuration.

FIG. 15C is a cross-sectional view of a strain plunger of the tensioning device and an assembled dressing assembly and frame of FIG. 15A along the lines A-A.

FIG. 15D is a detailed view of section B of FIG. 15C.

FIG. 15F illustrates a strain plunger.

FIG. 15G illustrates a strain plunger.

FIG. 15H illustrates an attachment ring.

DETAILED DESCRIPTION

Figure 3:
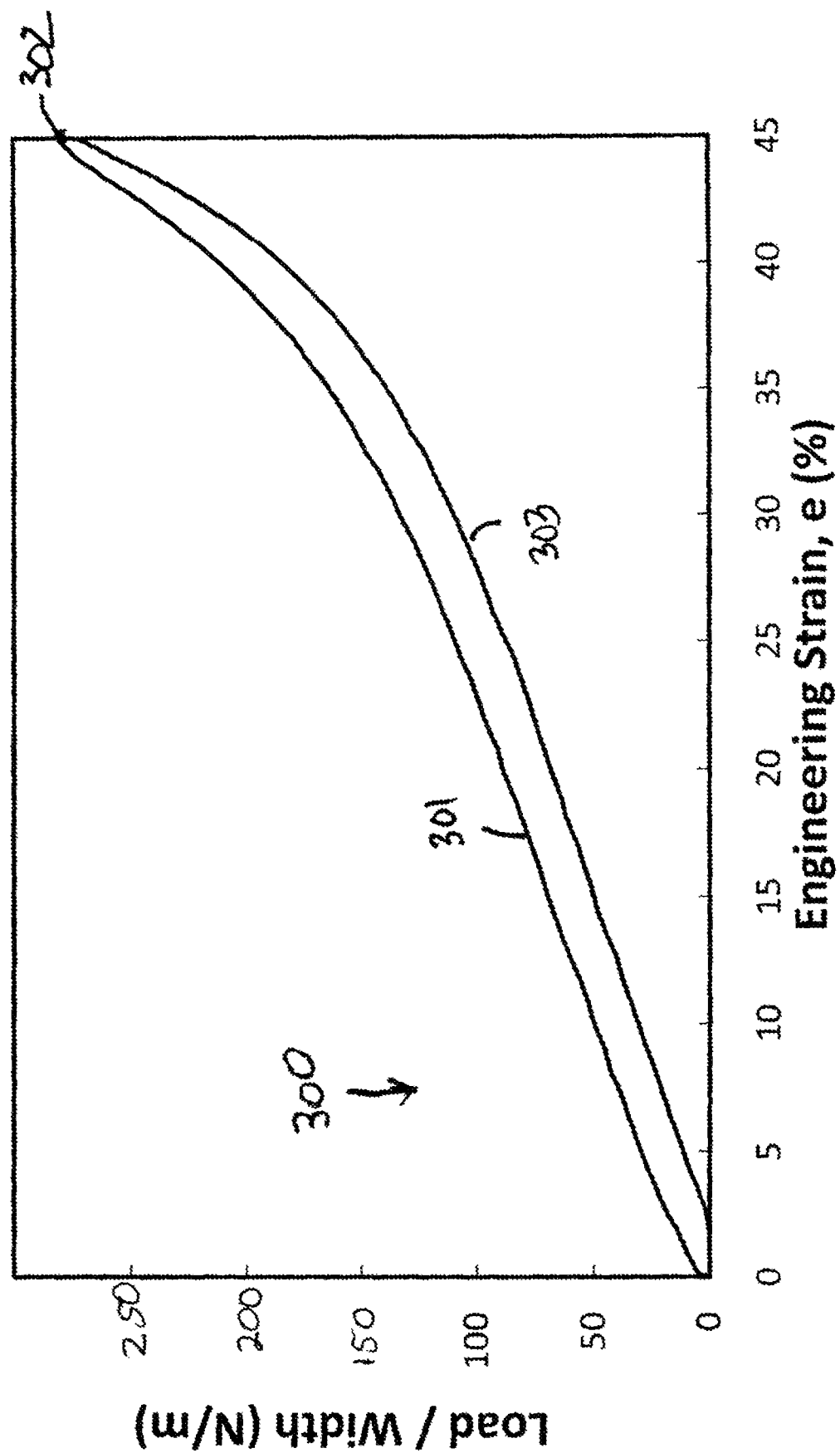
FIG. 3 is a schematic curve generally representing the force versus strain of a skin treatment device during loading and unloading of a skin treatment device.

According to the devices, kits and methods described herein, a skin device, a skin treatment device, a skin diagnostic device, a relative skin tension measuring device, wound treatment device, scar or keloid treatment device, scar or keloid amelioration or prevention device, bandage, or dressing may be provided that may be applied, attached to or coupled to one or more layers of the skin or tissue of a subject (hereinafter may be referred to as "elastic sheet" "dressing", "skin device" or "skin treatment device"). Devices kits, and methods described herein may be used to select a particular treatment method and/or to select skin treatment device or one or more properties thereof.

Skin has an inherent tension that varies from location to location and orientation of the skin. Because skin tension is related to scarring, many surgeons including plastic surgeons have followed a number of suggested patterns for incisions in order to minimize scarring and/or to improve healing. Some known systems for example, including Langer lines, Kraissl lines and Borges lines have been used to guide surgical incision locations and orientations. Generally, incisions have been made parallel to lines of greatest tension or perpendicular to lines of least tension. 'Devices, kits and methods described herein may relate to determining relative inherent skin tension in a subject or at a wound site. Devices kits and methods described herein may relate to determining orientation of relative amounts of skin tension in a subject such that one or more directions of relative greater or lesser tension may be identified.

Skin tension also may vary from person to person and/or from skin region to skin region. In using a tensioned skin treatment dressing as further described herein to treat a subject, diagnostic devices, kits and methods described herein may be used to select or assist in the selection of such dressing or mechanical properties of such dressing for a particular individual and/or a particular skin location or region. According to variations, a skin diagnostic device or a relative skin tension measuring device may be provided to identify which dressing to select from a plurality of such dressings and/or what strain or tension to create in the dressing.

As described herein an elastic sheet constructed in a manner similar to a dressing for treatment may be used to determine relative skin tension or orientation of amounts of skin tension. Accordingly, description of the dressing characteristics including but not limited to elastic properties, skin adhesives, liner shapes, or other construction features, may also apply to elastic sheets of the diagnostic skin devices. Properties described herein with respect to dressings may also apply to elastic sheets used in diagnostic devices. The elastic sheets or diagnostic devices may be tensioned and/or applied to the skin using a tensioning device and/or an applicator described herein in a manner similar to application of a dressing.

The elastic sheet mechanical properties and skin adhesives described herein may also be different from the properties of the dressings. For example an elastic sheet may be selected to have elastic or stress/strain related properties that are closer to the properties of skin.

According to variation, a kit may be provided comprising a plurality of dressings for treatment. Such kit may also include diagnostic devices such as described herein.

Devices, kits and methods described herein may treat skin at a skin site, sites by manipulating mechanical or physical properties of skin or by shielding skin from stresses, and/or by controllably stressing or straining the epidermis and layers of dermal tissue at or near a skin site, i.e., at or adjacent a wound or a treatment site of a subject's skin.

Devices kits and methods described herein may reduce tensile or compressive stress at a skin site. The stress at the skin site may be reduced to levels below that experienced by normal skin and tissue. The stress or strain at the skin site may be increased to levels above that experienced by normal skin and tissue. The stress or strain may be applied to surrounding tissue in one, two, or more directions to manipulate or reduce endogenous or exogenous stress at the skin site in one, two or more directions. Thus, devices and methods described herein may manipulate or reduce the stress experienced by skin and/or a wound and surrounding tissues in order to treat a subject. The device may also assist in preventing or reducing the incidence of wound dehiscence.

Devices, kits and methods described herein may be for treatment of a subject at a skin site including without limitation for wound treatment or the treatment, amelioration, or prevention of scars and/or keloids, by creating and/or maintaining a pre-determined strain in an elastic skin treatment device that is then affixed to the skin surface using skin adhesives to transfer a generally planar (e.g. compressive) force from the bandage to the skin surface. Other uses include wound closure and skin splinting/stabilization treatments.

It is believed that controlling, managing or modulating stresses acting in and/or on skin ("mechanomodulation") may have beneficial effects. Modulation of mechanical stresses or effects acting in and/or on skin may translate into or induce biomechanical response, including but not limited to, responses relating to scarring, scar proliferation or other effects. Unloading of exogenous and/or endogenous stress in the vicinity of the wound may ameliorate the formation of scars, hypertrophic scars, or keloids. The mechanical environment of an injury may be an important factor in tissue response to that injury. The mechanical environment includes exogenous stress (i.e., physiological stress which includes stress transferred to the wound via muscle action or physical body movement) and endogenous stress (i.e., dermal stress originating from the physical properties of the skin itself, including stress induced at the wound site due to swelling or contraction of the skin). The devices, dressings, kits and methods described herein may control or regulate the mechanical environment of a skin including but not limited to the mechanical environment of a wound. The devices, dressings, kits and methods described herein may also control or regulate the mechanical environment to ameliorate scar and/or keloid formation. The mechanical environment of skin may include stress, strain, or any combination of stress and strain. The control of a wound's mechanical environment may be active or passive, dynamic (e.g., by applying an oscillating stress) or static. The stresses and strains acting on the wound may involve the layers of the skin, such as the outer stratum corneum, the epidermis and dermis, as well as the underlying connective tissue layers, such as the subcutaneous fat. Devices and methods described here may shield a wound from its mechanical environment. The term "shield" is meant to encompass the unloading of stress experienced by the wound as well as providing a physical barrier against contact, contaminants, and the like. The devices and methods described here may shield a wound by unloading the wound and surrounding tissues from endogenous stress and/or exogenous stress. Thus, devices and methods described here may reduce the stress experienced by a wound and surrounding tissues to a lower level than that experienced by normal skin and tissue. Unloading of exogenous and/or endogenous stress in the vicinity of the wound may ameliorate the formation of scars, hypertrophic scars, or keloids.

A cell's external mechanical environment may trigger biological responses inside the cells and change cell behavior. Cells can sense and respond to changes in their mechanical environment using integrin, an integral membrane protein in the plasma membrane of cells, and intracellular pathways. The intracellular pathways are initiated by receptors attached to cell membranes and the cell membrane that can sense mechanical forces. For example, mechanical forces can induce secretion of cytokines, chemokines, growth factors, and other biologically active compounds that can increase or trigger the inflammatory response. Such secretions can act in the cells that secrete them (intracrine), on the cells that secrete them (autocrine), on cells surrounding the cells that secrete them (paracrine), or act at a distance from the point of secretion (endocrine). Intracrine interference can alter cell signaling, which can in turn alter cell behavior and biology including the recruitment of cells to the wound, proliferation of cells at the wound, and cell death in the wound. In addition, the extracellular matrix may be affected.

As noted above, the wound healing process may be characterized in three stages: early inflammatory phase, the proliferative phase, and remodeling. The inflammatory phase occurs immediately after injury and typically lasts about two days to one week. Blood clotting takes place to halt blood loss and factors are released to attract cells that can remove debris, bacteria and damaged tissue from the wound. In addition, factors are released to initiate the proliferative phase of wound healing. In the proliferative phase, which lasts about four days to several weeks, fibroblasts grow and build a new extracellular matrix by secreting collagen and proteoglycans. At the end of the proliferative phase, fibroblasts can act to contract the wound further. In the remodeling phase, randomly oriented collagen is organized and crosslinked along skin tension lines. Cells that are no longer needed can undergo apoptosis. The remodeling phase may continue for many weeks or months, or indefinitely after injury. Scars typically reach about 75-80% of normal skin breaking strength about 6-8 weeks after injury. In general, scars typically have a triangular cross-section. That is, a scar is usually smallest in volume near the skin surface (i.e., stratum corneum and epidermis) and increases in volume as it progresses into the deeper layers of the dermis.

Devices, methods, systems and kits described herein may relate to devices used to shield skin or a wound from its mechanical environment. The term "shield" is meant to encompass the unloading of stress experienced by the skin or wound as well as and/or providing a physical barrier against contact, contaminants, and the like. The stress shielding or force offloading devices and methods described here may shield the skin or a wound by unloading endogenous stress and/or exogenous stresses. In some variations, the devices may shield the skin from endogenous stress without affecting exogenous stress on the skin, e.g., devices that modify the elastic properties of the skin, etc. In other variations, the devices may shield the wound from exogenous stress without affecting endogenous stress on the skin wound. In still other variations, the devices shield the skin from both endogenous and exogenous stress.

In some variations, a dressing is provided, comprising an elastic sheet structure (e.g., a comprising a silicone polyurethane, TPE (thermoplastic elastomers), synthetic rubber or co-polyester material) comprising an upper surface, a lower surface, a first edge and a second edge opposite the first edge, and one or more adhesive regions. The dressing may further comprise a first release liner releasably attached to the adhesive region or regions. The adhesive region(s) may comprise a pressure sensitive adhesive. The dressing may be tapered or otherwise shaped to reduce skin tension at the edges. The dressing may have modified, reduced or no adhesive near its edges to reduce skin tension at the edges. Portions of the dressing may be unstrained and may thereby reduce strain in certain areas of the skin where the dressing is applied. In some specific examples, the unstrained area or areas are found between the edges of the dressing and the strained area(s). In some further examples, the unstrained areas are limited to this area and are not found, during application or use, between the strained areas of a single dressing, in use. In still further examples, the unstrained areas are limited to areas along the edges of a dressing that intersect the strain axis of the strained area(s), but not to areas along the edges of the dressing that are generally parallel to the strain axis.

The dressing may comprise an elastic member, such as a sheet of elastic material. The elastic material of the dressing may comprise a single layer of material or multiple layers of the same or different materials. The material may have any of a variety of configurations, including a solid, foam, lattice, or woven configuration. The elastic material may be a biocompatible polymer, e.g., silicone, polyurethane, TPE (thermoplastic elastomers), synthetic rubber or co-polyester material. The thickness of polymer sheets may be selected to provide the dressings with sufficient load carrying capacity to achieve desired recoverable strains, and to prevent undesired amounts of creep deformation of the dressings over time. In some variations, the thickness across dressings is not uniform, e.g., the thickness across the dressing may be varied to change the stiffness, the load carrying capacity, or recovery strains in selected orientations and/or locations. The elastic material of the exemplary dressing may have a thickness in the range of about 50 microns to 1 mm or more, about 100 microns to about 500 microns, about 120 microns to about 300 microns, or in some variations about 200 microns to about 260 microns. The exemplary dressings have an edge thickness of about 500 microns or less, 400 microns or less, or about 300 microns or less may exhibit less risk of skin separation from inadvertent lifting when inadvertently brushed against clothing or objects. In some variations, the dressings are tapered near the edges to reduce thickness. A tapered edge may also ameliorate peak tensile forces acting on skin tissue adjacent to the adhesive edges of the dressing. This may or may not reduce the risk of skin blistering or other tension-related skin trauma. In other variations, the edges of the dressing may be thicker than the middle of the dressing. It is hypothesized that in some configurations, a thicker dressing edge may provide a relative inward shift of the location of the peak tensile forces acting near the dressing edge, compared to dressings of uniform thickness. The elastic material may have a load per width of at least 0.35 Newtons per mm at an engineering strain of 60% or a load per width of at least 0.25 Newtons per mm at an engineering strain of 45%. The elastic material may have a load per width of no greater than about 2 Newtons per mm at the engineering strain of about 45% to 60%, about 1 Newtons per mm at the engineering strain of about 45% to 60%, about 0.7 Newtons per mm at the engineering strain of about 45% to 60%, or no greater than about 0.5 Newtons per mm at the engineering strain of about 45% to 60%. The system elastic material may have a load per width that does not decrease from an engineering strain of 0% to 60%, a load per width plot that increases linearly from an engineering strain of 0% to 60%, or a load per width plot that is not convex from an engineering strain of 0% to 60%. The elastic material may comprise an adhesive configured to maintain a substantially constant stress in the range of 200 kPa to about 500 kPa for at least 8 hours when strained to an engineering strain of about 20% to 30% and attached to a surface. The elastic material may comprise an adhesive configured to maintain a substantially constant stress in the range of 200 kPa to about 400 kPa for at least 8 hours when strained to an engineering strain of about 20% to 30% and attached to a surface. The substantially constant stress may vary by less than 10% over at least 8 hours, or by less than 5% over at least 8 hours.

Although the described dressings may have a generally rectangular configuration with a length and/or width of about 160 mm to about 60 mm, in other variations the dressing may have any of a variety of lengths and widths, and may comprise any of a variety of other shapes. Also, the corners of the dressing may be squared or rounded, for example. The lengths and/or widths of an exemplary dressing may be in the range of about 5 mm to about 1 meter or more, in some variations about 20 mm to about 500 mm, and in other variations about 30 mm to about 50 mm, and in still other variations about 50 mm to about 100 mm. In some variations, the ratio of the maximum dimension of the dressing (e.g. its length) to an orthogonal dimension to the maximum dimension (e.g. width), excluding the minimum dimension of the dressing (e.g. the thickness), may be in the range of about 1:3, about 1:2, about 1:1, about 2:1, about 3:1, about 4:1 about 5:1, about 6:1, about 7:1, about 8:1, about 9:1 or about 10:1 or greater. In some variations, the strain axis of the dressing in use may be oriented with respect to the maximum dimension or to the orthogonal dimension to the maximum dimension. In some variations, the final compressive stress and strain imposed onto the skin by the elastic material may be the result of the dynamic equilibrium between the tensile stress in the skin and the elastic material of the dressing. The skin at the skin site typically comprises an inherent tension that stretches incision site, whether or not any tissue was excised from the skin site. The elastic material and the adhesive region may be configured to be applied to a skin location so that when the dressing is stretched to a particular tension and then adhered to the incision site, tensile stress in the dressing is transferred to the incision site to compress the tissue directly under the dressing along a tangential axis to the skin surface, the stress and strain imposed onto the skin location has a net or resultant orientation or axis is also generally tangential or planar to the elastic material and/or the outer surface of the skin location, with a similar axis to the orientation or axis of the tensile stress in the dressing. The tension in the dressing will relax to a tension level that maintains equilibrium with increased tension in the skin adjacent to the dressing. The application of the dressing to the skin location may involve the placement of the dressing without overlapping or being wrapped onto itself, e.g. wherein only adjacent regions of the dressing are interconnected and wherein non-adjacent regions of the dressing are not interconnected. The actual amount of stress and strain imposed on the skin may vary, depending upon the particular person, skin location, the thickness or various mechanical characteristics of the skin layers (e.g. epidermis, dermis, or underlying connective tissues), and/or the degree of pre-existing scarring, for example. In some further variations, the wound treatment dressing may be selected or configured for use at a specific body location, such as the scalp, forehead, cheek, neck, upper back, lower back, abdominal region, upper torso (including but not limited to the breast folds), shoulder, upper arm, lower arm, palm regions, the dorsum of the hand, finger, thigh, lower leg, the dorsum or plantar surface of the foot, and/or toe. Where applicable, some body regions may be further delineated into anterior, posterior, medial, lateral, proximal and/or distal regions, e.g. the arms and legs.

The dressing may be configured to impose a skin strain in the range of about 10% to about 60% or more, in other configurations about 15% to about 50%, and in still other configurations, about 20% to about 30% or about 40%. To achieve the desired degree of skin strain, the dressing may be configured to undergo elastic tensile strain in the range of about 20% to about 80% or more, sometimes about 30% to about 60%, and other times about 40% to about 50% or about 60%. The dressing may comprise any of a variety of elastic materials, including but not limited to silicones, styrenic block copolymers, natural rubbers, fluoroelastomers, perfluoroelastomers, polyether block amides, thermoplastic elastomers, thermoplastic polyurethane, polyisoprene, polybutadiene, and the like. The material of the exemplary dressing may have a Shore A durometer in the range of about 20 to about 90, about 30 to about 80, about 50 to about 80. The exemplary dressing was constructed of MED 82-5010-05 by NUSIL TECHNOLOGY LLC (Carpinteria, Calif.). Other examples of suitable materials are described in U.S. application Ser. No. 11/888,978, which was previously incorporated by reference in its entirety.

When the dressing is applied to a skin location and allowed to at least partially recover to its base configuration, the recovery level or equilibrium level of strain in the dressing may be in the range of about 4% to about 60% or more, in other configurations about 15% to about 50%, and in still other configurations, about 20% to about 30% or about 40%. The ratio between the initial engineering tensile strain placed onto the dressing before recovery and the resulting engineering compressive strain in the skin may vary depending upon the skin type and location, but in some examples, may be about 2:1. In other examples, the ratio may be in the range of about 4:1 to about 5:4, about 3:1 to about 5:3, or about 5:2 to about 2:1. These skin strain characteristics may be determined with respect to a reference position of the body or body part, e.g. anatomical position, to facilitate reproducible measurements. The particular degree of strain may be characterized as either an engineering strain or a true strain, but may or may not be calculated based upon or converted from the other type of strain (e.g. the strain may be based upon a 45% engineering strain that is converted to a true strain).

In some further variations, one or more characteristics of the elastic material may correspond to various features on the stress/strain curve of the material. For example, the engineering and true stress/strain curves for one specific example of the dressing comprises a material that exhibits an engineering stress of about 1.2 MPa at about 60% engineering strain, but in other examples, the engineering stress may be in the range of about 900 KPa to about 3.5 MPa, about 1 MPa to about 2.2 MPa, about 1 MPa to about 2 MPa, about 1.1 MPa to about 1.8 MPa, about 1.1 MPa to about 1.5 MPa, about 1.2 MPa to about 1.4 MPa. When unloading or relieving stress from the dressing, the material may be configured with an engineering stress of about 380 KPa at about 40% engineering strain, but in other examples, the engineering stress during unloading of the material to about a 40% strain may be in the range of about 300 KPa to about 700 KPa, about 325 KPa to about 600 KPa, about 350 KPa to about 500 KPa, or about 375 KPA to about 425 KPa. When unloading the material to an engineering strain of about 30%, the material exhibits an engineering stress of about 300 KPa, but in other examples, the engineering stress when unloading the material to about 30% strain may be in the range of about 250 KPa to about 500 KPa, about 275 KPa to about 450 KPa, about 300 KPa to about 400 KPa, or about 325 KPA to about 375 KPa. When unloading to an engineering strain of about 20%, the material may have an engineering stress of about 100 KPa, but in other examples, the unloading engineering stress at about 20% may be in the range of about 50 KPa to about 200 KPa, about 75 KPa to about 150 KPa, or about 100 KPa to about 125 KPa. In some examples, the material may be configured to at least achieve a specific range or level of engineering stress at each of the specified engineering strain levels described above, but in other examples, the material may be configured for lower levels of maximum engineering strain, e.g. up to about 30% or about 40%.

In some examples, certain portions of the stress/strain curve may have a particular morphology. For example, for a particular level of maximum strain the loading curve may be generally linear on the corresponding true stress/strain curve. In an example using a dressing described herein, up to a true strain of about 45%, the loading curve had a generally linear configuration. In other examples, the configuration may only be linear along a portion of the loading curve or may be curved along the entire loading curve. Where the loading curve is non-linear, the loading curve may be convex, concave or both. Also, in some examples, the tangent line of the loading curve (i.e. the line between the two triangles) may also be generally co-linear.

In some variations, the elastic material comprises a material having an elastic modulus E of at least about 1 MPa, about 1.5 MPa, about 2 MPa, about 2.5 MPa, about 3 MPa, about 3.5 MPa, about 4 MPa, about 5 MPa, about 6 MPa, about 7 MPa, about 8 MPa, about 9 MPa or at least about 10 MPa or greater. The material elastic modulus E may be no greater than about 10 MPa, about 9 MPa, about 8 MPA, about 7 MPa, about 6 MPa, or about 5 MPa, or about 4 MPa.

In addition to the absolute stress levels at certain strain levels described above, the material may also be characterized with respect to the ratio between a) the stress to achieve a particular strain during loading, and b) the stress at the same strain during unloading. For example, the material may have a ratio of at least 4:1 to about 3:2 at each of the 20%, 30% and 40% strain levels, but in other examples, the material may exhibit these ratios only at 20%, at 30%, or at 40% strain levels, or at both 20% and 30% but not 40%, or at both 30% and 40% but not 20%. In other examples, the ratio at one, some or all of the strain levels may be in the range of about 3:1 to about 2:1, or about 5:2 to about 2:1.

In some examples, the elastic material of the dressing may be configured under testing conditions to achieve a stable level of stress at a constant strain, e.g. the material exhibits a limited amount of stress relaxation over a particular period of time and at a particular level of strain. The period of time may be at least about 8 hours, about 12 hours, about 18 hours, about 24 hours, about 36 hours, about 48 hours, about 72 hours, about 4 days, about 5 days, about 6 days, or about a week or more. The level of strain may be about 10%, about 20%, about 30%, about 40%, about 50%, about 60%, about 70%, or about 80% or more. The stress of the exemplary dressing over various time curves may be configured to maintain an engineering stress of about 300 KPa at an engineering strain of about 30% without noticeable deviation over a period of about 1 hour, about 2 hours, about 3 hours, about 4 hours, about 5 hours, about 6 hours, about 7 hours, or about 8 hours or more. The stresses at 10% strain, 20% strain, and at 40% may be lower or higher.

In some variations, the elastic material or the dressing may be configured under testing conditions to maintain a particular minimum level of stress when held at a constant strain over a particular time period. In an example to assess the ability of a backing material to maintain a stress and strain on skin over time, engineering strains were measured while each backing material was tensile strained to 60% at a rate of 100 microns per second and held for 10 minutes, and then dropped to a strain of 30% at a rate of 100 microns per second and held for 9 hours. For example, the exemplary dressing is able to maintain an engineering stress level of about 350 KPa at an engineering strain of 30%. In some other examples, the minimum level of stress may be about 100 KPa, about 120 KPa, about 140 KPa, about 160 KPa, about 180 KPa, about 200 KPa, about 220 KPa, about 240 KPa, about 260 KPa, about 280 KPa, about 300 KPa, about 320 KPa, about 340 KPa, about 360 KPa, about 380 KPa, about 400 KPa, about 420 KPa, about 440 KPa, about 460 KPa, about 480 KPa, about 500 KPa, about 600 KPa, about 700 KPa, about 800 KPa, about 900 KPa or about 1000 KPa or greater. The level of constant strain may be different in other configuration, with a level of about 15%, about 20%, about 25%, about 30%, about 35%, about 40%, about 45%, about 50%, about 55%, about 60%, about 65%, about 70%, about 75%, or about 80%. The time period over which the dressing is able to maintain a stress level may be at least about 2000 seconds, about 3000 seconds, about 4000 seconds, about 5000 seconds, about 6000 seconds, about 7000 seconds, about 8000 seconds, about 9000 seconds, about 10000 seconds, about 20000 seconds, about 30000 seconds, about 40000 seconds, about 50000 seconds, about 60000 seconds, about 70000 seconds, about 24 hours, about 36 hours, about 48 hours, about 72 hours, about 4 days, about 5 days, about 6 days, about 7 days, about 10 days, about 2 weeks, about 1 month or more. In some variations, the dressing, the elastic material and/or the adhesive material is configured to exhibit less than about a 15% change in stress or strain level over the particular period when applied to a skin surface or test surface. In other examples, the degree of change may be about 12%, about 10%, about 8%, about 6%, about 5%, about 4%, about 3%, or about 2% or less. The stress or strain may be an engineering stress or strain, and/or a true stress or strain.

The adhesive used may be, for example, a pressure activated adhesive (PSA), as a silicone, acrylic, styrene block copolymer, vinyl ether, nitrile or other PSA. In other variations, a non-pressure sensitive adhesive may be used, including but not limited a heat or light-cured adhesive. The pressure sensitive adhesive may be made from, e.g., polyacrylate-based, polyisobutylene-based, silicone-based pressure sensitive adhesives, synthetic rubber, acrylic, and polyisobutylene (PIB), hydrocolloid, and the like. The T-peel release force and blunt probe tack force of the adhesive may be measured by a standardized test method, such as ASTM D1876 and ASTMD2979 or other appropriate method. In some variations, the T-peel release force or blunt probe tack test value of the adhesive is configured to maintain loads of at least about 50 mPa/mm for at least about 24 hours, about 48 hours, about 72 hours, about 1 week, about 2 weeks, about 3 weeks, about 4 weeks or more. In other variations, the loads may be at least about 75 mPa/mm, about 100 mPa/mm, about 125 mPa/mm, or at least about 150 mPa/mm over the particular time period. The degree of adhesion (e.g. as measured by the T-peel release force or blunt probe tack test value) may vary depending upon the degree of strain placed onto the skin or incision site, and in some variations, these time periods may be based upon an average skin strain of about 10%, about 20%, about 30%, about 40%, or about 50% or more. In some variations, the adhesive may have a T-peel release force of at least about 150 kg/m, about 160 kg/m, about 170 kg/m, about 180 kg/m, about 190 kg/m, about 200 kg/m, about 210 kg/m, about 220 kg/m, about 230 kg/m, about 240 kg/m, about 250 kg/m, about 260 kg/m, about 270 kg/m, about 280 kg/m, about 290 kg/m, about 300 kg/m, about 310 kg/m, about 320 kg/m, about 330 kg/m, about 340 kg/m, about 350 kg/m, about 400 kg/m, about 450 kg/m, or at least about 500 kg/m or higher. In some further variations, the T-peel release force may be no greater than about 1000 kg/m, about 900 kg/m, about 800 kg/m, about 700 kg/m, about 600 kg/m, about 500 kg/m, about 400 kg/m or about 300 kg/m. The blunt probe tack test value of the adhesive may be at least about 0.50 kg, about 0.55 kg, about 0.60 kg, about 0.65 kg, about 0.70 kg or about 0.75 kg or higher, and may be no greater than about 1 kg, about 0.9 kg, about 0.8 kg, about 0.7 kg, or about 0.6 kg. The T-peel release force and blunt probe tack force may be measured by a standardized test method, such as ASTM D1876 and ASTMD2979 or other appropriate method. Other features or variations of the device are described in U.S. application Ser. No. 11/888,978, filed on Aug. 3, 2007, incorporated in its entirety herein by reference.

The release liners may comprise any of a variety of materials, including both opaque and transparent materials. The release liners may comprise Mylar or paper, or any other material with reduced adhesion to the adhesive material(s) of the device. For example, for a silicone adhesive, a fluoropolymer-treated polyester film may be used, and for an acrylic pressure sensitive adhesive, a silicone treated polyester or Mylar film or silicone treated craft paper may be used. In variations where the device has multiple separate adhesive regions, separate release liners may be provided for each region, or some regions may be covered by the same release liner.

A device may be used to strain and/or maintain a strain on a dressing. The device may further comprise a releasable locking mechanism, attachment mechanism or adhesive, configured to maintain the member or mechanism in a strained configuration. An applicator or tensioning device may be used strain, tension, and or apply a device to a subject. A variety of locking, latching, securing, attaching or detent mechanisms may be used to maintain the applicator or tensioning device in a various configurations including but not limited to unstrained, partially strained, strained configurations. A variety of locking, latching or detent mechanisms may be used to maintain a dressing in a variety of configurations including unstrained, partially strained, strained. By locking the applicator, tensioning device, or dressing in a strained position, a predetermined strain of a given dressing may be achieved. The predetermined amount of strain may be a predetermined absolute percentage of strain or level of force that is independent of the shape and/or size of the treatment site. As a further example, this absolute percentage of strain or level of force may or may not be independent of the minimum strain or force to achieve sutureless wound closure (e.g. a relative strain or force to achieve opposition of the incision edges of a treatment site). Furthermore, the force needed to achieve wound closure is not a predetermined strain or force, since the final level of strain or force is not known until opposition of the incision edges is achieved.

The devices, kits or methods described herein may include a carrier, support, base, applicator or tensioning device, each of which may: contain, hold, carry or support a dressing at least temporarily; may be used to prepare a dressing for application; may be used to deliver, orient or apply a dressing; may be used to maintain a dressing in a stressed or strained configuration; may be used to stress or strain a dressing; may be used to separate the dressing from the carrier, support, base, applicator or tensioning device and/or may be used during or after application of a dressing to provide additional treatment to a wound, incision or other treatment location; and/or may be used to apply pressure to a wound, incision or other treatment location. According to some variations, an applicator may provide structural support for a dressing while or after an adhesive liner is released. According to some variations, the assembly may be constructed to avoid folding or bending of the dressing to the extent that the adhesive on the dressing sticks to itself. For example, when some variations of the dressing are held or supported at one point or along one edge of the dressing in a cantilever configuration, the dressings will not bow, laterally deform, or otherwise deform out of plane, under their own mass or configuration.

In addition to amelioration of scar formation, other uses for such skin treatment device may or may not include without limitation, for example, treating skin related conditions such as acne, blemishes, rosacea, warts, rashes (including but not limited to erythematous, macular, papular and/or bullous conditions), psoriasis, skin irritation sensitivity, allodynia, telangiectasia, port wine stains and other arteriovenous malformations, and ectopic dermatitis; treating or improving existing scars, wrinkles, stretch marks, loose or sagging skin or other skin irregularities; lifting pinning, holding, moving skin for various purposes such as during pre-operative preparation, during surgical procedures for example as a low profile tissue retractor, to stabilize blood vessels during needle or catheter insertion, postoperatively, pre or post operatively for pre-treating or preconditioning skin for example, prior to scar revision, wound incision, body contouring, in mastectomy skin expansion, aesthetic skin treatment or resurfacing whether topical or subdermal, whether or not using an energy modality such as, for example, microwave, radio-frequency ablation, high-intensity focused ultrasound, laser, Infrared, incoherent light, thermal (heat and/or cold, ablative or nonablative), use of vacuum or suction, vibration or massage (e.g. ENDERMOLOGIE®, LPG Systems, France), during weight loss, or for aesthetic purposes; hair removal or hair loss; treating and/or closing skin injuries for example, incisions, wounds, chronic wounds, bed sores, ulcers (including venous stasis ulcers), preventing or reducing the incidence of wound dehiscence, diabetic skin or wound conditions, burn healing and/or relief; acting as an occlusive or negative-pressure wound dressing; protecting incisions or wounds, e.g. prevention of splitting or opening, protecting newborn belly buttons after cutting umbilical cord. Such treatments may also be used to treat skin grafts (including split-thickness and full-thickness grafts, xenografts, cadaveric graft, autologous grafts), skin flaps and skin substitutes, with or without the use of biomaterials or biodressings, either on top and/or below the graft/flap/substitute, or otherwise in the treatment site. Examples of such materials may include ALLODERM® (LifeCell Corp., Branchburg, N.J., OASIS® (Healthpoint Ltd., Fort Worth, Tex.), INTEGRA® Dermal Regeneration Template (Integra Life Sciences Holding Co., South Plainfield, N.J.), BIOBRANE® and BIOBRANE-L (Bertek Pharmaceuticals, Sugarland Tex.), APLIGRAF® (Organogenesis Inc., Canton, Mass.), EPICEL® (Genzyme Biosurgery, Cambridge, Mass.), CELADERM™ (Celadon Science LLC, Hyattsville, Md.), TRANSCYTE® and DERMAGRAFT® (Advanced BioHealing Inc., Westport, Conn.), EZ DERM™ (Brennan Medical Inc., St. Paul, Minn.), LASERSKIN® (Fidia Advanced Biopolymers, Italy), ORCEL® (FortiCell Bioscience Inc., Englewood Cliffs, N.J.), and the like. Such treatments may include use of a drug or other therapeutic agent that may be applied to the skin with such device. The agents may include but are not limited to antibiotics, anti-fungals, immune modulators including corticosteroids and non-steroidal immune modulators. The agents may be provided in any of a variety of formulations, including but not limited powders, gels, lotions, creams, pastes, suspensions, etc. The devices may also be used for purposes of delivering a drug to the skin or through the skin, for example by stretching the skin and applying a drug thereto. Different configurations of the device may be amenable to the size or geometry of different body regions. The treatments may be applied to regions of any shape (e.g. linear, curved, stellate), size or depth, and to one or more regions of the body, including but not limited to the scalp, forehead, face (e.g. nose, eyelid, cheeks, lips, chin), ears, neck, shoulder, upper arm, lower arm, palm, dorsum of the hand, fingers, nailbed, axilla, chest, nipple, areola, back, abdomen, inguinal region, buttocks, perineal region, labia, penis, scrotum, thigh, lower leg, plantar surface of the foot, dorsal surface of the foot, and/or toes. Such devices may also be referred to herein as a "dressing", "skin device" or "skin treatment device".

"Dressing" or "Skin Device" as used herein may include but is not limited to an elastic sheet, a skin diagnostic device, a relative tension measuring or determining device, askin treatment device, wound treatment device, scar or keloid treatment device, scar or keloid amelioration or prevention device, bandage, or dressing, that may be applied, attached to or coupled to one or more layers of the skin or tissue of a subject.

Various material and mechanical properties of skin, including but not limited to, e.g., skin thickness, elasticity, compression modulus, tension modulus, stiffness, inherent stress and/or strain, may vary across different body regions (including but not limited to for example, face, eyelid, cheek, forehead, chin, lips, shoulder area, upper arm, lower arm, hands, fingers, ear, upper back, lower back, buttocks, upper abdomen, lower abdomen, thigh, upper leg, lower leg, chest, knee, thigh, calves, head, neck, breasts) and/or from subject to subject based on individual skin characteristics or among other things, depending on various demographic factors including but not limited to age, sex, race, body mass index, changes in weight, sun exposure, dietary habits, environmental factors, smoking and other health related issues. A region with less inherent tension may require less force to strain skin or unload forces or tension a given amount. For example, a location such as an eyelid may have less inherent stress or tension in the skin than for example, an abdomen of the same subject. Thus, such a skin site or zone may require less force to strain skin (in tension or compression) or unload forces or tension a desired amount, than the zone with higher inherent stress or tension. On the other hand, a region with greater inherent tension may require greater force to strain skin or unload forces or tension a desired amount. A skin location on one subject may have greater or lesser tension than on another subject at a similar location.

According to variations, a device may be used to determine a relative skin tension at a particular skin region or location of a subject. Based on this relative determination, a device or devices may be selected to impart a desired, approximated or estimated amount of strain or off-loading of stresses at a skin site. According to variations, a relative tension measurement may be made pre-operatively, on healthy skin, on skin adjacent a wound to be closed, immediately post-closure, and/or at any step during the healing process. According to variations, a tension measuring device may be used to check skin tension after skin device application, for example, to confirm adequacy of selection and/or placement of the skin device. According to variations, periodic monitoring may be performed over a period of use of a skin device and/or over a period of healing and scar formation. According to variations, the device or procedure may be used to assess how or how tight to tension sutures.

According to variations, one or more mechanical force properties of a skin shielding device may be selected for use based on an estimated or measured relative inherent skin tension (or other mechanical skin properties) of a particular skin site, skin area or skin zone.

One or more such device mechanical properties may include but is not limited to strain value of the device, imparted skin strain by the device depending on skin site, load or force per width, stress strain relationships in loading or unloading and/or device stiffness, modulus of elasticity, loss modulus, storage modulus, complex modulus, durometer, hardness, creep and stress relaxation characteristics.

Such device or device properties may be, among other things, based on measurements of skin properties, estimated based on location of a skin site to be treated, estimated based on patient demographic information, and/or estimated based on measurements at one or more particular skin zones, e.g., locations on a particular subject's body.

Such device or device properties may be selected based on a desired amount of stress offloading, a desired skin strain and/or desired forces on the skin outside the skin treatment device, adjacent the skin treatment device, and/or at the edges of the skin treatment device. It is believed that in some subjects, skin irritation may be reduced where the stress at the edge of the device is lower. According to variations one or more mechanical properties of a skin treatment device may be selected to be within a range where the device unloads a sufficient amount of tension to treat the skin or wound while having sufficiently low edge stresses to reduce skin irritation.

According to variations, skin may be selectively mechanomodulated using one or more devices or methods. A skin treatment device may be a pre-strained (e.g., at point of manufacture or for a period of time prior to use) to a particular force or strain level. The pre-strained device with the desired force level or strain may be selected for a particular skin zone and/or a particular subject.

A skin treatment device may be strained by a user with a tensioning (stretching) device, or an applicator. Such tensioning device may provide a predictable amount of strain and/or a particular force to a skin treatment device. Thus, a tensioning device may be selected from one or more tensioning devices with different force or strain application properties. A tensioning device or applicator may also provide a various selectable amounts of force or strain to a skin device. Such tensioning device may be configured to allow a user to select an amount of stress, strain or force to be applied to a skin treatment device which may be selected for a particular skin zone and/or a particular subject. In some variations a skin treatment device may be applied to pre stressed or pre-strained skin where the level of stress or strain in the skin may be pre-selected based on similar factors. Examples of tensioning devices, applicators, pre-strained devices and skin pre-straining devices and methods are set forth in U.S. application Ser. Nos. 12/854,859, 13/029,023; 13/345,524; and 13/552,521 which applications are incorporated in their entirety herein by reference.

According to variations, device materials and/or construction of a plurality of skin devices may individually vary where at a given preset percent strain, each skin treatment device may exhibit a different force property. One of the plurality of skin treatment devices at such predetermined strain may be selected based on a given force profile for the skin device (at a particular initial strain level).

Referring to FIGS. 1A to 1F, a skin tension measuring device 100 is illustrated comprising a skin platform 110 coupled to a cylindrical portion 130, and a spring-loaded plunger 120 movably or slideably positioned through the cylindrical portion 130. The skin platform 110 and cylindrical portion define a chamber 140 for receiving the plunger 120. The plunger 120 comprises plunger handle 170 coupled to a post 160 and plunger end 150. The plunger handle 170 is positioned outside of the cylindrical portion 130; the post 160 slides through an opening 134 through the top 133 of the cylinder 130; and the end 150 is positioned within a cavity 135. An outwardly biased spring member 180 having a known spring constant is positioned between the plunger handle 170 and the top 133 of the cylindrical portion 130 where it engages the plunger handle 170 and the top 135 of the cylindrical portion 130. The spring member 180 tends to move the plunger 120 upwardly.

The plunger 120 is shown in an initial loaded position in FIGS. 1A to 1C. The bottom side 115 of the skin platform 110 is positioned on skin at a skin location or zone to be tested. The plunger 120 is depressed so that the end 150 of the plunger 120 is against an area of skin 190 to be tensioned by the plunger 120. The side 155 of plunger end 150 substantially sealing engages the inner wall 135 of the chamber 140 so that when the plunger 120 is released, a vacuum type force is created between the skin area 190 and the end 150 of the plunger 120. In the configuration shown in FIGS. 1A to 1C with the plunger depressed by a user, the skin area 190 is un-tensioned while the spring member 180 is tensioned.

As shown in FIGS. 1D to 1F, the plunger 120 is released whereby the spring member 180 biases the plunger handle 170 upward. Tension in the skin area 190 counteracts the spring tension to reach equilibrium. Thus, the amount that the spring member 180 moves the plunger 120 upward corresponds or may be correlated to the inherent tension in the skin at the area 190. Accordingly the deflection or the change in distance of the plunger 120 may correlate to the inherent tension in the skin The cylinder 130 includes a window 138 through which the vertical position of the top 165 of the end 150 of the plunger 120 may be visible. Vertically spaced indication lines 137A to 137D are located on the cylinder 130. The vertically spaced indication lines 137A to 137D correspond or correlate to relative skin tension amounts or levels. According to a variation, the top 165 of the end 150 is aligned with the indication line 137A when the plunger 120 is depressed and the end 150 is positioned on the area of skin 190. When the skin is tensioned for example, as shown in FIGS. 1D to 1F, the indication lines 137A to D may be used to identify or elect a type or force properties of elastomeric device to be applied to the skin (or desired skin pre-straining level), i.e., based on the inherent tension in the skin at the skin site or area of skin 190. The elastomeric device type may be a device having a predetermined amount of force at a pre-determined level of strain. It may be a device with a predetermined amount of strain. The lines may also indicate to a user an amount of strain to apply to a particular skin treatment device before applying it to the surface of a skin. The lines may also indicate an amount of strain to pre-apply to skin before applying a skin treatment device that is un-tensioned or tensioned by particular amount. For example, a skin treatment device as described in U.S. Pat. No. 7,683,234 incorporated in its entirety without limitation herein by reference), may be used. Also as described in Co-pending application Ser. No. 12/854,859 entitled "Devices and Methods For Dressing Applicators", application Ser. No. 13/345,524 entitled "Wound or Skin Treatment Devices and Methods", application Ser. No. 13/411,394, or application Ser. No. 13/411,443, (incorporated in their entirety without limitation herein by reference), an applicator may be used that may permit selecting the amount of strain applied to a skin treatment device. Additionally, an amount of pre-strain to be applied to skin may be selected as shown in co-pending application Ser. No. 13/029,023 entitled "Skin Straining Devices and Methods" (incorporated in its entirety without limitation herein by reference).

In use, the skin platform 110 is attached in the first to a skin area 190 for testing with a high tack adhesive such as a PSA. In the initial configuration, the plunger 120 is depressed and the spring loaded and locked into an initial position. Once the skin platform 110 is secured, the spring member 180 is released and the skin is tensioned as illustrated in FIGS. 1D to 1F. The user reads the location of the top of the plunger end 150 and determines based on the location with respect to one or more indication lines 137A to 137D, how to treat a subject, i.e. which skin treatment device, strain level, or force level to apply to pre-strain a skin treatment device or to pre-strain skin. The device 100 may then be removed or peeled off the skin.

The line A is shown when the plunger 120 is fully depressed. The line B may indicate a greater mechanical skin property or inherent skin tension and the use of a skin device configured to provide or deliver relatively greater force to the skin at the surface. Line C may indicate a mid-range mechanical skin property or inherent skin tension and the use of a skin device configured to provide or deliver a relatively mid-range force to the skin at the surface. Similarly, line D may indicate of a lower inherent skin tension and the use of a skin device configured to provide or deliver relatively less force to the skin at the surface.

FIG. 7 illustrates a plurality of packages 701, 702 of a plurality of skin treatment devices associated for use with a body region with a label 703, 704 respectively indicating the body region. Alternatively or additionally, graphic indicators of body locations 705, 706 respectively may be provided. The device 701, 702 may or may not be packaged together in a package 700. The may be packaged individually or in other groupings. Devices may be labeled with other indicia with or without body region indicia. For example devices may be labeled with colors, letter, numbers or other indicia that correlate the device to a particular use, mechanical property, and/or patient demographic or any combination of, location, relative range or amount of the foregoing.

The information may also be used to determine and/or to compare a relative skin tension at one skin site versus another location or an average skin site or a standard. For example, the tension at the abdomen may guide the user to select a device for a subject's back or eyelid (knowing relative similarities or differences in skin regions of a subject for example as described herein). Tension at one site may be used to determine or approximate tension at a location where such measurement may be more difficult, or where a wound is present and where it would be undesirable or not feasible to measure inherent tension of skin. A measurement may also be taken at a region that is expected to be similar to the location where the device is to be used. Also, a measurement may be taken at a region with an expected difference or delta with respect to the location where the device is to be used, ant the measurement may be used to estimate or select or help identify a device or device property to be selected. For example, the device may be used to determine if the skin location exhibits a greater, lesser or typical tension as compared with an average or standard e.g., for a particular region or demographic.

In the following example, it is shown that location or zone specific variation in skin biomechanical properties may be characterized using non-invasive technologies. With respect to formation of scars that may be affected by the biomechanical properties of a skin location or zone, there may be some locations that have higher inherent stress levels and may thus have higher wound stress levels and may accordingly be more pre-disposed to scar formation or scar proliferation than others. Accordingly, there may be specific force properties or ranges of force properties of skin treatment devices that may be selected based on a particular skin location or zone.

EXAMPLE I

To characterize regional differences in human skin mechanical properties, inked grids were placed at various locations, zones or sites on the skin of three healthy human male subjects. Then, skin treatment devices described below were applied to the skin sites and compressive skin strain levels were determined as described below.

The skin treatment or stress shielding devices were silicone devices constructed of SSF-MLTN-950 by Specialty Silicone Fabricators, Inc. (Paso Robles, Calif.). The samples were initially about 2"×1" with a thickness of 0.010"±0.001. A pressure sensitive skin adhesive, made of MD 4502 PSA (Manufactured by Dow Chemical, Inc.) of about 0.004" to about 0.006" thick was applied to a skin interfacing surface of the devices. The samples had a durometer value of about 45 to 55 (Shore A scale), a tensile strength of about 1,535 psi, elongation of about 719% and a specific gravity of about 1.11 to 1.16. (In other examples, the device material may have a durometer value of about Shore A 15 to about 90, sometimes about Shore A 35 to 75 and other times about Shore A 50 to 60, or Shore A 50 to 75.)

The skin treatment device was used to impose compressive strains on unwounded skin of three healthy human male subjects. Each skin treatment device was initially strained to about 45%+−2% of the initial length 10 of the device. For the particular device used, the initial load on the device was approximately 0.28 N/mm.

Figure 6:
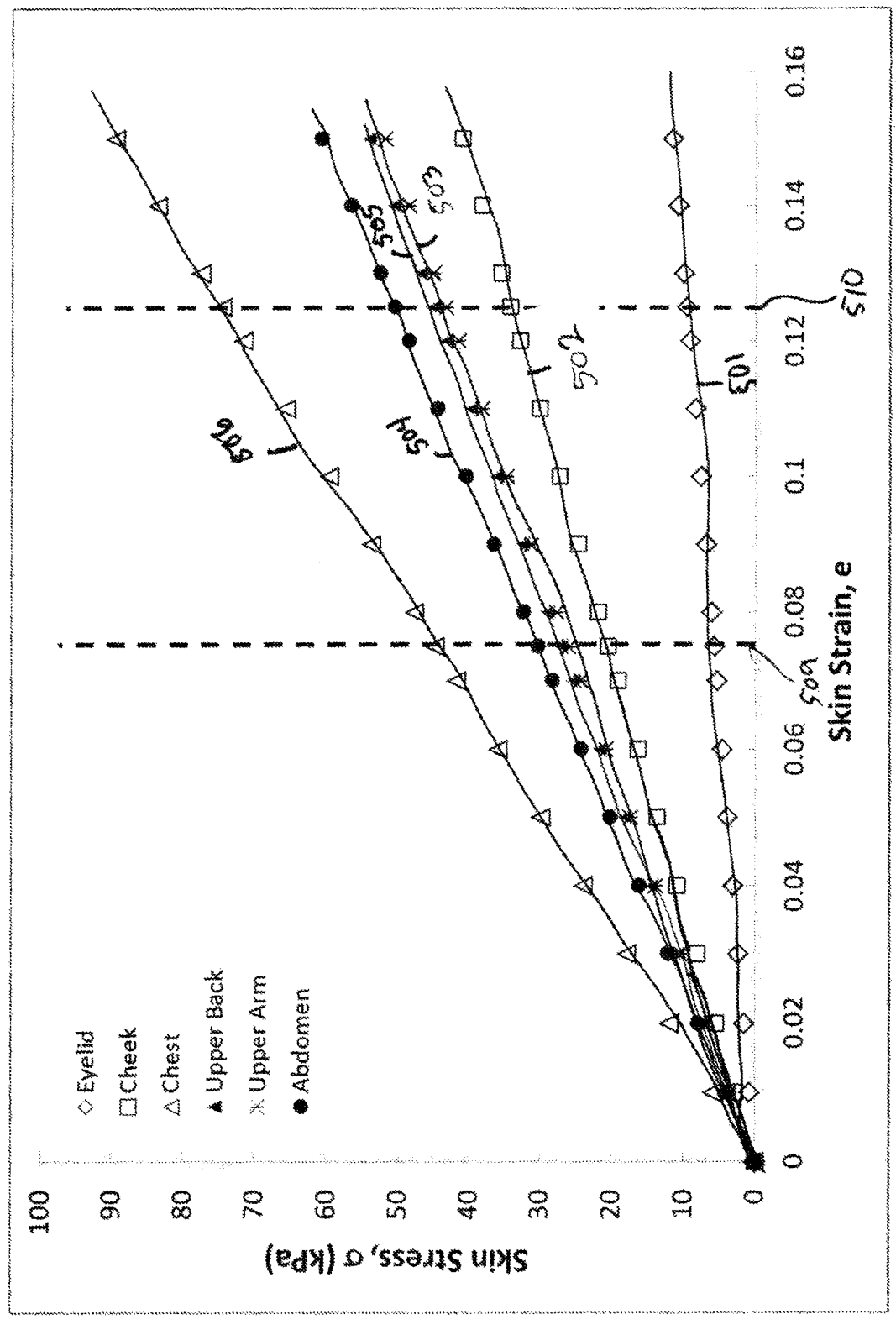

FIGS. 2A1 to 2A6 show the grids prior to application of the skin devices at various skin sites: the eyelid, cheek, upper arm, upper back, abdomen and chest, respectively. FIG. 2B1 to 2B6 show the line deformations at the eyelid, cheek, upper arm, upper back, abdomen and chest, respectively when the skin devices were applied to the noted regions. Arrows indicate direction of device compression.

Digital images were taken of the grids before and after the application of the skin treatment device. Digital image speckle correlation (DISC), a non-contact optical technique, was used to determine strains during loading. Images were taken with the 3D DISC system (Q-400, Dantec Dynamics, Skovlunde, Denmark) and strain maps were generated using Istra 4D software (Dantec Dynamics). Descriptions of such a non-contact technique are described, for example in Marcellier, H., Vescovo, P., Varchon, D., Vacher, P. & Humbert, P. "Optical Analysis of displacement and strain fields on human skin" Skin Res Technol 7, 246-253 (2001), and Staloff, I. A. & Rafailovitch," M. Measurement of skin stretch using digital image speckle correlation" Skin Res Technol 14, 298-303. The measured strain values were used to determine region-specific differences in skin mechanical properties in humans as described below. A variety of different skin zones showed distinct tensional states. As shown in images in FIG. 2B, digital image speckle correlation (DISC) was utilized to study region-specific responses to device application.

Compressive skin strains, $\varepsilon_{skin}$, were calculated based on the DIC analysis, which obtained measured skin strains $\varepsilon_{DIC}$, resulting from the forces imparted on the skin surface by the skin treatment device. These measure skin strains, $\varepsilon_{DIC}$ were: 28.6±0.4, 22.1±0.4, 21.5±0.4, 19±0.2, 20.6±0.5, and 18.8±0.6% for eyelid, cheek, upper arm, upper back, abdomen and chest, respectively (Table 1). These strains were related to the initial and final dimensions of the device by:

$$\varepsilon_{skin} = (I_f - (1+\varepsilon_{Initial})*I_0)/(1+\varepsilon_{Initial})*I_0 \quad (Eq. 1)$$

where $I_0$ is the original length of the device If is the final dimension (length) of the device on the skin at equilibrium, $100*\varepsilon_{Initial}$ is a the initial percent strain of the device when loaded, and $(1+\varepsilon_{Initial})*I_0$ is the length of the device when initially strained.

The device was initially strained at 45% and thus the measured strains were related to the initial and final dimensions of the device as follows:

$$\varepsilon_{DIC} = (I_f - 1.45 I_0)/1.45 I_0 \quad (Eq. 2)$$

The final dimension of the device, If, was related to the initial dimension of the device and the device strain, $\varepsilon_{device}$, at equilibrium by:

$$I_f = I_0 + I_0 \varepsilon_{device} \quad (Eq. 3)$$

Using the equations above, the device strain, $\varepsilon_{device}$, at equilibrium was defined in terms of the skin strain, $\varepsilon_{DIC}$, as:

$$\varepsilon_{device} = 0.45 + 1.45 * \varepsilon_{DIC} \quad (Eq. 4)$$

The various determined device strains at the various locations are set forth in Table 1.

The device strains ($\varepsilon_{device}$) may be used to determine the load (force) per width of the device, ($F_{device}/w$) knowing or approximating the elastic/viscoelastic behavior of the device when strained to a pre-determined amount and then allowed to relax. FIG. 3 illustrates an example of behavior of a particular device during a cycle of loading and unloading. The stress strain curve 300 includes engineering strain versus measured force per width during pre-straining 301 until it is strained to 45% (302) and engineering strain during relaxation 303. These characteristics may vary from device to device, for example, among other things, based on device dimensions, construction, material properties, or material properties over time, the number of times the device is subjected to loading and unloading cycles or other conditions that may affect material properties. A stress strain curve for a device may be obtained using a tensile testing device, a Chatillion (TCD225 system with TLC series load cell, AMETEK, Inc., Largo, Fla., USA). For example, FIGS. 3 and 4 illustrate a stress-strain relationship observed for a device described in Example 1 when loaded by a strain of 45% and then unloaded.

Figure 4:
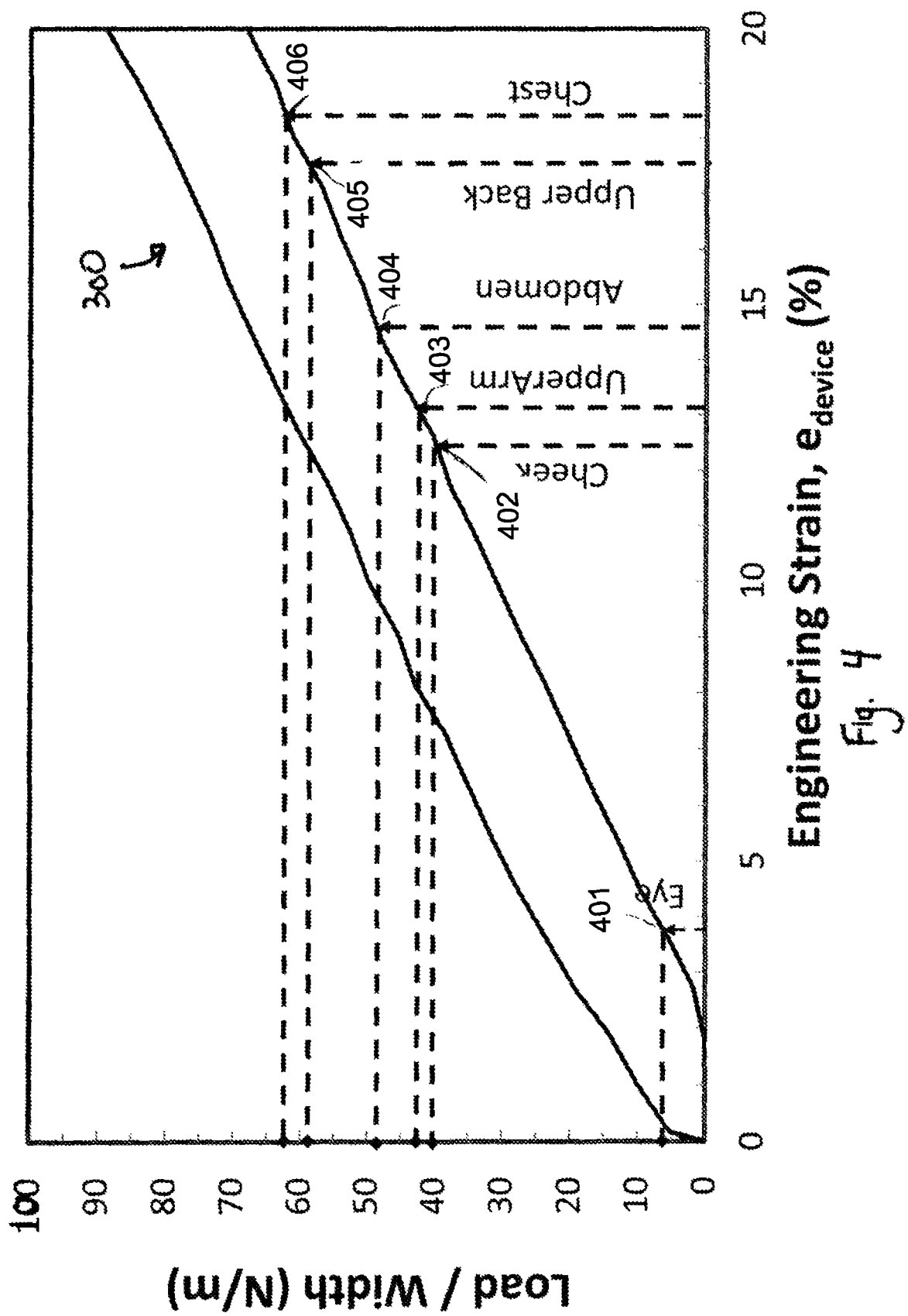
FIG. 4 is an enlarged section of the curve of FIG. 3.

The load per width values at various body locations based on the stress strain curve for the device shown in FIG. 3 and FIG. 4 were determined to be (extrapolated) 5.6±2.4, 42.1±2.2, 45.8±2.7, 50.4±2.5, 58.6±1.2, and 59.7±3.6 N/m for eyelid, cheek, upper arm, abdomen, upper back, and chest, respectively (Table 1).

FIG. 4 illustrates a portion of the stress strain curve 400 for the skin device used in Example 1 during loading 410 and during unloading 420. The load per width of the device when at equilibrium on the eyelid correlates with the measured percent strain of the device on the eyelid at equilibrium 401. The load per width of the device when at equilibrium on the cheek correlates with the measured percent strain of the device on the cheek at equilibrium 402. The load per width of the device when at equilibrium on the upper arm correlates with the measured percent strain of the device on the upper arm at equilibrium 403. The load per width of the device when at equilibrium on the abdomen correlates with the measured percent strain of the device on the abdomen at equilibrium 404. The load per width of the device when at equilibrium on the upper back correlates with the measured percent strain of the device on the upper back at equilibrium 405. The load per width of the device when at equilibrium on the chest correlates with the measured percent strain of the device on the chest at equilibrium 406.

TABLE 1

|  | Skin Strain (%) | Device Strain (%) | Load/Width (Device) (N/m) |
| --- | --- | --- | --- |
| Eyelid | 28.6 ± 0.4 | 3.6 ± 0.6 | 5.6 ± 2.4 |
| Cheek | 22.1 ± 0.4 | 13 ± 0.5 | 42.1 ± 2.2 |
| Upper Arm | 21.5 ± 0.4 | 13.8 ± 0.6 | 45.8 ± 2.7 |
| Upper Back | 19.0 ± 0.2 | 17.5 ± 0.3 | 58.6 ± 1.2 |
| Abdomen | 20.6 ± 0.5 | 15.1 ± 0.8 | 50.4 ± 2.5 |
| Chest | 18.8 ± 0.6 | 17.7 ± 0.9 | 59.7 ± 3.6 |

EXAMPLE 2

In this Example, device strain data and device load (force) per width data from Example 1 were used to determine skin stresses for the eyelid, cheek, upper arm, upper back, abdomen and chest regions as follows:

Using an assumption that the force of the device, Fdevice, adhered to the skin is equal to the force of the skin at equilibrium, the skin stresses, σskin, (at the edge or boundary of the device orthogonal to the force direction) can be determined by:

$$\sigma_{skin} = F_{device}/(w \times t) \quad (Eq. 5)$$

where $F_{device}/w$ is the force per width of the device that correlates with the measured $\varepsilon_{device}$ at equilibrium as the device unloads after being loaded by a certain strain and t is the thickness of the skin.

Skin thicknesses for the eyelid, cheek, upper arm, upper back, abdomen and chest regions were measured using a 10-5 MHz linear array ultrasound transducer (SonoSite M-Turbo, United Medical Instruments, Inc. San Jose, Calif.), as described in Gurtner, G. C., et al. "Improving cutaneous scar by controlling the mechanical environment: large animal and phase I studies", *Ann Sur* 2011; 00:1-9, incorporated in its entirety herein by reference. The measured skin thickness values were: 0.53±0.15, 1.43±0.07, 1.31±0.10, 1.46±0.29, 1.16±0.15, and 1.0±0.14 mm for eyelid, cheek, upper arm, upper back, abdomen, and chest, respectively. According to variations skin thicknesses at other skin regions may be similarly estimated.

In addition to the measured values, published skin thickness values were used to provide an estimated range of thickness values for each region. The skin data used was published in Barker D E (1951) Skin thickness in the human. *Plast Reconstr Surg* 7: 115-116.; Artz C P, Moncrief J A, Pruitt B A Jr (1979) Burns: a team approach. Saunders, Philadelphia, pp. 24-44; and Lee Y, Hwang K (2002) Skin thickness of Korean adults. *Surg Radiol Anat* 24: 183-189.

Figure 5:
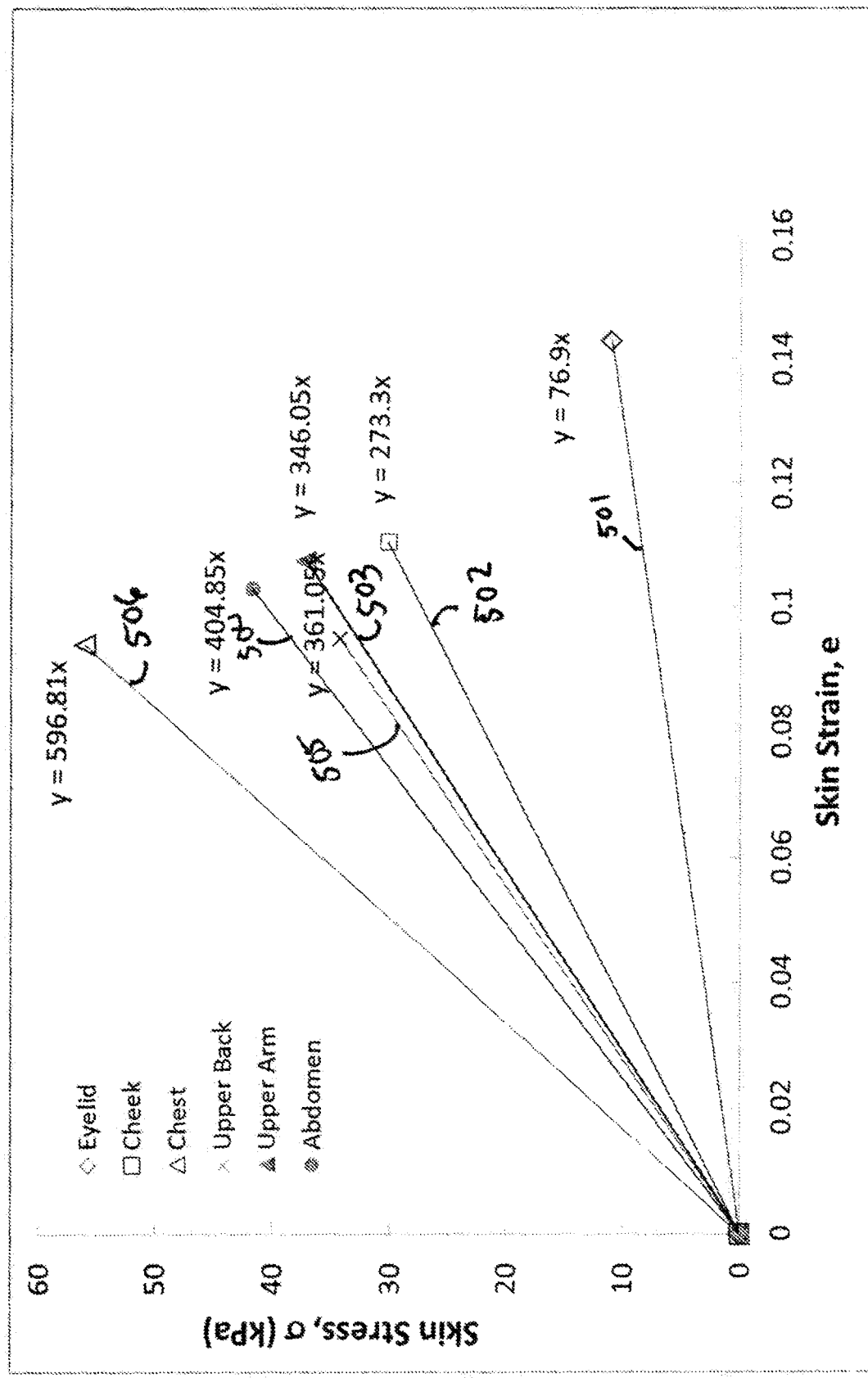
FIG. 5 is a graphical representation of determined skin stress vs. skin strain corresponding to Examples 1, 2, and 3.

Using the average of both measured and published thickness values for a particular region of skin, the stress values were determined. For purposes of a variation herein, it is assumed that the thickness in a region is similar or generally the same from subject to subject within a range. It is further noted that equilibrium of moment forces were not considered in the estimates in this example. Skin stresses determined accordingly are set forth in Table 2 with standard deviations from measured and published thickness values for a particular region of skin. Standard deviations in stress values were calculated taking both the error in force per width and thickness values into consideration. According to variations, skin thicknesses may be measured, estimated using known or published data, or may use both measured and estimated data as described above.

as shown in FIG. 5. Then, the force per width of the skin, $F_{skin}/w$, at the edges of the device for each location was calculated using:

$$F_{skin}/w = \sigma_{skin}/t \quad (\text{Eq. 6})$$

where t is the thickness of skin. Then, using the assumption that the force of the device, $F_{device}$, adhered to the skin is equal to the force of the skin at equilibrium, the force per width of the device, $F_{device}/w$, at equilibrium was calculated using:

$$F_{device}/w = F_{skin}/w \quad (\text{Eq. 7})$$

Then, the device strain data and device load (force) per width data from Example 1 were used to determine the $\varepsilon_{device}$ at equilibrium (after the device unloads after being

TABLE 2

|  | Strain (% compression) | Device Strain (%) | Load/Width (N/m) | Skin Thickness (mm) | Stress (kPa) |
| --- | --- | --- | --- | --- | --- |
| Eye | 28.6 ± 0.4 | 3.6 ± 0.6 | 5.6 ± 2.4 | 0.51 ± 0.13 | 11.0 ± 5.5 |
| Cheek | 22.1 ± 0.4 | 13 ± 0.5 | 42.1 ± 2.2 | 1.39 ± 0.20 | 30.2 ± 4.7 |
| Upper Back | 19.0 ± 0.2 | 17.5 ± 0.3 | 58.6 ± 1.2 | 1.71 ± 0.30 | 34.3 ± 6.0 |
| Upper Arm | 21.5 ± 0.4 | 13.8 ± 0.6 | 45.8 ± 2.7 | 1.23 ± 0.15 | 37.2 ± 5.0 |
| Abdomen | 20.6 ± 0.5 | 15.1 ± 0.8 | 50.4 ± 2.5 | 1.21 ± 0.21 | 41.7 ± 7.7 |
| Chest | 18.8 ± 0.6 | 17.7 ± 0.9 | 59.7 ± 3.6 | 1.06 ± 0.24 | 56.1 ± 12.9 |

EXAMPLE 3

In this example desired initial strain values (the amount of strain in the device prior to its application on skin) of the device in Example 1 were estimated or approximated. A desired range of resulting skin strain values between 15% and 25% resulted in estimated desired initial strains for various regions using the device described in Example 1. The desired initial strain for the eyelid ranged from 21% to 38%. The desired initial strain for the cheek was about between 23% and 45%. The desired initial strain for the abdomen was about between 31% and 57%. The desired initial strain for the chest was about between 34% and 64%.

The desired initial strain values were determined by plotting the stress vs. strain at the edges of the dressing for each skin location as shown in FIG. 5. An assumption was made that for purposes of estimating the initial strain value, the stress vs. strain behavior of skin is linear at lower values of stress and strain. This is a valid assumption for typical strain values experienced with physiological loading conditions (<20%). It was further assumed that the tensile strain at the edges of the device parallel to the strain direction was ½ of the compressive strain imparted to the skin by the device. The approximated linear curves for each skin zone are shown respectively as eyelid 501, cheek 502, upper arm 503, abdomen 504, upper back 505 and chest 506.

As shown in FIG. 6, using the stress strain curve, the skin stress, $\sigma_{skin}$, values that would be experienced at the edges of the device when skin strains of 15% to 25% (shown as lines 509, 510 respectively) were imposed on eyelid, cheek, upper arm, abdomen, upper back and chest skin were extrapolated using the estimated linear curves for each skin area (respectively eyelid 501, cheek 502, upper arm 503, abdomen 504, upper back 505 and chest 506) skin or zone loaded by a certain strain) that correlates with the force per width of the device for each body location. Finally, the desired initial device strain, $\varepsilon_{Initial}$, which would impart the $\varepsilon_{device}$ at equilibrium, was determined for a range of resulting skin strain values, $\varepsilon_{skin}$, between 15% and 25% for each body location by plugging Eq.3 to Eq.1 and solving for $\varepsilon_{initial}$:

$$\varepsilon_{initial} = (\varepsilon_{device} - \varepsilon_{skin})/(1 + \varepsilon_{skin}) \quad (\text{Eq. 8})$$

Table 3 illustrates exemplary calculations of a desired initial device strain for the device described in Example 1.

EXAMPLE 4

Figure 8:
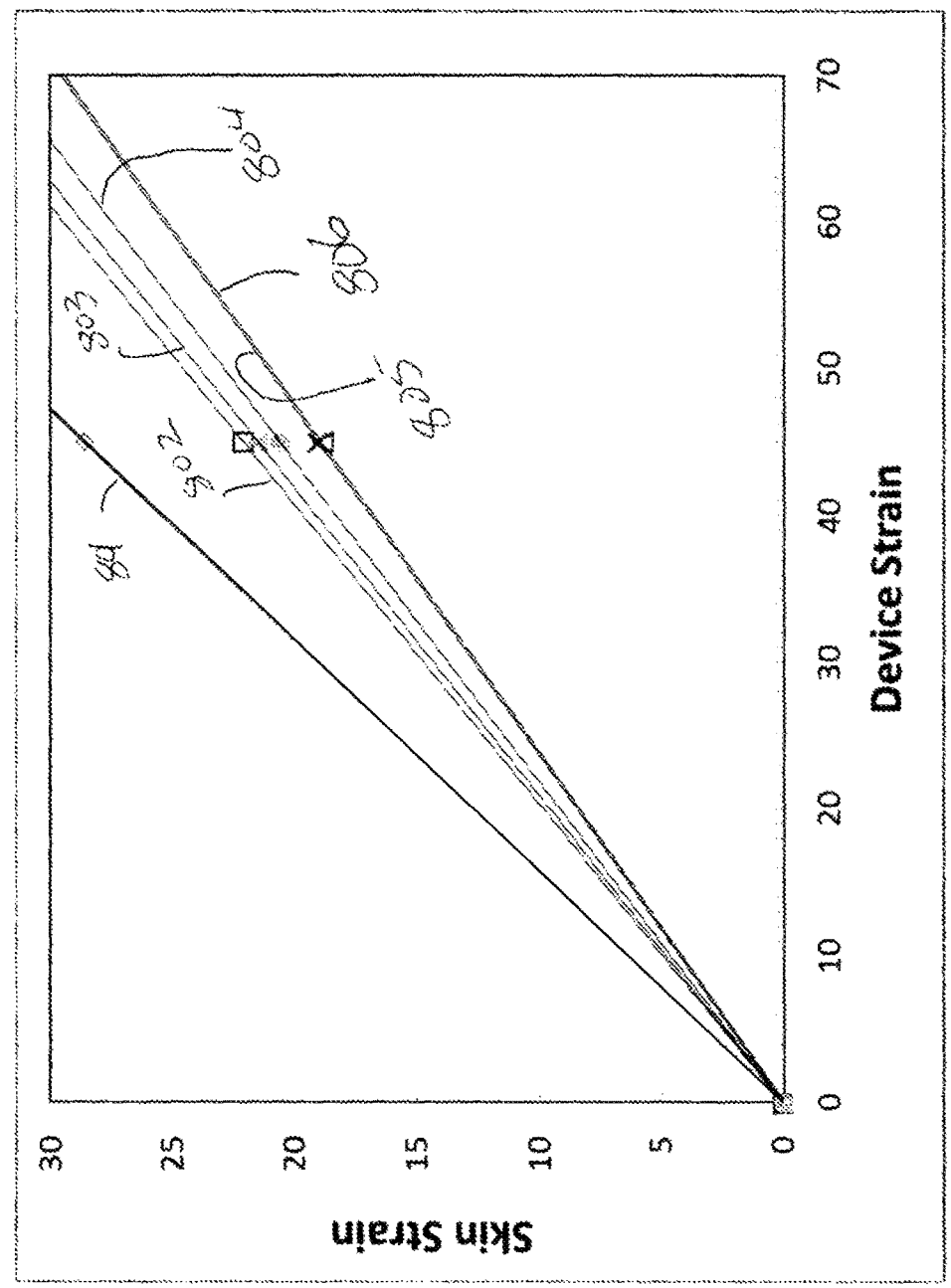
FIG. 8 is a graphical representation of approximate initial device strain versus skin strain for various body regions corresponding to Example 4.

Additionally or alternatively to estimating desired initial strain values, as described in Example 3, initial strain values (the amount of strain in the device prior to its application on skin) of the device in Example 1 may be estimated or approximated, for example using the curves shown in FIG. 8.

As shown in FIG. 8 curves 801, 802, 803, 804, 805, 806 for initial device strain versus skin strain were generated respectively for eyelid, cheek, upper arm, abdomen, upper back and chest by plotting the measured skin strain values at an initial device strain of 45% as set forth in Tables 1 and 3. An assumption is made that an approximately or generally linear relationship exists between resulting skin strain and initial device strain. As further shown in Table 3 initial device strain values for the various body regions or locations may be extrapolated from the curves 801-805 at desired final strain values, e.g. between 15% and 25% skin strain.

TABLE 3

| Body Region or Location | Skin Strain (inside) (% compression) | Skin Strain (outside) (% tension) | Skin Stress (outside) (kPa) | Skin Thickness (average) (mm) | Load/Width (average) (N/m) | Final Device Strain (%) | Initial Device Strain Ex. 3 (%) | Initial Device Strain Ex. 4 (%) |
|---|---|---|---|---|---|---|---|---|
| Eyelid | 15 | 7.5 | 5.8 | 0.51 | 2.9 | 3 | 21.2 | 24 |
|  | 25 | 12.5 | 9.6 | 0.51 | 4.9 | 3.5 | 38.0 | 39.5 |
| Cheek | 15 | 7.5 | 20.5 | 1.39 | 28.5 | 9.4 | 28.6 | 30 |
|  | 25 | 12.5 | 34.2 | 1.39 | 47.5 | 14.2 | 52.3 | 51 |
| Upper Back | 15 | 7.5 | 27.1 | 1.71 | 46.3 | 14.0 | 34.1 | 36 |
|  | 25 | 12.5 | 45.1 | 1.71 | 77.2 | 22.6 | 63.4 | 60 |
| Upper Arm | 15 | 7.5 | 26.0 | 1.23 | 26.0 | 10.3 | 29.7 | 31.5 |
|  | 25 | 12.5 | 43.3 | 1.23 | 43.3 | 16.0 | 54.6 | 52.5 |
| Abdomen | 15 | 7.5 | 30.4 | 1.21 | 36.7 | 11.4 | 31.1 | 33 |
|  | 25 | 12.5 | 50.6 | 1.21 | 61.2 | 18.0 | 57.3 | 55 |
| Chest | 15 | 7.5 | 44.8 | 1.06 | 47.4 | 14.2 | 34.4 | 66 |
|  | 25 | 12.5 | 74.6 | 1.06 | 79.1 | 23.1 | 64.1 | 60 |

In accordance with variations of the invention, a skin treatment device may be selected with desired mechanical or force properties based on the location where the skin treatment device is to be applied and/or other demographic or individual patient information.

According to variations, the characteristics of the location where the skin treatment device is to be applied may be determined, estimated or approximated using one of a variety of methods. For example such methods or techniques may include but are not limited to: measuring, determining, estimating or approximating a relative amount of skin tension or stiffness using a device (for example, device 100 described with respect to FIG. 1A to 1F or other pressure suction devices, or acoustics); measuring, determining, estimating or approximating relative inherent skin stress by observing skin characteristics such as stresses, skin strain after application of a skin treatment device; using measured or published data; and/or further characterizing the skin based on patient demographic information. According to some variations measurements of pre-surgical areas may be correlated with post-surgical properties of the skin of the area.

According to variations properties of a device or devices may exhibit one or more desired force properties (that may be location, patient or demographic dependent) such as, load per width of the device at equilibrium, initial strain of the device, or strain or stress imparted to the skin of a particular location by the device.

The desired force property or properties may be determined, estimated or approximated in a variety of manners.

According to variations of the invention, force properties of a device may be selected based on relative stresses, stiffness or tension, of the region of skin. For example for the stiffer regions or regions with higher stresses or tension, a skin device with greater initial device strain, greater load per width or other properties may be selected. For example for the less stiff, lower stress, lower tension regions, a skin device with less initial strain, less load per width force or other properties may be selected. For example, a skin device may be selected to unload at least a portion of the skin tension or stresses at a particular region, location or area. A skin stiffness, stress or tension characteristic of a skin region may also be based on its actual or approximated or relative stiffness, stress or tension with respect to other locations within a range of skin strains. A relative stiffness, stress, or tension may be based on a comparison from skin region to skin region, from subject to subject, and/or based on a comparison of a standard with respect to a subject.

According to variations, a device may be selected from one or more devices with different force properties or levels of force properties. One or more of the plurality of device property categories may be selected to better fit a particular skin region and/or a particular subject based, for example on actual, approximated or relative skin stiffness, stress or tension characteristics.

For example, a relatively stiffer (determined by force/width) region may use a device that is strained in an amount that provides a force/width of about 45 to 80 N/m. A region with a relatively upper mid-range stiffness region may use a device that is strained in an amount that a force/width of about to 35 to 65 N/m. A region with a relatively upper mid-range stiffness region may use a device that is strained in an amount that a force/width of about to 25 to 45 N/m. A relatively less stiff region may use a device that is strained in an amount that provides a force/width of about 1 to 25 N/m. These load per width values may vary substantially based on region of skin, particular factors related to an individual subject, or type of treatment provided by the skin treatment device.

These regions or other mechanically differentiated skin regions described herein may be generally identified using a device such as device 100 where a stiffer region might be indicated by B, relatively less stiff region by C and an even lesser stiff region by D.

As an additional example, for a chest or upper back region a device may exhibit a relatively greater stiffness. For example, a cheek or abdomen region may exhibit a relatively mid-range stiffness. For example, for an eyelid region may exhibit a relatively less stiff region Different devices may be selected for these different regions.

According to some variations, at a given region, a device may be used that provides a desired or sufficient stress off-loading for a particular application. As an additional example a device with relatively greater stress offloading mechanical properties may be selected or used for a region with relatively greater skin tension or stiffness; a device with relatively mid-range stress off-loading mechanical properties may be selected or used for a region with relatively mid-range skin tension or stiffness; and/or a device with relatively less stress off-loading mechanical properties may be selected or used for a region with relatively less skin tension or stiffness.

As an example a device with relatively greater stress offloading mechanical properties may be selected or used for the chest or upper back region; a device with relatively mid-range stress off-loading mechanical properties may be selected or used for the abdomen cheek region; and/or a device with relatively less stress off-loading mechanical properties may be selected or used for the eyelid region.

According to variations for a desired skin strain or range of skin strain amounts, an initial strain of a device may be selected. For example a resulting skin strain of between about 10% and 30%, between 15% and 25% or between 18% and 23% or for any strain or given range of strains may be desired. The initial strain value may be determined, approximated or estimated for example as described with respect to Example 3 herein.

According to variations an initial device strain may be selected from within one or more ranges. For example the one or more ranges may be from about 20% to 40%; from about 25% to about 55%; and/or from about 30 to about 65%; or number ranges within these ranges. An applicator or tensioning device may have one or more strain values selectable based on the region or other characteristic of a skin region to which it is to be applied.

For example for a range of resulting skin strain of between 15% and 25% using a device similar to that described in Example 1, for an eyelid, an initial device strain may be between approximately 21% to 40%; for a cheek approximately 28% to 53%; for an upper back 34% to 64%; for an upper arm 29% to 55%; for an abdomen 31% to 58%; for a chest region about 34% to 65%. These numbers may be adjusted based on slippage resulting from adhesive slippage of the adhesive used to apply the dressing to the skin. The slippage for a particular adhesive may be determined a number of ways including by empirical observation.

According to a variation, curve generally representing the force versus strain of a particular skin device (see e.g. FIG. 3) during loading and unloading may be used to identify or select a desired device with desired device properties. A characteristic curve of a skin device may be used to approximate or determine the load per width of the skin treatment device, device strain, skin strain, and/or stress value, when the device is strained to a given level, applied to skin and allowed to reach a force equilibrium. For example, knowing device strain levels at equilibrium at a particular location of a subject's skin, load per width of the device at equilibrium can be estimated using the characteristic curve for the device at a particular initial pre-strain. It is noted that the characteristic curve may vary from device to device; may vary after repeated cycles of loading and unloading and may vary depending on the amount the device is strained during loading. In some variations, it may be assumed that the curve is similar for some levels of strain.

According to variations, a user may select a skin treatment device from a plurality of skin treatment devices, each having different force properties when strained a given or set amount. A tensioning device, stretching device or applicator that pre-strains a device a preset amount may then be used to pre-strain any one of the selected devices. For example when applied to a particular location, a first device when strained the pre-set amount may provide a lower load per width at equilibrium or may provide less skin strain at equilibrium while a second device when strained the pre-set amount may provide a greater load per width at equilibrium or a greater skin strain at equilibrium than the first device.

The ranges of desired force properties described herein may be adjusted for individual patients. Such adjustments may be based on factors such as relative stiffness, stress or tension measurements, for example, using the device 100 described herein; based on one or more individual factors, based on a subject's irritation or other response to skin stresses, based on desired outcome or use of the skin treatment device which may include but is not limited scar amelioration or prevention.

While these various methods shown may be used to approximate device properties, other methods are contemplated herein. For example, the modulus of elasticity of skin may be determined by obtained observing the skin strain using a device at a plurality of initial strain levels. Values determined may be confirmed or further approximated with a variety of measurements or experimentation.

FIGS. 9A to 9D illustrate a variation of a skin tension measuring or determining device 900 comprising an elastomer sheet 905 having known mechanical properties. (For example the elastic/viscoelastic behavior of the sheet or device may be known or approximated as described with respect to FIG. 3 herein, and various mechanical properties, (e.g., stress/strain or elastic properties) may be determined as described herein with reference to FIGS. 3 to 8). The mechanical properties may be similar to that of a dressing described herein or may be different. The mechanical properties may also be selected to be generally similar or close to that of skin.

The sheet of material 905 has a skin adhesive 911 on a skin interfacing side 910. An adhesive liner may be provided over the skin adhesive prior to or after straining the elastic sheet. Strain indicators comprising parallel line bars 915 are stamped, printed or otherwise drawn on an opposing side 906 of the sheet 905, or on side 910 under adhesive layer 911, or may be formed by an embedded structure or material such as a fabric thread or polymer material extruded within the elastic sheet. The parallel line bars 915 are separated a distance, d1 when the sheet is in an unstrained configuration. The device 900 may include attachment structures 907, 908 configured to attach to a tensioning device that may be used to exert a tensile force to strain the sheet 905 between the attachment structures 907, 908. The sheet 905 may be strained a predetermined amount using a tensioning device or applicator, for example shown in FIG. 16 herein or as described in a manner as, for example, set forth in U.S. application Ser. No. 12/854,859 or 13/345,524 with respect to dressings or elastic sheets, incorporated in their entirety herein by reference. The sheet may also be prestrained and stored in a prestrained configuration such as that illustrated in FIG. 9B. Examples of strained elastic sheet or dressing methods and devices are described in described in U.S. application Ser. No. 13/552,521 incorporated in its entirety herein by reference. When the sheet 905 is strained a desired amount before adhering the sheet to the skin, the distance between the bars 915 increases, e.g., shown in FIG. 9B as d2. The strained sheet 905 may be adhered to the skin. When the sheet is applied to the skin location it may be allowed to at least partially recover to its base configuration until a dynamic equilibrium between the tensile stress in the skin and the elastic material of the sheet is reached. FIG. 9C shows a possible resulting distance d3 between the parallel line bars after the device 900 is adhered to skin and an equilibrium has been established. The amount of inherent skin tension may be proportional or related to resulting strain between line bars 915(d3) with respect to the original strain (d2) between the line bars. The distances d1 and d2 may be predetermined and the distance (d3) may be measured to determine desired strain in a dressing or to select a dressing as further described herein. The greater the value of d3, the more inherent stress is in the skin at the measurement location. Thus a dressing or dressing property may be selected using the device 900 in a manner similar to that described with respect to the use of skin tension measuring device 100. For example, for the stiffer regions or regions with higher stresses or tension, i.e. a relatively higher d3 value, a skin device with greater initial device strain, greater load per width or other properties may be selected. For example, for the less stiff, lower stress, lower tension regions, i.e., a relatively lower d3 value, a skin device with less initial strain, less load per width force or other properties may be selected.

Figure 10B:
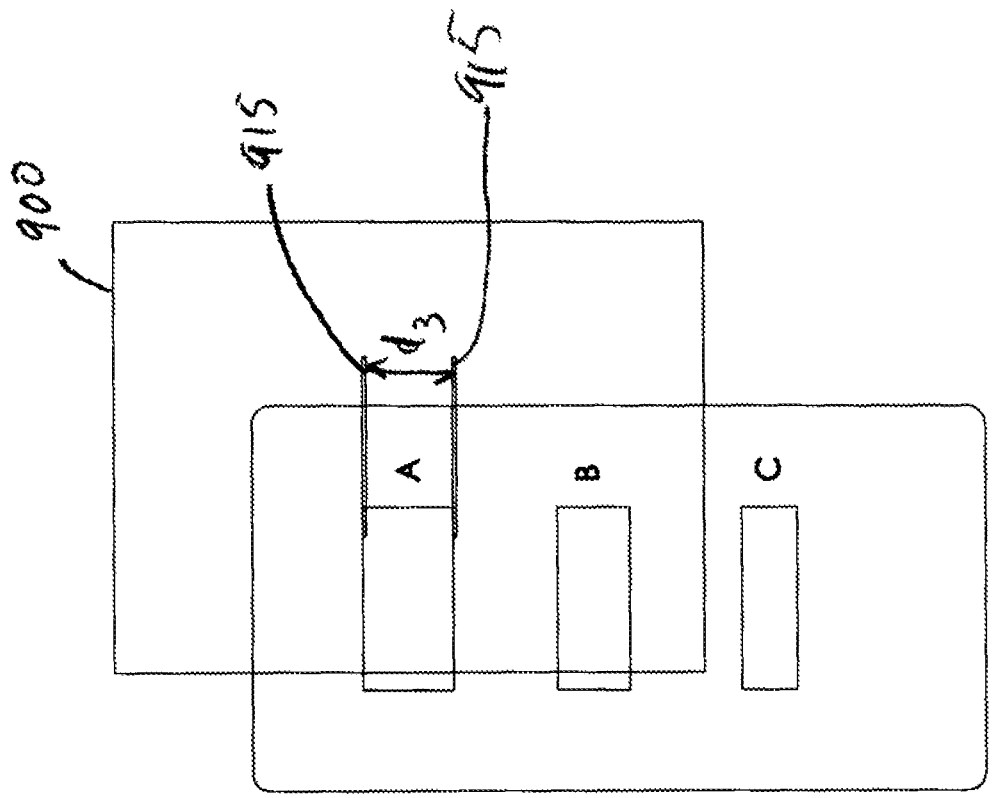
FIG. 10B is the diagnostic sheet of FIG. 10A in a strained configuration.
Figure 10A:
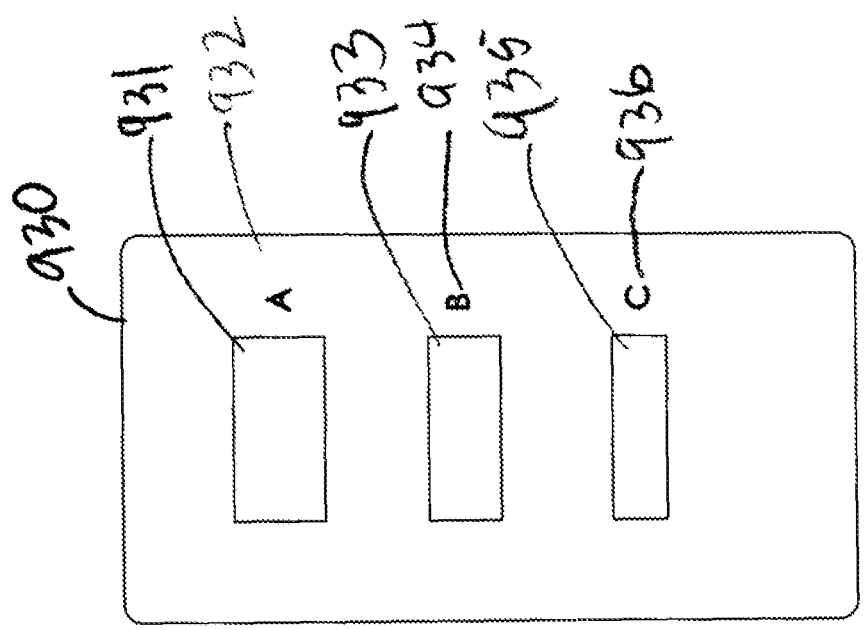
FIG. 10A is a diagnostic elastic sheet in a first unstrained configuration.

FIGS. 10A and 10B illustrate a measurement device 930 that may be used to analyze the resulting distance d3 the elastic sheet 905 as shown in FIG. 9A. The measurement device may comprise a card having a plurality of windows or openings 931, 933, 935 having sizes corresponding to dressing types or properties (including but not limited to a percent or amount of strain to be applied to a particular dressing) that may be selected, A, B, and C, 932, 934, 936, respectively. For example, if the distance d3 established by line bars 915 is greater than or about the size of opening 931, dressing type or properties A 932 may be selected. If the line bars 915 fits within the window 933 but not within window 935, the dressing type or properties B may be selected. If the line bars fit within window 935 then dressing type or properties C may be selected. Dressing type or properties A provide greater tension or load per width in skin; dressing type or properties B provide a mid-range tension level or load per width in skin between A and C, and dressing type or properties C provide tension level or load per width in skin that is less than A and B. As noted above, the properties A, B, and C may represent a strain level to be applied to a dressing as well as a dressing to be applied to a particular skin location.

FIGS. 11A to 11C illustrate a variation of a skin tension measuring device 950 comprising an elastomer sheet 955 having known stress and strain properties. (For example the elastic/viscoelastic behavior of the sheet or device may be known or approximated as described with respect to FIG. 3 herein, and various stress strain properties may be determined for example, as described herein with reference to FIGS. 3 to 8). The sheet of material 955 may have a skin adhesive on a skin interfacing side like that shown in FIG. 9D. Strain indicators comprising a rectangular cutout 965 defined by length lines 977 and parallel width lines 976. (The rectangles may also be printed, stamped, drawn or embedded.) The parallel length lines 977 are separated a distance l1 when the sheet 955 is in an unstrained configuration and the parallel width lines 976 are separated a distance w1 when the sheet 955 is in an unstained configuration. The device 950 may include attachment structures 956, 957, 958. 959 configured to attach to a tensioning device that may be used to exert a bidirectional or biaxial tensile force to strain the sheet 955 between the attachment structures 956, 957 and between attachment structures 958, 959. FIGS. 14A to 14D describe a multiaxial tensioning device or applicator that may be used to strain the sheet 955. The sheet 955 may be strained a predetermined amount in a manner as for example set forth in U.S. application Ser. No. 12/854,859 or 13/345,524 incorporated in its their entirety herein by reference. The sheet may also be prestrained and stored in a prestrained configuration. Examples of strained elastic sheet or dressing methods and devices are described in described in U.S. application Ser. No. 13/552,521, incorporated by reference in its entirety herein.

When the sheet 955 is strained a desired amount between the length lines, before adhering the sheet 950 to the skin, the distance between the length lines 977 increases, e.g., shown in FIG. 11B as l2. When the sheet 955 is strained a desired amount before adhering the sheet to the skin, the distance between the width lines 976 increases, e.g., shown in FIG. 11B as w2. The sheet 955 may be adhered to the skin. When the sheet 955 is applied to the skin location it may be allowed to at least partially recover to its base configuration until a dynamic equilibrium between the tensile stress in the skin and the elastic material of the sheet 955 is reached. FIG. 11C shows possible resulting distances l3 and w3 between the length lines 977 and width lines 976, respectively, after the device 950 is adhered to skin and equilibrium has been established. The amount of inherent skin tension transverse to lines 976 may be proportional or related to resulting length between lines 976 (l3). The amount of inherent skin tension transverse to lines 977, may be proportional or related to resulting length between lines 977 (w3) with respect to the original distance (w2) between the width lines. The distances l1 and l2 may be predetermined and the distance l3 may be measured to determine desired strain in a dressing or to select a dressing as further described herein. The distances w1 and w2 may be predetermined and the distance w3 may be measured to determine desired strain in a dressing or to select a dressing as further described herein. The greater the value of l3 the more inherent stress is in the skin at the measurement location in a direction transverse to the length lines 976. The greater the value of w3 the more inherent stress is in the skin at the measurement location in a direction transverse to the width lines 977. Thus a dressing or dressing property may be selected using the device 950 in a manner similar to that described with respect to the use of skin tension measuring device 100. Either or both of the strain values in biaxial directions may be selected for example based on the direction of greatest inherent skin stress. The relative amount of strain in one direction versus the transverse direction may be used to orient the incision line in a direction where lower stresses are exerted on a healing wound.

Figure 12C:
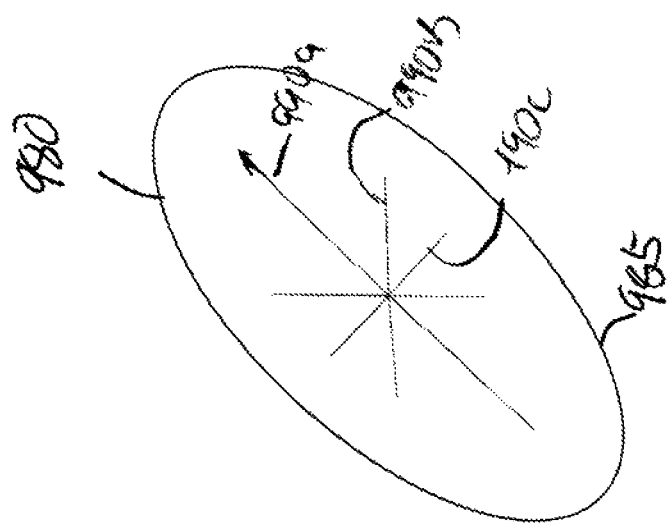
FIG. 12C is the diagnostic sheet of FIG. 12B after it has been applied to a skin surface.
Figure 12B:
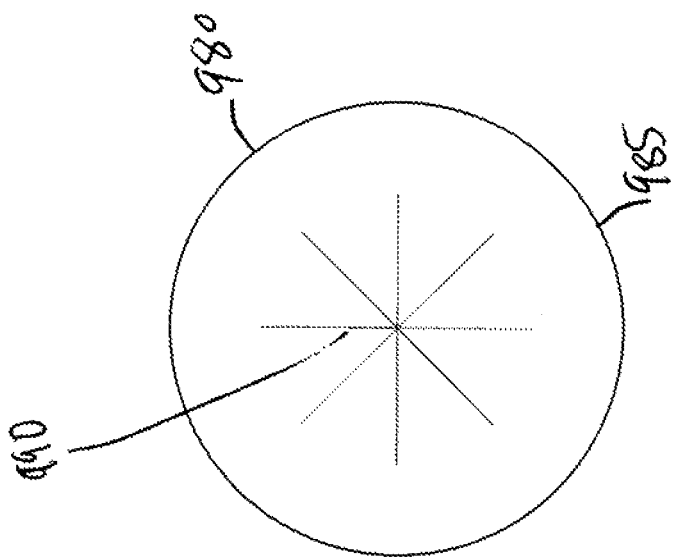
FIG. 12B is the diagnostic sheet of FIG. 12A in a strained configuration.
Figure 12A:
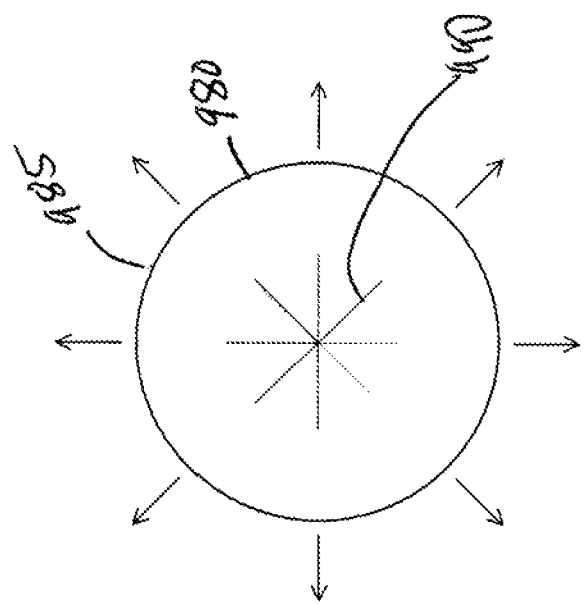
FIG. 12A is a diagnostic elastic sheet in a first unstrained configuration.

FIGS. 12A to 12C illustrate a variation of a skin tension measuring device 980 comprising an elastomer sheet 985 having known stress and strain properties. (For example the elastic/viscoelastic behavior of the sheet or device may be known or approximated as described with respect to FIG. 3 herein, and various stress strain properties may be determined for example, as described herein with reference to FIGS. 3 to 8). In addition to identifying a type or property of a dressing to be applied. The device may be used to identify desired orientation of a surgical incision. The sheet of material 985 may have a skin adhesive on a skin interfacing side like that shown in FIG. 9D. The sheet of material may be in a circular or other arcuate shape and may be radially strained with attachment structures coupled to the elastic sheet in a manner as described with respect to FIGS. 15A to 15H herein Strain indicators comprise a plurality of radial lines 990 that may intersect the center of the circle. The lines 990 may be printed, stamped, drawn or embedded on or in the sheet 985. The radial lines 990 are symmetrical when the sheet is in an unstrained configuration. The sheet may also be prestrained and stored in a prestrained configuration before use. Examples of strained elastic sheet or dressing methods and devices are described in U.S. application Ser. No. 13/552,521 incorporated by reference in its entirety herein.

When the sheet 985 is radially strained a desired amount, before adhering the sheet 985 to the skin, the lines 990 remain symmetrical as shown in FIG. 12B. When the sheet 985 is applied to the skin location it may be allowed to at least partially recover to its base configuration until a dynamic equilibrium between the tensile stress in the skin and the elastic material of the sheet 985 is reached. FIG. 12C shows a possible resulting configuration of the lines 990 after the device 980 is adhered to skin and an equilibrium has been established. The length of the line 990a in a first orientation is greater than the length of the line 990c transverse to the line 990a. Line 990c is the shortest. The length of the line 990b at 45 degree angle with respect to lines 990a and 990c has a length between that of line 990a and 990c. Thus the inherent stresses in the direction of line 990a are the greatest. Accordingly an incision line may be selected to be in the direction or the greatest skin tension or in an orientation orthogonal to the direction of least amount of tension, so that the tension on a healing incision wound may be reduced or minimized.

FIGS. 13A to 13C illustrate a variation of a skin tension measuring device 1980 comprising an elastomer sheet 1985 having known stress and strain properties. (For example the elastic/viscoelastic behavior of the sheet or device may be known or approximated as described with respect to FIG. 3 herein, and various stress strain properties may be determined for example, as described herein with reference to FIGS. 3 to 8). In addition to identifying a type or property of a dressing to be applied. The device may be used to identify desired orientation of a surgical incision.

The sheet of material 1985 may have a skin adhesive on a skin interfacing side like that shown in FIG. 9D. The sheet of material may be in a circular shape and may be radially strained in a manner as described with respect to FIGS. 15A to 15H herein. A strain indicator comprises a circle or other indicator mark 1990. The indicator mark 1990 may be printed, stamped, drawn or embedded on or in the sheet 1985. The mark 1990 may be symmetrical when the sheet 1985 is in an unstrained configuration. The sheet 1985 may also be prestrained and stored in a prestrained configuration before use. Examples of strained elastic sheet or dressing methods and devices are described in described in U.S. application Ser. No. 13/552,521, which is incorporated by reference in its entirety herein.

When the sheet 1985 is radially strained a desired amount, before adhering the sheet 1985 to the skin, the mark 1990 may remain symmetrical as shown in FIG. 13B. When the sheet 1985 is applied to the skin location it may be allowed to at least partially recover to its base configuration until a dynamic equilibrium between the tensile stress in the skin and the elastic material of the sheet 1985 is reached. FIG. 13C shows a possible resulting configuration of the mark 1990 after the device 1980 is adhered to skin and an equilibrium has been established. The shape of the mark is oblong in a direction or along axis D of greatest skin tension. Accordingly an incision line may be selected to be in the direction or along axis D of the greatest skin tension so that the tension on a healing incision wound may be reduced or minimized.

Measurement devices (as depicted in exemplary FIGS. 10A and 10B)) may be used to analyze the resulting distance along the short axis of the oblong, axis E. As noted above, the properties A, B, and C may represent a strain level to be applied to a dressing or a dressing to be applied to a particular skin location).

Figure 14A:
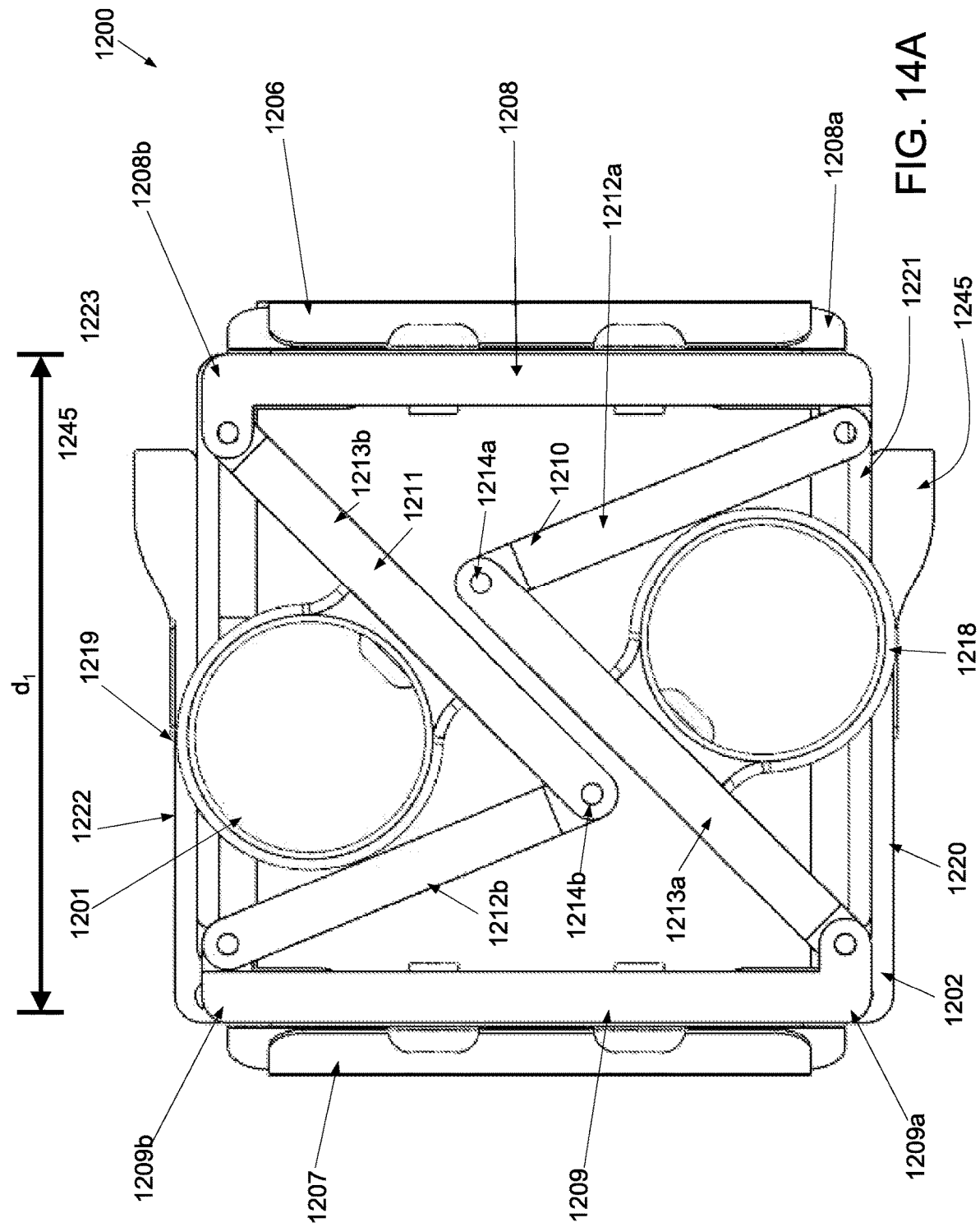
FIG. 14A is a superior view of an applicator in an unstrained configuration.
Figure 14B:
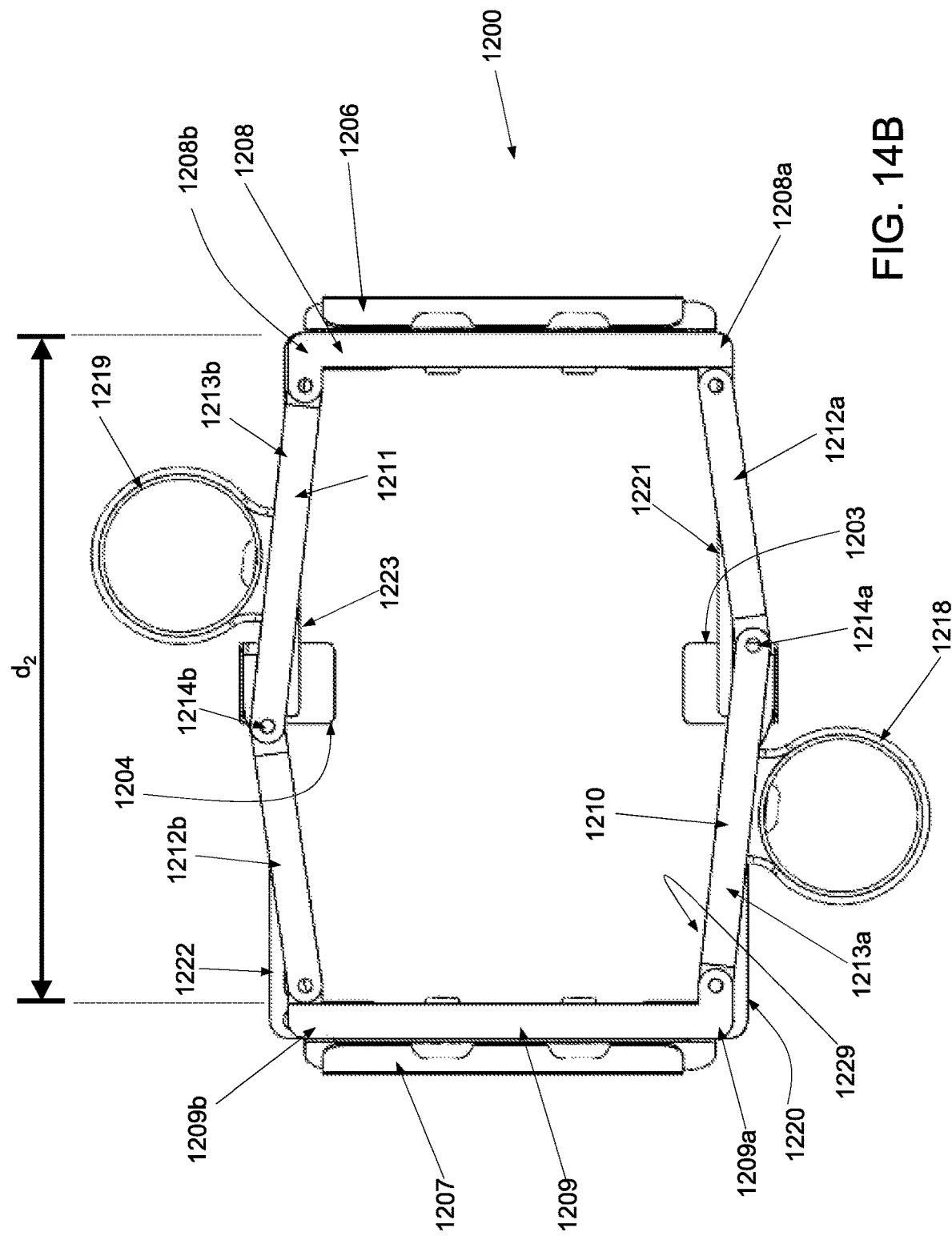
FIG. 14B is a superior view of the applicator of FIG. 14A in a strained configuration.

FIGS. 14A to 14D illustrate a variation of a tensioning device, straining device or an applicator 1200. The device 1200 may be used to tension and apply a diagnostic device as described herein with respect to FIGS. 11A to 11C (as well as to apply a dressing). The applicator 1200 comprises a handle 1201 or actuator configured to be actuated to strain a skin device and/or to apply the device to the skin of a subject. The applicator 1200 includes end attachment structures 1206, 1207. In some variations, the applicator may also include side attachment structures 1203, 1204, 1220, 1222 that may interface with structures 1203 and 1204 be attached to the sides of a skin device. This interface may provide a second dimension or axis to the tension or strain applied to the skin device. Thus the skin device may be strained in orthogonal directions or at least two directions, i.e., the applicator provides a bi-directionally or multi-directionally strained skin treatment device. The attachment structures may be located on the bottom of bump features 1245 on wall segments 1220, 1222. The attachment structures 1206, 1207 may comprise engagement flaps having edges that engage attachment features 1246, 1247 of a corresponding skin device 1240. Attachment structures 1203, 1204 as shown are hook or loop structures that have corresponding hook or loop structure attachment features on the back side of the skin device. The applicator or skin treatment device attachment structures may comprise other types of attachment structures The applicator 1200 may further comprise moveable, slidable or a collapsing or expanding bottom frame structure 1202, opposing fixed configuration walls 1208, 1209 and opposing movable, pivotable or hinged walls 1210, 1211. Frame structure comprises a pair of slidable elements 1220, 1221 and pair of slidable elements 1222, 1223. Each of the pair of slidable elements 1220, 1221 and 1222, 1223 can slide together into a closed position (FIGS. 14A and 14C) where there is a first distance d1 between walls 1208 and 1209. The pairs of slidable element 1220, 1221 and 1222, 1223 can slide apart into a second open or strained position where there is a second distance d2 between the walls 1208, 1209 and where the distance d2 is greater than the distance d1 (as depicted in FIGS. 14B and 14A, respectively).

Hinged wall 1210 comprises first and second wall portions or segments 1212a, 1213a that are movably, pivotally or hingedly connected to each other by connector 1214a, at a pivot point. Hinged wall 1211 comprises a first and second wall segments 1212b, 1213b that are movably, pivotally or hingedly connected to each other by connector 1214b at a pivot point. Wall segments 1212a and 1213b are movably, pivotally or hingedly coupled respectively to opposite end sides 1208a, 1208b of wall 11081208. Wall segments 1212b and 1213a are movably, pivotally or hingedly coupled respectively to opposite end sides 1209b, 1209a of wall 1209. The walls 1208, 1209, 1210, 1211 are coupled to the frame structure 1202 to form a box-like structure with an opening (when in the strained configuration) to provide access to a skin treatment device 1240 attached across the bottom of the applicator to attachment structures 1203, 1204, 1206, 1207, 1246, 1247. This access allows a user to apply pressure to a skin treatment device as or after it is applied to a skin surface, before removing the applicator 1200 from the skin treatment device. Alternatively, a pressure application device may be coupled to the applicator and actuable to provide pressure through the opening to a skin treatment device as or after it is being applied.

FIGS. 14A and 14C illustrate the applicator 1200 in a first, unstrained position. The frame structure 1202 is in an unstrained position where slidable elements 1220, 1221 and slidable elements 1222, 1223 are in a closed position. Wall segments 1212a and 1213a are pivoted to form a v-shape collapsed into the box structure of the applicator 1200, and opposing wall segments 1212b and 1213b are pivoted to form a v-shape collapsed into the box so that the distance between end walls is a distance d1. This position facilitates loading of an unstrained skin treatment device onto the applicator 1200.

After an unstrained device is loaded, the skin treatment device is strained by applying opposing, outward forces to pulling rings 1218, 1219, respectively attached to wall segments 1213a, 1213b. This force straightens side walls

Figure 14D:
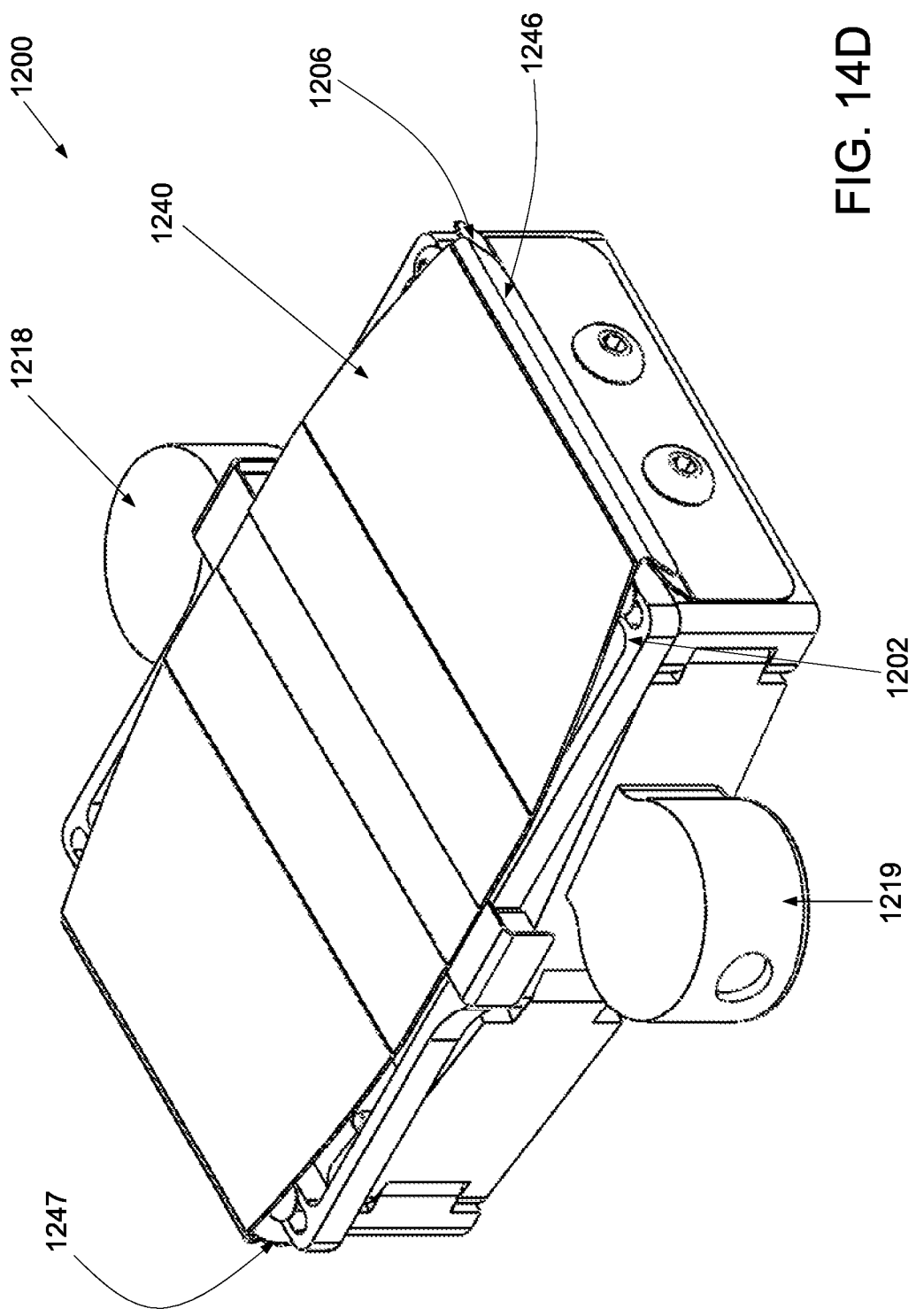
FIG. 14D is an inferior perspective view of the applicator of FIG. 14A in a strained configuration.

1210, 1211 and pairs of sliding elements 1220, 1221 and 1222, 1223 into an elongated or open position as shown in FIGS. 14B and 14D, thus transferring a separation force to the skin treatment device to strain the skin treatment device widthwise (relative to its orientation and use on along a length of an incision). In other variations, a single collapsible wall attached generally about the midpoints of the fixed configuration walls so only a single pulling force is used to separate the fixed configuration walls.

When the device is in the strained position as shown in FIGS. 14B, and 14D the wall segments 1212*a*, 1213*a* and 1212*b*, 1213*b* of walls 1210 and 1211 are pivoted. As shown in FIGS. 14B and 14D, the side walls are over center or slightly hyper-extended or pivoted outward to provide a strain in a width wise direction with the force transferred to the skin treatment device through attachment structures 1203, 1204. Thus the skin treatment device may be strained in orthogonal directions or at least two directions, i.e., the applicator provides a bi-directionally or multi-directionally strained skin treatment device. The applicator 1100 may be locked or maintained in a strained configuration by way of over center side walls. A latch or other stop such as a spring loaded pin may engage one or more of inside surfaces of wall segments 1212*a*, 1213*a* and 1212*b*, 1213*b* to maintain the applicator in its over center locked position.

As an option or alternative, the applicator 1200 may be provided with attachment structures 1236, 1237 that comprise a hook or loop structure of a hook and loop attachment mechanism, or any other attachment structure described herein. Likewise, side attachment structures 1203, 1204 may also be a hook or loop structure or any other attachment structure.

As indicated previously, such assemblies and devices may also be used to treat skin grafts (including split-thickness and full-thickness grafts, xenografts, cadaveric graft, autologous grafts), skin flaps and skin substitutes, with or without the use of biomaterials or biodressings, either on top and/or below the graft/flap/substitute, or otherwise in a treatment site. In some embodiments, these assemblies and devices may be configured to apply a wound device that applies a uni-axial or bi-axial (or other multi-axial) compressive force to a treatment site. In some variations, the axes of the straining force(s) acting upon the dressing via the applicator, or the compressive forces acting upon the tissue via the dressing, may be oriented such the dressing and/or applicator has or exerts a first directly applied force (i.e. not a subcomponent force derived from one or more applied forces, or a summation force from two or more other directly applied forces) and a second directly applied force that is not aligned, parallel or orthogonal to the first directly applied force. These forces may be further characterized as being orthogonal to the orientations of the edge intersected by that force. The magnitudes of the straining force(s) directly applied by the applicator to the dressing along each axis may be uniform or non-uniform. Nominally, when the applicator is released from the dressing, a portion of the multi-axial forces is transferred to the treatment site along each nominal axis. The amount of stress or strain applied by the wound device may be pre-determined, as described above. For example, a circular pre-tensioned wound device 2300 may be applied over a treatment site with a skin graft, flap or substitute 2301, as schematically illustrated in FIG. 14A. In some variations, a circular pre-tensioned wound device may be applied over a wound or pre-closed (e.g., sutured) wound of a treatment site. The adhesive perimeter 2302 of the wound device 2300 may circumscribe the skin graft 2301, and may help ensure that compression is applied all around the skin region with the skin graft 2301. The wound device 2300 may be configured to apply radially inward compressive forces (represented by arrows 2304) after it is adhered to the skin and the tension is released. FIG. 14B depicts one variation of a rectangular wound device 2310 that applies bi-axial compressive forces (represented by arrows 2314) when applied to a skin region with a skin graft 2311. As with the circular wound device 2300, the rectangular wound device 2310 may have an adhesive perimeter 2312. While circular and rectangular shaped wound devices are depicted and described, it should be understood that wound devices may have any desired shape (e.g., oval, triangle, trapezoid, square, any polygon, kidney-shaped, or irregularly shaped, etc.) and in some variations, may be shaped to accommodate the specific anatomical contours of the treatment site or custom-shaped to fit a particular wound of a particular individual.

Referring to FIGS. 15A to 15E, a tensioning device or radially tensioning device 3000 is illustrated that may be used to apply a radial strain to a circular, curved or arced portion of an elastic sheet by applying a radially tensioning or straining force continuously or at different points defining or along a curved or arced portion, perimeter, or edge of the diagnostic device, elastic sheet, and/or dressing. The tensioning device may be used to evenly distribute strain radially across a rounded elastic sheet. According to variations, an applied multi-axial strain may or may not be relatively uniform in a radial direction from a center point of an arc, curve or circle of a dressing. In some variations, the device may be configured to provide radial strain (e.g., where the direction of the strain radiates from a central region of a sheet or dressing). Such devices may be typically circular, oval, egg, kidney bean, or other arcuate shapes.

A tensioning member 3000 comprises a straining structure 3006 and a frame 3001. The straining structure 3006 comprises a handle portion 3007 and a plunger portion 3008. The frame 3001 comprises a support element 3002 having an opening 3003 configured to receive the plunger portion 3008 of the straining structure 3006, which is configured to fit within and extend through the opening 3003 of the frame 3001. At least a portion of a cross section of the opening 3003 has an arced, curved or circular shape which may be matched by the shape of the plunger portion 3008.

A elastic device assembly 3010 comprises a dressing elastic sheet 3011 removably coupled to an attachment sheet or attachment ring 3012. Prior to straining the sheet 3011, the attachment sheet or ring 3012 of the assembly 3010 may be attached via an attachment structure 3013 to the frame 3001 over the circumference of the opening 3003 of the frame 3001. The attachment structure 3013 may include or be coupled to the attachment sheet or ring 3012. As shown in FIG. 15D the attachment sheet or ring 3012 may be attached to the frame 3001 by way of an adhesive 3014 such as an acrylic adhesive (e.g., 3M™ adhesive 9475LE).

The attachment structure or structures 3013 are positioned or located in a circular, arced or curved configuration about the attachment ring 3012 so that the tensioning forces applied to the assembly 3010 and sheet 3011 may applied radially with respect to the circular, arced or curved shape.

Attachment structures of a dressing assembly, dressing carrier, support, base, applicator, tensioning or straining device may include any structures that are used to attach or couple an applicator, tension or straining device to a dressing. A dressing may or may not have attachment features or structures. Any such attachment features may be integral with or include any of the attachment structures or corresponding structures to the attachment structures of the applicator dressing and/or tensioning device.

In some variations the attachment structures may comprise one or more mechanisms or elements that may also be configured to facilitate separation, release, removal or detachment of the sheet from the applicator or tensioning device, other attachment elements, or other portions of the assembly, including but not limited to the separation devices and methods described herein. Release elements or releasable attachment structures may include but are not limited to pockets and tabs, hook and loop mechanism, hooks, angled bars, pivoting, rolling, rocking or sliding features associated with or coupled to attachment structures, adhesives, removable adhesives, adhesive tapes or other adhesive devices, pegs, rip cords, towel bar configurations, sliding pins, friction locks, cam locks, vacuum or suction devices, snap connectors, carpet tack, press fit connections or other connections, levers, latches, locking members, spring members, for example, or other mechanisms such as cutters or rip cords or other structures or features to facilitate tearing, cutting or separation of attachment structures or elements perforated or otherwise severable structures, that permit removal of sheet from the applicator, other portions of the assembly and/or attachment structures, features, elements or portions. They may be self-releasing latches or spring members. They may be actuated when a pressure member is applied to a skin treatment device prior to removing the applicator. They may be manually actuated.

In FIG. 15C, the straining structure 3006 is shown just prior to straining positioned, and facing the open side 3004 of the frame 3001 with the dressing assembly 3010 attached to an opposing dressing side 3005 of the frame 3001. At the sheet side 3005, the opening 3003 of the frame 3001 has a relatively larger diameter that matches or is larger than the diameter of the plunger portion 3008 of the straining device 3006. At the open side 3004 of the opening 3003, a chamfer 3009 may assist in guiding the plunger portion 3008 through the opening 3003. The plunger portion 3008 is slightly narrower that the smallest diameter of the opening in the frame while the handle portion 3007 is wider that the chamfer 3009 of the opening 3003, thus acting as a stop to limit straining of a sheet to a predetermined amount when the handle portion 3007 abuts the open side 3004 of the frame 3001 (see FIG. 15E).

Figure 15A:
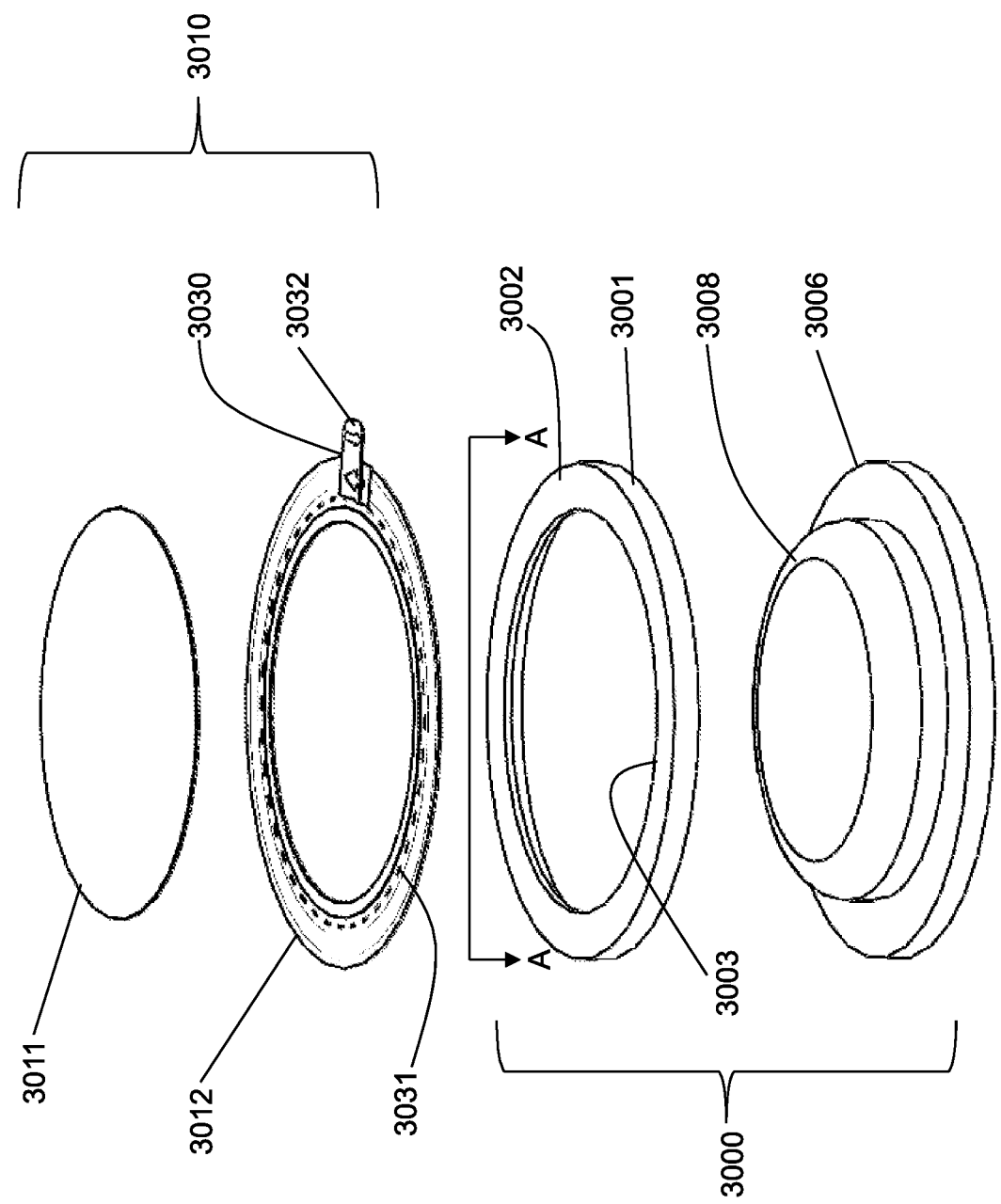
FIG. 15A is an exploded perspective view in a first direction of a tensioning device and dressing assembly.
Figure 15B:
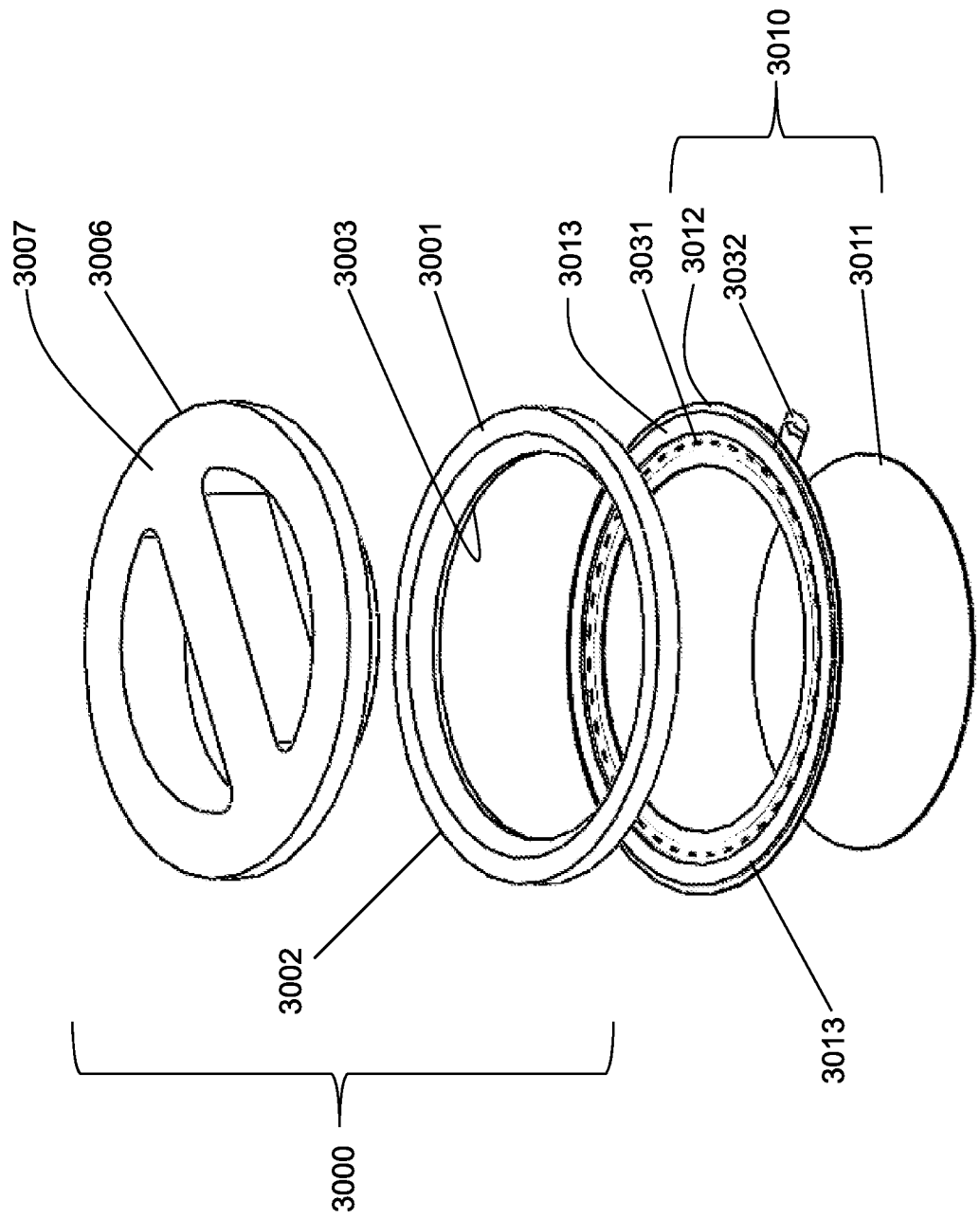
FIG. 15B is an exploded perspective view in an opposite direction of the tensioning device and dressing assembly of FIG. 15A.
Figure 15E:
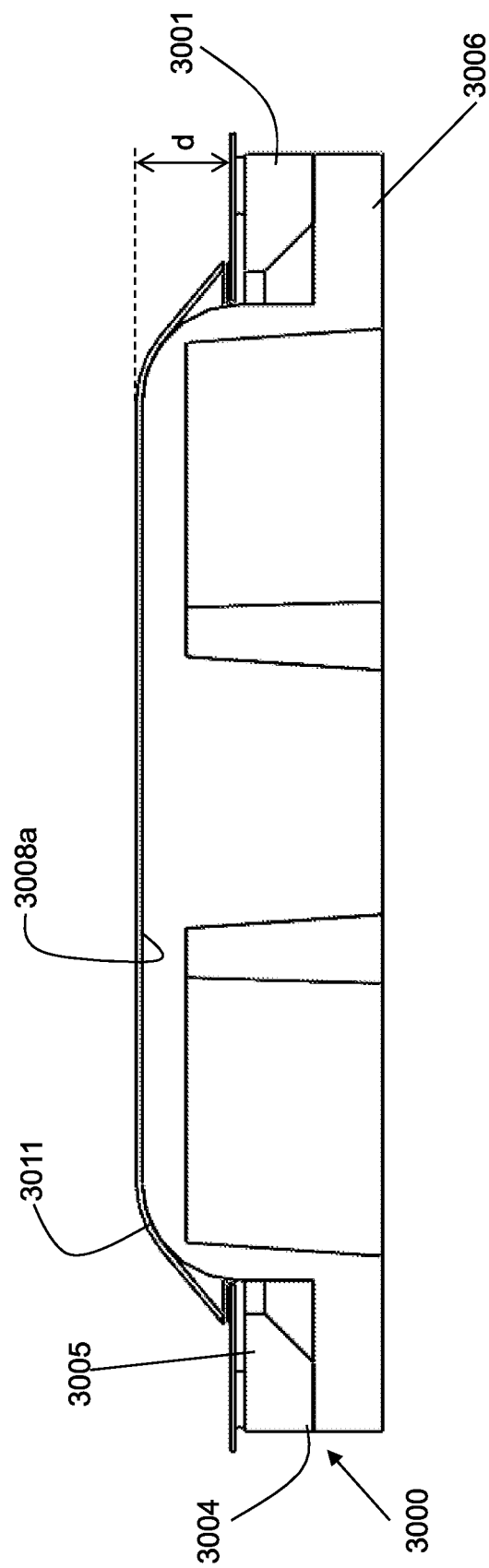
FIG. 15E is a cross-sectional view of a tensioning member straining a dressing of the dressing assembly of the dressing assembly and tensioning device of FIG. 18A.

In FIG. 15E, the tensioning device 3000 is shown straining the sheet 3011. The plunger portion 3008 is inserted through the opening until the handle portion 3007 abuts the open side 3004 of the frame 3001. The plunger portion 3008 extrudes past the dressing surface 3005 to which the sheet 3011 is coupled or attached to thereby strain the sheet 3011. The end 3008a of the plunger portion 3008 extends past the opening side of the frame a predetermined distance d, thus straining the sheet 3011 a predetermined amount. The area of the end 3008a of the plunger and the distance d determine the amount of strain applied to the sheet 3011.

As shown in FIGS. 15F and 15G, a plurality of straining structures 3006a and 3006b constructed similarly to straining structure 3006, are shown each with different side wall lengths d1 and d2 respectively. The amount the plunger portions extend past the sheet side 3005 of the frame 3001 will determine the amount of strain imparted to the sheet. Each of the straining structures 3006a and 3006b impart different predetermined amounts of strain to a sheet. According to variations, a straining device imparting a predetermined amount of strain to a sheet may be selected from a plurality of straining devices each delivering a predetermined amount of strain. According to variations, a kit comprising at least one assembly and support and a plurality of straining structures each imparting different amounts of predetermined strained to a sheet may be provided.

Once the sheet 3011 is strained, the tensioning device 3000 may be used to apply the dressing 3011 to a subject.

The sheet 3011 includes a layer of a skin adhesive 3021 such as a pressure sensitive adhesive e.g., as described herein, on an outwardly facing surface 3020 of the sheet 3011. An adhesive liner may be positioned over the adhesive layer and removed prior to straining.

After application of the sheet 3011, the sheet 3011 may be detached or separated from the tensioning device 3000 and the attachment sheet or ring 3012 using a removal structure 3030. As shown in FIGS. 15A to 15H, the attachment sheet or ring 3012 includes a circumferential perforation 3031 and pull tab 3032. The perforation 3031 is located circumferentially inside of the attachment points where the adhesive 3014 attaches the attachment sheet 3012 to the frame 3001. When the pull tab 3032 is pulled, the sheet 3011 is separated from the attachment sheet 3012 and the tensioning device 3000 may then be removed leaving the sheet 3011 on the skin. FIG. 15H illustrates a sheet 3011 that is applied to a skin surface. A portion of the attachment ring 3012 may be removed or may remain on the frame facing surface 3015 of the sheet 3011 after it has been applied to the skin.

In FIGS. 15A to 15H, the sheet, attachment sheet, attachment structures, frame, frame opening, and plunger portions are illustrated in a circular shape. Other round shapes or curved contours may be used as well.

According to some variations, the cover and/or base or elements or segments of a tensioning device may be constructed to be sufficiently firm or rigid or less flexible relative to an attached dressing to support an attached dressing until it is applied to a subject as described with respect to the variations herein. Such material may comprise, for example, a plastic, e.g., polypropylene, polycarbonate, polytetrafluoroethylene (PTFE or TEFLON®), LDPE, high-density polyethylene (HDPE), ultra high-molecular weight polyethylene (UHMWPE), polyvinyl chloride (PVC) or acrylic, nylon or a paperboard. The elements or segments may be a laminate of a material, such as a solid bleach sulfate paperboard with a layer of flexible material between layers of paperboard, for example, silicone, polyurethane, LDPE or a rubber material. The material may also be a metal as for example, ductile aluminum or stainless steel. The metal may comprise a foil, ribbon, wire or other form.

As noted previously, an applicator, tensioning device and/or straining device may be provided in some embodiments to impart a strain to a skin treatment device with an external force and/or to maintain a strain imparted to the skin treatment device. In some examples, the straining device may be configured to impart and/or maintain a single predetermined or pre-set strain or a plurality of predetermined or pre-set strains Features described herein with respect to an applicator may also be used in any tensioning or straining device that is used to strain a skin treatment device. An applicator, tensioning or straining device that is described as being in an unstrained configuration is in a configuration in which a skin treatment device may be unstrained or relatively less strained when attached to the applicator, tensioning or straining device. An applicator, tensioning, or straining device that is described herein has being in a strained configuration is in a configuration in which a skin treatment device may be strained or relatively more strained when attached to the applicator, tensioning or straining device. Features described herein with respect to an applicator may also be used in any tensioning or straining device that is used to strain a skin treatment device.

According to some variations the applicator, tensioning device, or carrier, support, or base may provide varied or variable flexibility to allow the dressing to be shaped when applied to various body locations or contours.

The applicator, tensioning device and/or attachment structure profile may be straight, curved or otherwise varied. For example, the shape of the elements of a device may be configured to follow the shape of the area of the subject's body to which the skin treatment device is to be attached. A tensioning device, applicator or elements thereof may be selected or configured to have a profile that has a desirable profile for a particular body location or profile where the skin treatment device is to be placed on a subject's skin. An applicator, tensioning device or elements thereof may be selected or configured to closely match a portion of a subject's body profile. The applicator or tensioning device and/or an element or segment thereof, may be curved, curvable, flexible, bendable, malleable, deformable, shapeable or movable to provide alternative shapes or profiles of an attached dressing. They may be relatively curved, curvable, flexible, malleable, bendable, deformable, shapeable or movable in at least one direction while being more rigid in another direction.

Figure 16:
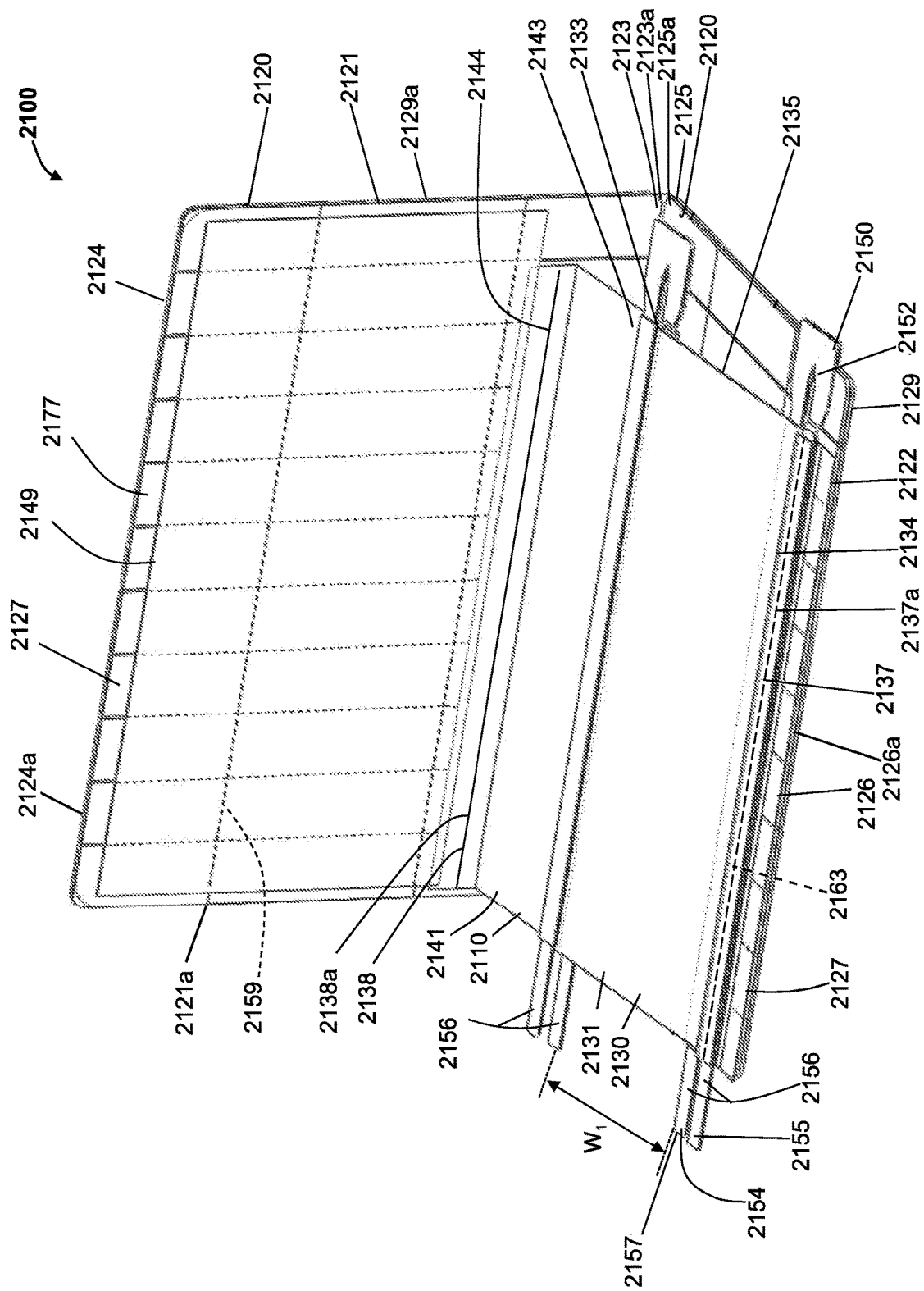
FIG. 16 is a perspective view of a tensioning device and elastic sheet.

Referring to FIG. 16, a variation of a system 2100 comprising an elastic sheet and tensioning device 1 is illustrated. The system 2100 comprises a book-like applicator and/or tensioning element 2120, an elastic sheet assembly 2110 including an elastic sheet 2130, and a release 2150 configured to release the elastic sheet 2130 from the applicator and/or tensioning device 2120.

The system 2100, applicator or tensioning device 2120 and/or elastic sheet assembly 2110 may be configured to pre-strain the elastic sheet 2130 and/or permit transfer of the pre-strained elastic sheet 2130 to the skin of a subject.

The device 2120 comprises a cover 2121 and a base 2122. The sheet assembly 2110 is removably coupled or anchored to the device 120 which may act as a carrier or a support for the elastic sheet. The cover 2121 may be generally planar and include sides 2123, 2124 with corresponding edges 2123a, 2124a along its length, and edges 2121a at opposing ends. The carrier or base 2122 may be generally planar and include sides 2125, 2126 with corresponding edges 2125a, 2126a along its length and edges 122a at opposing ends.

Cover 2121 and base 2122 are movably, hingedly or pivotably coupled at sides 2123, 2125.

The elastic sheet 2130 of the elastic sheet assembly 2110 has a first side or edge 2133 having a length, and a second side or edge 2134 having a length. The elastic sheet 2130 is coupled to the system 2100 along the lengths of the sheet's sides 2133, 2134. When the device 2120 is closed, the adhesive layer 2135 faces away from the base 2122 and is covered by a release liner 2149 that is attached to the inside surface 2177 of the cover 2121. The elastic sheet assembly 2110 also includes an attachment sheet 2141 having a first side 2143 and a second side 2144. The attachment sheet 2141 couples the elastic sheet 2130 to the cover of the device2 120 which when opened, exerts a straining force on the elastic sheet 2130 through the attachment sheet 2141. According to some variations, the attachment sheet 2141 is flexible while being relatively inelastic with respect to the elastic sheet 2130 and may be constructed, e.g., out of a low density polyethylene. When assembled, the attachment sheet 2141 is bonded to the elastic sheet 2130 at (for example, using a combination of a silicone PSA/acrylic PSA) or near the sides 2134 and 2143 of the elastic sheet 2130 and attachment sheet 2141 respectively. The attachment sheet 2141 is coupled at its side 2144 to the cover 2121 at attachment points 2137 defining a line or area of attachment 2137a along the length of the cover 2121. The elastic sheet 2130 is coupled to the second side 2124 of the base 2122 at a location near the first side 2133 of the elastic sheet 2130. As such, the elastic sheet 2130 is attached at attachment points 2138 defining a line or area of attachment 2138a along a length of the base 2122. A number of bonding methods or adhesives may be used to attach the attachment sheet 2141 to the cover 2121, for example, a low surface energy PSA such as an acrylic adhesive.

When the system 100 is in a closed or relaxed configuration the elastic sheet 2130 is relaxed or unstrained, with the elastic sheet 2130 having an unstrained width w1. As the tensioning device 2120 is opened to 180 degrees or up to about 360 degrees (e.g. by rotating or pivoting the cover 2121 with respect to the base 2122), the orthogonal distance increases between lines or areas of attachment 137a, 138a. According to some variations the assembly is opened to no less than about 180 degrees (minimum angular change) to provide for application of a dressing without interference of the system 2100. When the device 2120 is opened, it exerts a separation force between attachment regions defined by attachment lines or areas 2137a, 2138a or corresponding attachment areas. The force tensions the elastic sheet, creating a strain. Tensioning and imparting a strain on the dressing 2130 increases the width between attachment lines or areas 2137a, 2138a to a width greater than w1. The increase in the width may be a percentage of w1 or a percent strain.

The adhesive layer 2135 of the elastic sheet 2130 is protected by a release liner 2149 before the applicator or tensioning device 2120 is opened. The release liner 2149 is attached or glued to the inside surface 2177 of the cover 2121 so that when the cover 2121 is opened, and is separated from the base 2122 (prior to straining the elastic sheet 2130), the release liner 2149 is pulled away from the elastic sheet 2130 exposing the adhesive layer 135. Alternatively, a release liner may be provided on the adhesive layer 2135 that is not attached to the cover 2121. When the device 2120 is opened, and prior to straining the dressing 2130, the release liner may be manually removed from the elastic sheet 2130 to expose the adhesive layer 2135.

After the elastic sheet 2130 is strained, and the liner 2149 is released, the elastic sheet 2130 may be applied to a desired location on a subject's skin. A window 2159 may be used to visualize proper placement. The user may apply pressure to the back side 2129 of the device 2120 to activate the adhesive on the elastic sheet 2130 and/or to apply compression to a wound if used as a dressing. Alternatively, if the cover 2121 is rotated to 360 degrees, pressure may be applied to the inside surface 2177 of the cover 2121. Once applied to a subject, the elastic sheet 2130 may be released from the packaging, applicator or tensioning device 2120 using a release structure or mechanism 2150.

When the elastic sheet 2130 is strained and the adhesive 2135 is exposed, the elastic sheet 2130 may be applied with the adhesive side 2135 towards the skin of a subject. The side 2133 of the elastic sheet may then be released from the applicator by pulling the tabs 2156 to draw the blade 2152 across cutting path 2162. Also, the side 2134 of the elastic sheet may then be released from the applicator by pulling the tabs 2156 to draw the blade 2152 across cutting path 163. Thus the elastic sheet 2130 is released from the system 2100 (including the release 2150).

While this invention has been particularly shown and described with references to embodiments thereof, it will be understood by those skilled in the art that various changes in form and details may be made therein without departing from the scope of the invention. For all of the embodiments described above, the steps of the methods need not be performed sequentially.

The invention claimed is:

1. A system for determining a relative inherent skin tension at a location in a subject comprising:
   an elastic sheet of material and a skin adhesive; wherein the elastic sheet is configured to be strained a desired amount; wherein the elastic sheet comprises at least a first configuration and a second configuration wherein in the first configuration, the elastic sheet is strained, wherein the elastic sheet is further configured to be removably secured to a skin surface with the skin adhesive while in the first configuration and is configured to be released from the first configuration when adhered to a epidermal layer skin to adopt to the second configuration, and wherein the elastic sheet comprises attachment structures configured to radially strain the elastic sheet between the attachment structures and releasably couple a tensioning device configured to strain the elastic sheet, such that the tensioning device is configured to strain the elastic sheet the desired amount uniformly radially outward from a center of the elastic sheet and transfer force from the strained elastic sheet to the skin upon release;
   and a skin tension indicator configured to indicate a relative amount of inherent skin tension when the elastic sheet is adhered to an epidermal layer of skin in the second configuration.

2. The system of claim 1, further comprising:
   a plurality of skin treatment devices wherein each of the plurality of skin treatment devices has a different mechanical property; and
   wherein the skin tension indicator comprises a plurality of orientations configured to indicate one of the plurality of skin treatment devices.

3. The system of claim 1, wherein the skin tension indicator comprises at least one marking to the elastic sheet.

4. The system of claim 3, wherein the marking comprises a portion that is elongated in the second configuration with respect to a length in the first configuration.

5. The system of claim 1, wherein the skin tension indicator comprises a cutout of the elastic sheet.

6. The system of claim 1, wherein the attachment structures are configured to be used to uniaxially strain the elastic sheet.

7. The system of claim 1, wherein the attachment structures are configured to be used to multiaxially strain the elastic sheet.

8. The system of claim 1, wherein the skin tension indicator is configured to indicate a direction of a relatively greater inherent skin tension.

9. The system of claim 1, wherein the attachment structures are positioned in an arcuate configuration to apply tension forces radially with respect to the elastic sheet.

10. The system of claim 9, wherein the elastic sheet comprises an arcuate shape.

11. The system of claim 3, wherein the marking is symmetric in the first configuration and asymmetric in the second configuration.

12. The system of claim 3, wherein the marking is a circle.

13. The system of claim 3, wherein the marking is a plurality of radially intersecting lines.

14. The system of claim 1, wherein the elastic sheet is arcuate.

15. The system of claim 1, wherein the elastic sheet is circular.

16. The system of claim 1, wherein the elastic sheet is rectangular.

17. The system of claim 1, wherein the marking comprises a printed image.

18. The system of claim 1, wherein the marking comprises an embedded marking.

* * * * *